(12) United States Patent
McGregor et al.

(10) Patent No.: US 11,590,023 B2
(45) Date of Patent: Feb. 28, 2023

(54) LOW PROFILE FORCED-AIR BLANKET

(71) Applicant: 3M INNOVATIVE PROPERTIES COMPANY, Saint Paul, MN (US)

(72) Inventors: Andrew J. McGregor, Minneapolis, MN (US); Daniel P. Doran, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 768 days.

(21) Appl. No.: 16/343,004

(22) PCT Filed: Oct. 18, 2017

(86) PCT No.: PCT/US2017/057085
§ 371 (c)(1),
(2) Date: Apr. 18, 2019

(87) PCT Pub. No.: WO2018/075579
PCT Pub. Date: Apr. 26, 2018

(65) Prior Publication Data
US 2019/0374377 A1    Dec. 12, 2019

Related U.S. Application Data

(66) Substitute for application No. 62/411,279, filed on Oct. 21, 2016.
(Continued)

(51) Int. Cl.
*A61F 7/00*    (2006.01)

(52) U.S. Cl.
CPC ...... *A61F 7/0097* (2013.01); *A61F 2007/006* (2013.01); *A61F 2007/0091* (2013.01)

(58) Field of Classification Search
CPC ...... A61F 2007/0018; A61F 2007/0029; A61F 2007/0039; A61F 2007/0059; A61F 2007/006; A61F 2007/0091; A61F 7/0097
See application file for complete search history.

(56) References Cited

U.S. PATENT DOCUMENTS

| 4,457,295 A | 7/1984 | Roehr |
|---|---|---|
| 5,097,548 A | 3/1992 | Heck |

(Continued)

FOREIGN PATENT DOCUMENTS

| CN | 2715724 Y | 8/2005 |
|---|---|---|
| CN | 201492568 U | 6/2010 |

(Continued)

OTHER PUBLICATIONS

PCT International Search Report for PCT/US2017/057079 dated Apr. 7, 2018.

(Continued)

*Primary Examiner* — Tigist S Demie
(74) *Attorney, Agent, or Firm* — Jeffrey M. Olofson

(57) ABSTRACT

The invention includes a forced-air blanket for providing a profusion of air to a patient, comprising a bottom layer with a plurality of openings configured to allow a profusion of air to pass through the bottom layer and an upper layer bonded to the bottom layer around a periphery, wherein the upper layer is also bonded to bottom layer by a plurality of linear seals and a plurality of staked seals. In an embodiment, at least one of more of the linear seals have one end which is joined to a portion of the periphery. In another embodiment, the forced-air blanket may further include at least one elongated seal that is positioned proximate to the inlet. The arrangement of the plurality of staked seals, elongated seals and linear seals assists in providing a blanket that is of a low-profile with even air distribution.

7 Claims, 25 Drawing Sheets

Related U.S. Application Data

(60) Provisional application No. 62/435,917, filed on Dec. 19, 2016.

(56) References Cited

U.S. PATENT DOCUMENTS

| | | | |
|---|---|---|---|
| 5,405,370 | A | 4/1995 | Irani |
| 5,443,488 | A | 8/1995 | Namenye |
| 5,545,194 | A | 8/1996 | Augustine |
| 5,735,890 | A | 4/1998 | Kappel |
| 5,824,025 | A | 10/1998 | Augustine |
| 5,964,792 | A | 10/1999 | Augustine |
| 6,176,870 | B1 | 1/2001 | Augustine |
| 7,520,889 | B2 | 4/2009 | Van Duren |
| 2003/0135251 | A1 | 7/2003 | Schuessler |
| 2007/0073368 | A1 | 3/2007 | Cazzini |
| 2010/0161012 | A1* | 6/2010 | Van Liebergen ..... A61F 7/0097 607/107 |
| 2010/0211141 | A1 | 8/2010 | Pierre |
| 2011/0009930 | A1 | 1/2011 | Officier |
| 2014/0316494 | A1 | 10/2014 | Augustine |
| 2015/0196422 | A1 | 7/2015 | Teunissen |

FOREIGN PATENT DOCUMENTS

| | | |
|---|---|---|
| CN | 203634361 U | 6/2014 |
| EP | 0073291 A1 | 3/1983 |
| EP | 1009342 | 6/2000 |
| WO | WO 95/35077 | 12/1995 |
| WO | WO 97/14379 | 4/1997 |
| WO | WO 99/08631 | 2/1999 |
| WO | WO 2010/093458 | 8/2010 |
| WO | WO 2010/096161 | 8/2010 |
| WO | WO 2016/069551 | 5/2016 |
| WO | WO 2016/105461 | 6/2016 |
| WO | WO 2016/105462 | 6/2016 |
| WO | WO 2016/105475 | 6/2016 |
| WO | WO 2018/075575 | 4/2018 |
| WO | WO 2018/075576 | 4/2018 |

OTHER PUBLICATIONS

PCT International Search Report for PCT/US2017/057082 dated Jan. 18, 2018.
PCT International Search Report for PCT/US2017/057085 dated Jan. 18, 2018.
Covidien AG. © 2013 Covdien. "*WarmTouch™ Convective Warming System*" brouchure.
Tyco Healthcare Uk Ltd. © 2007 Nellcor Puritan Bennett LLC. "*WarmTouch® Convective Air Warming System*" brochure.
Supplementary European Search Report for EP 17 86 2189 dated May 6, 2020.

\* cited by examiner

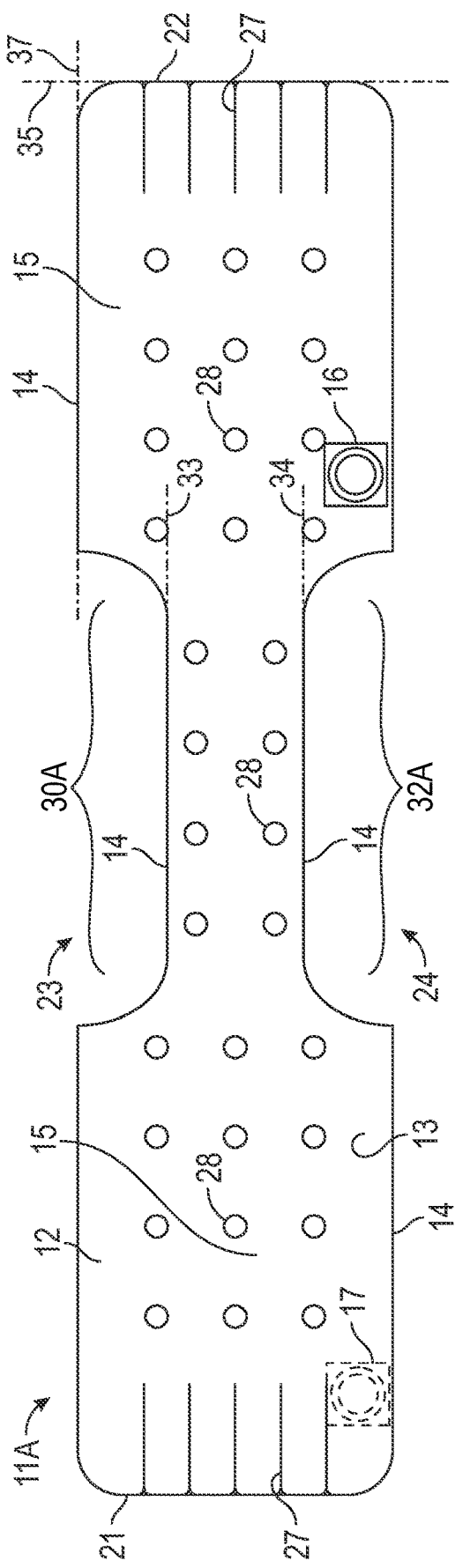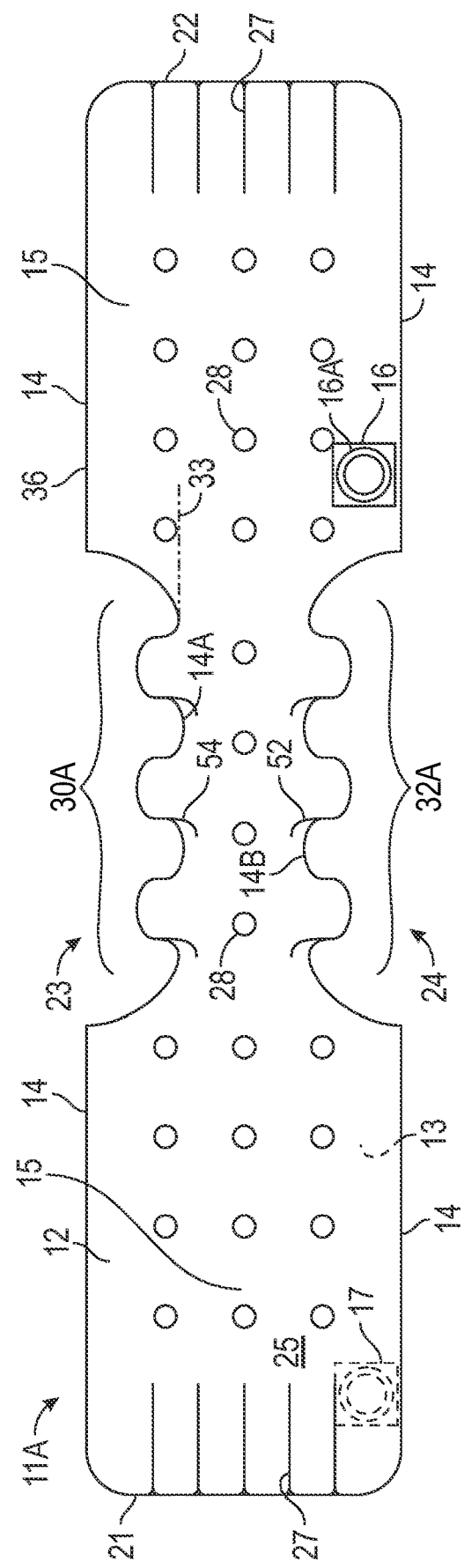

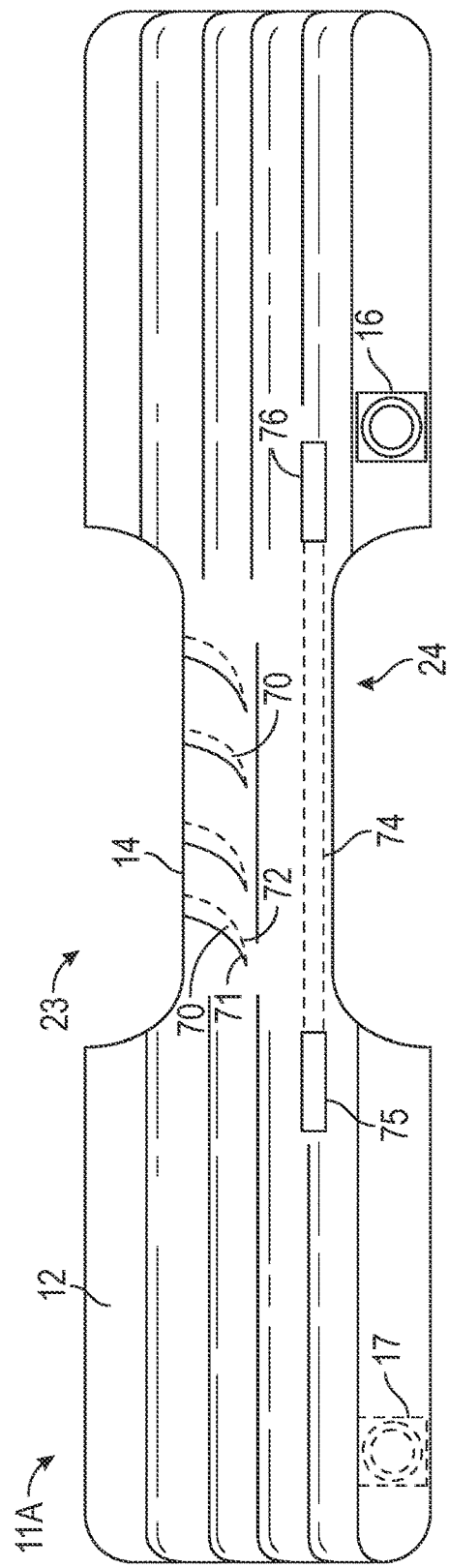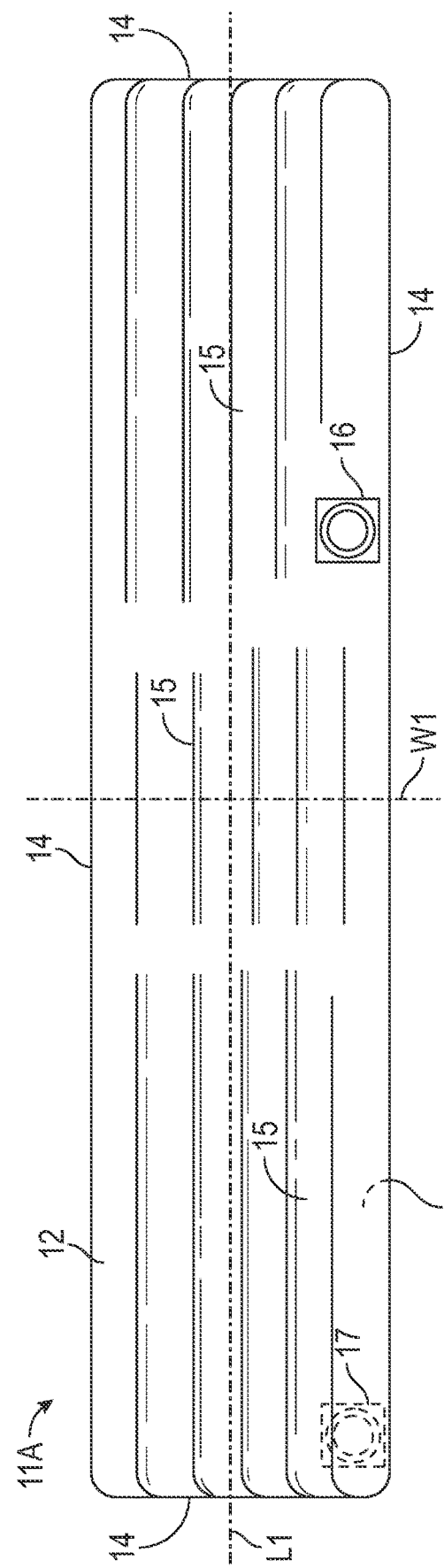

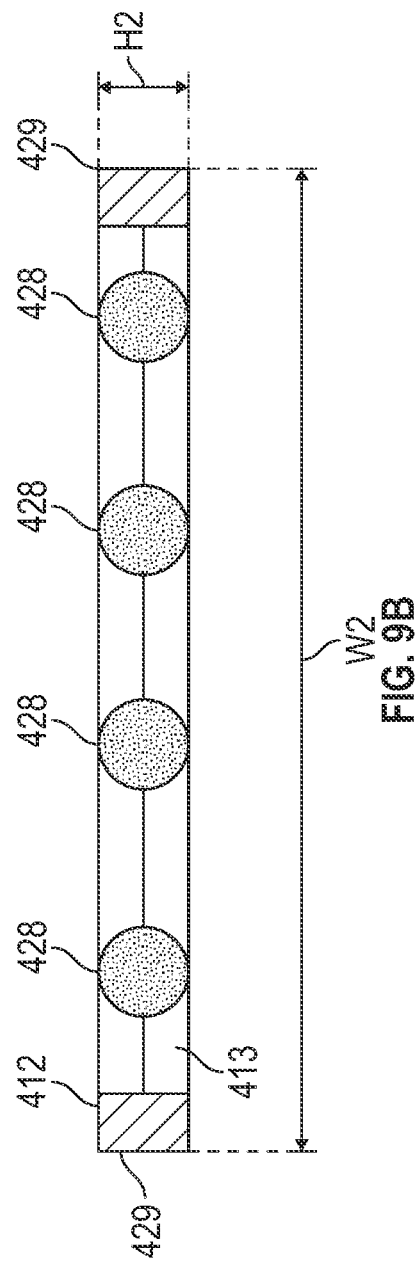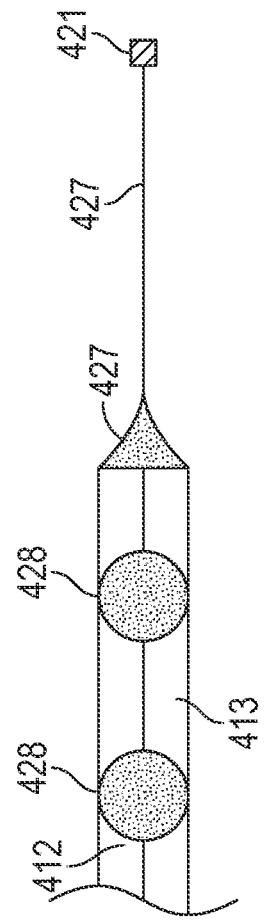

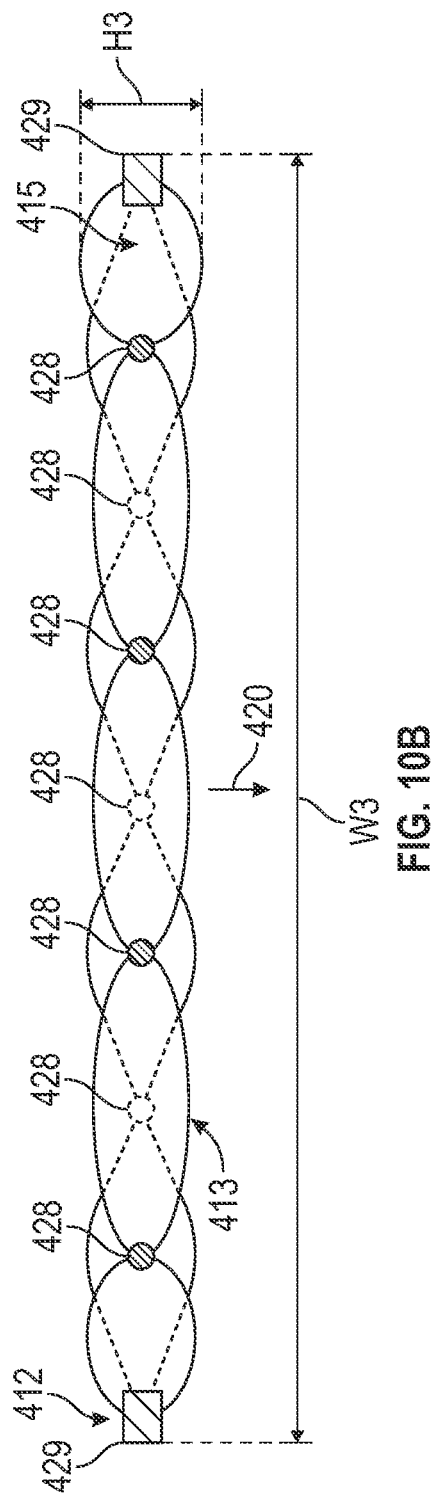
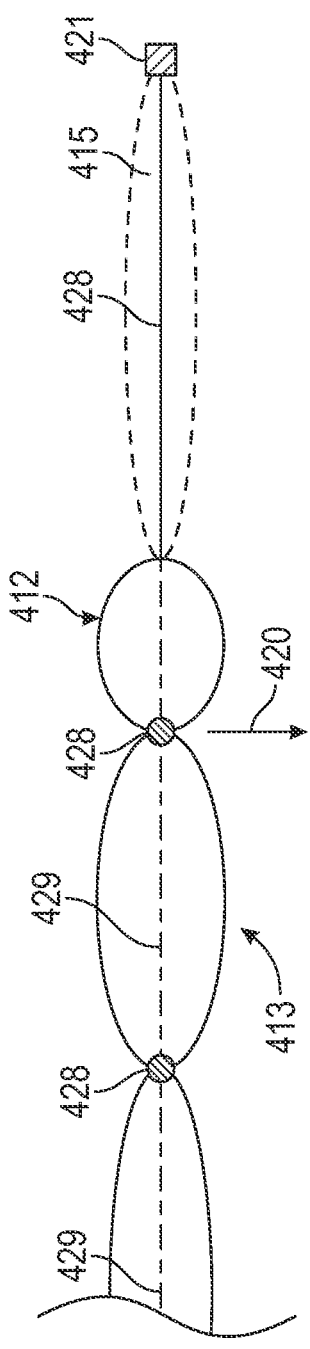

LOW PROFILE FORCED-AIR BLANKET

CROSS REFERENCE TO RELATED APPLICATIONS

This application is a national stage filing under 35 U.S.C. 371 of PCT/US2017/057085, filed Oct. 18, 2017, which claims the benefit of both U.S. Provisional Application No. 62/411,279, filed Oct. 21, 2016 and U.S. Provisional Application No. 62/435,917, filed Dec. 19, 2016, the disclosures of which are incorporated by reference in their entirety herein.

BACKGROUND

Patients who are preparing for, undergoing and recovering from a surgical procedure often require and are under the influence of anesthesia as part of the procedure. Due to the effects of the anesthesia, a patient may become unable to regulate their own core body temperature, a condition known as poikilothermia. Under these conditions, and when for example in an air-conditioned environment such as an operating room or a recovery area in a hospital or in a clinic, the lower air temperature and the need for the patient to be at least partially undressed may lead to the patient becoming hypothermic, wherein the core body temperature of the patient may begin to drop in an unintentional and undesirable manner.

One technique used to prevent hypothermia or other undesirable losses in body temperature of a patient when under the influence of an anesthetic is by the use of forced-air blanket to provide a profusion of warmed air to the patient. The blankets are generally constructed of a series of air passages and interconnected air ways formed between two layers of material. The first layer of material is generally non-porous, and is formed on one side of the blanket, and a second layer that is porous, or that includes distributed air-holes (e.g., perforations), is bonded in some fashion to the first layer of material to form the air passages and/or airways. The blanket is configured to be coupled to a device that warms a flow of air to a predefined temperature range, and then directs that warmed air, using a relatively low pressure, into the air passages and/or airways, often through a flexible tube or duct that may also be formed of a non-porous material. The warm air provided into the air passages and/or airway is expelled at a slow rate though the porous material or out through the distributed holes provided by the second layer of material due to the low level of air pressure generated between the first and second layers of material.

By placing the blanket for example over, underneath or in proximity to at least some portion or portions of the patient, the warmed air may be directed to the patient in a manner that assists the body of the patient in maintaining an acceptable core body temperature. Contact with the blanket itself by a portion or portions of the body of the patient may also help assist the body in maintaining the core body temperate within acceptable limits.

SUMMARY

In general, techniques are described herein allowing a disposable forced-air blanket having an initial shape and configuration that may allow the forced-air blanket to be placed adjacent to and/or cover a certain portion of a patient's body when the patient is in a first position and orientation. Forced-air blankets may also be referred to as an inflatable blanket, and the examples described in this disclosure are in reference to blankets referred to as either forced-air blankets and/or as inflatable blankets. The forced-air blanket includes and upper layer sealed to a bottom layer along a periphery that provides an enclosed initial shape to the forced-air blanket. In addition to the bonding of the upper and lower layers along the periphery, the upper layer may also be bonded by the lower layer at various locations within the enclosed initial shape of the forced-air blanket. The areas were the upper and lower layers are bonded together within the enclose shape at some locations may be a stake seal, wherein a particular area, such as a circular area, of the upper layer is bonded to bottom layer. The area where the upper and lower layers are bonded together within the enclosed shape at some locations may be a linear seal, wherein a length of the upper layer is bonded to the bottom layer along a line-shaped bond having a pre-determined length, and having a width of contact between the upper and lower layers. In some examples, at least one end of the linear stake is sealingly coupled to the bonding seal along the periphery.

A combination of stake seals and linear seals may be used to create a set of air passageways between the upper layer in the lower layer of the forced-air blanket so that when the forced-air blanket is inflated with a flow of air, the forced-air blanket provides a low profile convective structure that distributes the flow of air to the passageways of the blanket for distribution from the blanket through at least one of the bottom layer and upper layers. The configuration of the staked seals and the linear seals provides a low profile for the force-air blanket by maintaining the portions of the upper layer and the lower layer within a maximum distance relative to each other across the area enclosed within the periphery, while still providing adequate cross-sectional areas within the passageways between the upper and bottom layers to allow a desired level of air t flow through the passageways of the blanket.

Various examples described in the present disclosure are directed to a forced-air blanket for providing a profusion of air to a patient, the forced-air blanket comprising: a structure comprising a first layer of material and a second layer of material, the first layer of material forming a bottom layer of the forced-air blanket, the bottom layer comprising a plurality of openings configured to allow a profusion of air to pass through the bottom layer, the second layer of material forming an upper layer of the forced-air blanket, the upper layer bonded to the bottom layer around a periphery to form an area of the upper layer and the bottom layer enclosed within the periphery, the upper layer further bonded to bottom layer by a plurality of linear seals and a plurality of staked seals forming a plurality of interconnected air passageways; and at least one air inlet coupled to the interconnecting air passageways, the inlet configured to receive a flow of air, and to provide the flow of air to the bottom layer through the interconnected air passageways; wherein the area enclosed within the periphery of the forced-air blanket provides an interior space comprising the plurality of interconnected air passageways between the upper layer and the bottom layer, the passageways further defined by a plurality of connections formed between the upper layer and the bottom layer within the area defined by the periphery, and by the plurality of linear seals, and the plurality of staked seals, and wherein at least one of the plurality of linear seals is sealingly joined to a portion of the periphery.

Other examples described in the present disclosure are directed to a system for warming or cooling a patient, the system comprising: a source for generating a flow of air; and a forced-air blanket coupled to the source and configured to receive the flow of air from the source, and to distribute a profusion of the flow of air from one or more surfaces of the forced-air blanket, the forced-air blanket comprising: a structure comprising a first layer of material and a second layer of material, the first layer of material forming a bottom layer of the forced-air blanket, the bottom layer comprising a plurality of openings configured to allow a profusion of air to pass through the bottom layer, the second layer of material forming an upper layer of the forced-air blanket, the upper layer bonded to the bottom layer around a periphery to form an area of the upper layer and the bottom layer enclosed within the periphery, the upper layer further bonded to bottom layer by a plurality of linear seals and a plurality of staked seals forming a plurality of interconnected air passageways; and at least one air inlet coupled to the interconnecting air passageways, the inlet configured to receive a flow of air, and to provide the flow of air to the bottom layer through the interconnected air passageways; wherein the area enclosed within the periphery of the forced-air blanket provides an interior space comprising the plurality of interconnected air passageways between the upper layer and the bottom layer, the passageways further defined by a plurality of connections formed between the upper layer and the bottom layer within the area defined by the periphery, the plurality of linear seals, and the plurality of staked seals, and wherein at least one of the plurality of linear seals is sealingly joined to a portion of the periphery.

Other examples described in the present disclosure are directed to a method for forming a forced-air blanket, the method comprising: providing a first web layer that comprises a plurality of openings; providing a second web layer with or without perforations; forming an inlet in either the first web layer or the second web layer; and bonding the first web layer to the second web layer to form a sealed periphery and a plurality of linear seals and a plurality of staked steals.

Various examples described in the present disclosure are directed to a forced-air blanket for providing a profusion of air to a patient. The forced-air blanket includes a structure. The structure includes a first layer of material and a second layer of material. The first layer of material forms a bottom layer of the forced-air blanket. The bottom layer includes a plurality of openings configured to allow a profusion of air to pass through the bottom layer. The second layer of material forms an upper layer of the forced-air blanket, the upper layer bonded to the bottom layer around a periphery to form an area of the upper layer and the bottom layer enclosed within the periphery. The upper layer is further bonded to bottom layer by a plurality of linear seals and a plurality of staked seals forming a plurality of interconnected air passageways. The blanket includes at least one air inlet coupled to the interconnected air passageways. The air inlet is configured to receive a flow of air, and to provide the flow of air to the bottom layer through the interconnected air passageways. The area enclosed within the periphery of the forced-air blanket provides an interior space comprising the plurality of interconnected air passageways between the upper layer and the bottom layer. The passageways further defined by a plurality of connections formed between the upper layer and the bottom layer within the area defined by the periphery, and by the plurality of linear seals, and the plurality of staked seals. A first linear seal and a second linear seal of the plurality of linear seals are oriented longitudinally along the forced-air blanket. The plurality of staked seals are arranged in a plurality of parallel rows including a first row, a second row, with each row having at least a first staked seal and a second staked seal. The first linear seal and the second linear seal are adjacent to each other. The first row is collinear with the first linear seal and the second row is collinear with the second linear seal. The plurality of staked seals are arranged in a rectilinear array having a staggered pattern.

Various examples described in the present disclosure are directed to a forced-air blanket for providing a profusion of air to a patient. The forced-air blanket includes a plurality of layers with a plurality of interior seals bonding at least two of the plurality of layers. The forced-air blanket also includes at least one air inlet having a center coupled to at least one of the plurality of layers. At least one elongated seal from the plurality of interior seals is positioned proximate to the inlet, wherein an elongated seal has two sides, with one side facing the inlet.

BRIEF DESCRIPTION OF THE DRAWINGS

FIG. 4A illustrates an example warming system including an example of a warming blanket in accordance with one or more example implementations and techniques described in this disclosure.

FIG. 4B illustrates an example warming system including an examples of a variation of the warming blanket in accordance with one or more example implementations and techniques described in this disclosure.

FIG. 5 illustrates a top view of an example warming blanket according to the techniques described in this disclosure.

FIG. 6 is an example of a rectangular warming blanket according to the techniques described in this disclosure.

FIG. 9B shows a side cross-sectional view of the uninflated forced-air blanket of FIG. 9A viewed along the lines of 1-1.

FIG. 9C shows a side cross-sectional view of the uninflated forced-air blanket of FIG. 9A viewed along the lines of 2-2.

FIG. 10B shows a side cross-sectional view of the inflated forced-air blanket of FIG. 10A viewed along the lines of 1-1.

FIG. 10C shows a side cross-sectional view of the inflated forced-air blanket of FIG. 10A viewed along the lines of 2-2.

The drawings and the description provided herein illustrate and describe various examples of the inventive methods, devices, and systems of the present disclosure. However, the methods, devices, and systems of the present disclosure are not limited to the specific examples as illustrated and described herein, and other examples and variations of the methods, devices, and systems of the present disclosure, as would be understood by one of ordinary skill in the art, are contemplated as being within the scope of the present application. In addition, one or more reference numbers may be first introduced in a figure of the application to refer to a device, a method step, or some other aspect related to the figure, wherein the same reference number may then be used in a subsequent figure or figures to refer to the same device, method step, or other aspect as described with respect to the original figure, but without a particular reference to the same reference numbers in the description corresponding to the subsequent figure(s). In such instances and unless stated otherwise, the reference numbers as used in the subsequent figure or figures incorporate all of the features, functions, and the equivalents thereof of the devices, method steps, or other aspects described with respect to the reference number where first introduced and described.

DETAILED DESCRIPTION

As discussed above, systems, devices, and techniques are described herein with respect to a forced-air blanket having an initial configuration and shape, and formed of materials and/or configured in various ways that allow the forced-air blanket to provide an initial configuration and shape when inflated with a flow of air, and to provide a level of drapability to the forced-air blanket when inflated with the flow of air. Although examples of the systems, devices and techniques described throughout this disclosure refer to forced-air blankets and/or forced-air warming blankets, these systems, devices, and techniques are not necessarily limited to forced-air blankets, and may be equally applicable to pads, tubes, and other patient warming and cooling devices, and the equivalents thereof, as would be understood by one or ordinary skill in the art.

Figure 1:
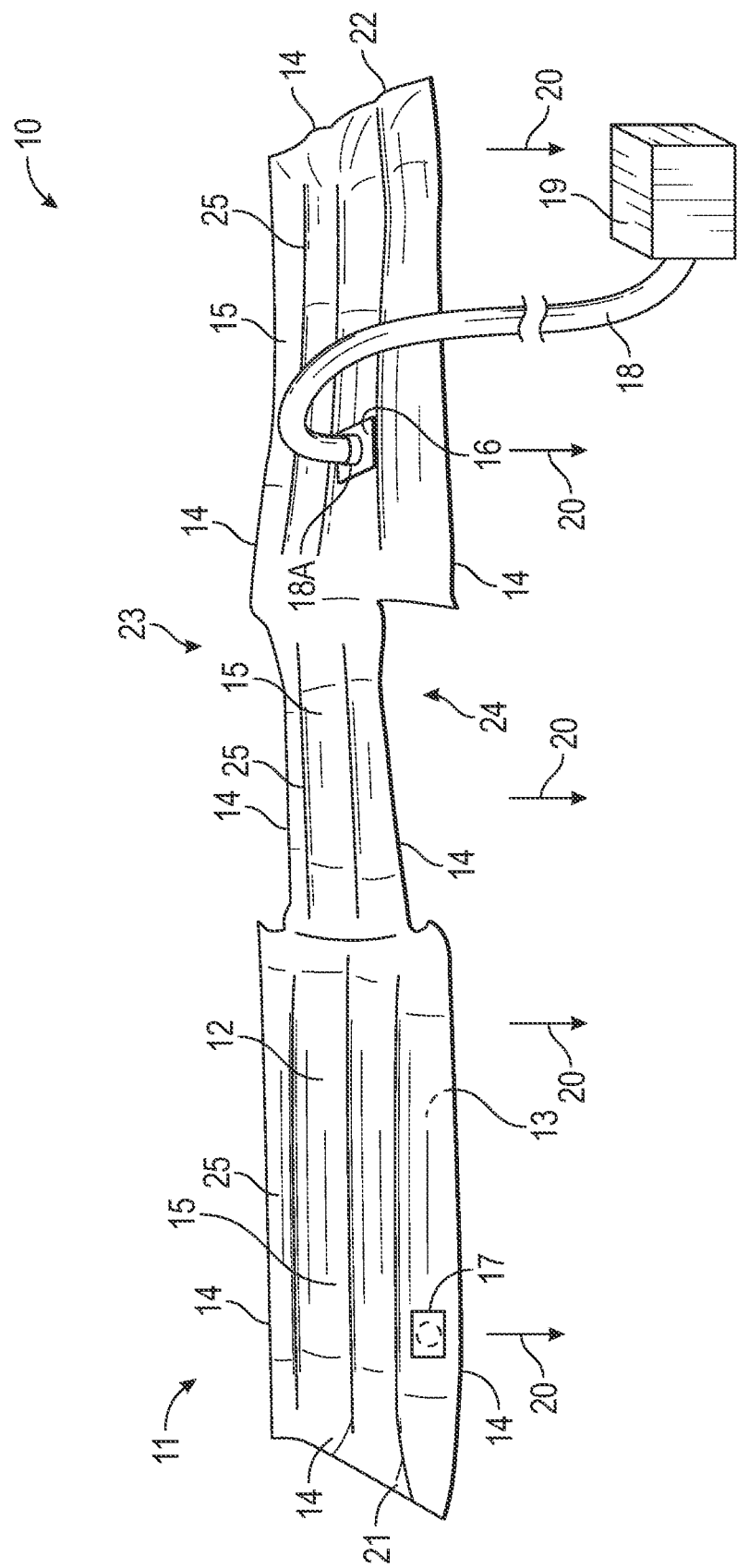
FIG. 1 is an illustrative of an example system 10 that includes a forced-air blanket 11 in accordance with one or more example implementations and techniques described in this disclosure.

FIG. 1 is an illustrative of an example system 10 that includes a forced-air blanket 11 in accordance with one or more example implementations and techniques described in this disclosure. In this example, forced-air blanket 11 includes upper layer 12 including one or more sheets of material, and a bottom layer 13 including one or more sheets of material. In various examples, upper layer 12 is a separate sheet or sheets of material that is bonded to bottom layer 13 along a periphery 14 of each the layers 12, 13. In other examples, upper layer 12 is a same sheet or sheets of material folded over bottom layer 13, or formed as a tube, and then bonded (sealed) along portions of the periphery 14, such as at the end 21 and the end 22, where the material is not already a continuous sheet, or along cutouts, such as cutout 23 and cutout 24 formed along the periphery 14 in each of the upper layer 12 and the bottom layer 13. Upper layer 12 may also be bonded to bottom layer 13 at portions of the upper layer 12 that are not along periphery 14 to form seals 25 where upper layer 12 contacts bottom layer 13. Seals 25 as provided across the area 31 enclosed by periphery 14 may include staked seals in some areas, and may include linear seals in other areas. The spaces between upper layer 12 and bottom layer 13 and between the seals 25 form a plurality of interconnected passageways, generally indicated as passageways 15.

The seals 25 may or may not extend to the periphery 14 along the edges of force-air blanket 11, and the spaces between upper layer 12 and bottom layer 13 and between the seals 25 form a plurality of interconnected passageways, generally indicated as passageways 15. Passageway 15 within forced-air blanket 11 are coupled to an inlet 16 including an opening to the passageways from outside the forced-air blanket 11, in some examples to receive a coupling 18A. Coupling 18A may also couple inlet 16 to a tubular air hose 18 at one end of hose 18, the opposite end of hose 18 coupled to a source 19 for a flow of air. Inlet 16 may include a collar 16A surrounding the opening in 16A that may form a ring or a thicker portion of inlet 16 to allow for coupling and securing a device, such as couple 18A, to inlet 16. In various examples, forced-air blanket 11 further comprises an opening 17, which may be located on upper layer 12, and including another opening to the passageways 15 from outside the forced-air blanket 11. Opening 17 may be configured in a same manner as inlet 16. Opening 17 may in some examples be located on upper layer 12. Opening 17 may initially be sealed in some manner to seal the passageway provided through opening 17 in order to block the flow of air from passageways 15 through opening 17, and may be unsealed, for example by removing a seal (not shown in FIG. 1) from opening 17 to allow the forced-air blanket 11 to be coupled to another forced-air blanket (not shown in FIG. 1).

The sealing of an opening 17 in a forced-air blanket is not limited to any particular device or method of sealing the opening. In various examples, a layer of film formed of plastic or formed of a paper product may be affixed to a housing plate surrounding opening 17 by a semi-permanent adhesive, such as adhesives described below. The adhesive may allow the film to be held in place to seal opening 17 again the air pressures provided in passageways 15 of forced-air blanket 11, and may also be peeled off or otherwise removed to allow access to opening 17, for example to insert a coupling device into opening 17.

Source 19 may be any device that is configured to provide a flow of air at a temperature that may be applied to a patient (not shown in FIG. 1) safely while the patient is preparing for, undergoing, and/or recovering from a procedure where the patient is under the influence of an anesthetic or to otherwise warm a patient that may feel cold. The flow of air from source 19 is provided to hose 18 at a relatively low pressure, for example a pressure less than 100 mm Hg, and in some examples is less than 10 mm Hg, and flows through hose 18 to inlet 16, where the air flow of air continues into the passageways 15 of forced-air blanket 11, and inflating the forced-air blanket to fill the passageways 15 via the flow of air provided to inlet 16. In some embodiments more than one inlet may be provided. Throughout the disclosure, the flow air provided to inflate one or more of the forced-air blankets may be described as a "flow of warmed air." In reference to a flow of air or a flow of warmed air, the air provided to the forced-air blanket or blankets may be warmed to a temperature in a range of 36 to 43 degrees Celsius. However, a flow of air provided to a forced-air blanket as described in this disclosure also includes providing a flow of air at some other temperature, for example at an ambient temperature, or air that has been cooled to below an ambient temperature.

Each of the upper layer 12 and the bottom layer 13 may include one or more sheets, where each sheet may be formed from a different material. In some implementations, the upper layer 12 and/or the bottom layer 13 may include an underside sheet formed from a flexible, fibrous, preferably non-woven structure composed of polymeric materials capable of bonding to an upper side sheet of a heat-sealable polymeric material. For example, the underside sheet may be a non-woven, hydroentangled polyester material and the upper side layer may include a polyolefin such as a polypropylene film which is extrusion-coated, thermally laminated, or adhesively laminated onto the polyester layer. Alternatively, the underside sheet may comprise a non-woven, paper-based material to which the upper side layer, including either a polyethylene or polypropylene film, has been glue laminated. In one embodiment, the upper side and underside sheets can be made with a stratum of absorbent tissue paper prelaminated with a layer of heat-sealable plastic. In some cases, both the first layer and the second layer can include a same polymer material.

In some embodiments, the bottom layer 13 includes the upper side sheet and the underside sheet, and the upper layer 12 comprises the same material as the upper side sheet of the second layer. The upper layer 13 thus may include a sheet of plastic bonded to the plastic upper side of the second layer. It is preferably attached by a continuously-running web process including stations that provide an interruptible heat-sealing process. This interruptible heat sealing process can be controlled to form elongated heat seals, shown as seals 25, that define the inflatable channels therebetween. The seals can be formed as continuous air impervious seals or discontinuous air permeable seals. The interruptible heat sealing process can be used to form the continuous seams, one of which is the periphery 14 at the peripheral of the upper layer 12 and the bottom layer 13. In some cases, the interruptible heat sealing process can be used to form the discontinuous heat seals. In some cases, absorbent material can be applied to the forced-air blanket 11, for example, applied as a single material layer. The absorbent material can be bonded to the upper plastic layer by heat processing or by adhesive bonding.

In some embodiments, the forced-air blanket 11 is enabled to bathe a patient in the thermally controlled inflation medium introduced into the forced-air blanket 11 when inflated, via an air permeable layer, the first layer and/or the second layer. A layer can be air permeable using apertures generating openings over the area of the layer. In some implementations of an air permeable sheet with apertures, the density of apertures can vary among areas and/or inflatable sections.

In some embodiments, the upper layer 12 and/or the bottom layer 13 are made from a polyolefin non-woven extrusion coated, each with a coating of polypropylene on one side. In some other embodiments, the upper layer 12 and/or the bottom layer 13 can be poly lactic acid spunbond with polyolefin based extrusion coat. One of the upper layer 12 and bottom layer 13 may have openings formed by punching, slitting, or cutting to permit the flow of pressurized inflation medium, e.g., a flow of air, from the inflated section through the layer. In some cases, the holes can be opened through both layers. In some cases, when the forced-air blanket 11 is assembled, the polypropylene-coated side of the upper layer 12 is sealed to the polypropylene-coated side of the bottom layer at the periphery 14, and at the one or more locations such as seals 25 to form the construction. The sealing process can use various techniques, for example, ultrasonic welding, radio frequency welding, heat sealing, or the like. Alternatively, the upper layer 12 and bottom layer 13 may each include a laminate of polypropylene and polyolefin web with holes formed in at least one of the layers to support passage of pressurized air. In yet another embodiment, at least one of the layers can use air permeable material, for example, spunbond-meltblown-spunbond (SMS) nonwoven material, or the like.

Upper layer 12 of the forced-air blanket 11 is generally comprised of a material that may be formed from a porous or a non-porous material that may or may not be perforated. If made from a porous material or from a non-porous material, the upper layer 12 may provide a path of air flow from passageways 15 through upper layer 12 for some portion of the flow of air within passageways 15 to exit the forced-air blanket. If upper layer is formed from a non-porous material that is not also perforated, upper layer 12 does not provide a path for air to flow from passageways 15 through the upper layer 12. In one preferred embodiment, the non-porous and non-perforated characteristic of the upper layer 12 helps to maintain a low level of air pressure within the passageways 15 based on the air flow and air pressure provided by source 19 to inlet 16. In contrast, bottom layer 13 is formed from a material that has been further processed to include a plurality of perforations (e.g., openings in bottom layer 13, not specifically shown in FIG. 1) that allows air to flow from passageways 15 to an area outside the forced-air blanket, the airflow generally indicated by arrows 20 in FIG. 1. The perforations may be sized and distributed over the surface areas of the bottom layer 13. The sizing and distributing of the perforations is configured to allow the air flow, generally indicated by arrows 20, to be provided across the surface area including the bottom layer 13, while providing enough backpressure and to allow for inflation of passageways 15, and thus to provide a gentle and in some instances a warming air flow (e.g., arrows 20) when source 19 is providing the air flow to inlet 16 within a predetermined range of pressures and rates of air flow. In some examples, source 19 provides pressurized air at a flow rate of 40 to 50 cubic feet per minute (CFM). In some examples, source 19 provides pressurized air at a flow rate of 35 to 60 CFM. In some examples, source 19 provides pressurized air at a flow rate of 40 to 60 CFM. In some cases, source 19 provides pressurized air at a flow rate of 43 to 47 CFM.

In addition, the material used to form bottom layer 13 in conjunction with the amount of area allocated to perforations compared to the amount of area that is not perforated across bottom surface 13 provides a drapability to the forced-air blanket 11 when the forced-air blanket is placed over a patient. Drapabability refers to the ability of the forced-air blanket to bend over and conform to the contours of a patent when the inflated forced-air blanket is placed over an object that is not a planar shape, such as the torso and/or arms of a patient.

Forced-air blanket 11 may be placed over a patient (not shown in FIG. 1) and proximate to portions of the body of the patient, so that the bottom layer 13 is facing the portions of the patient that are to be warmed. Forced-air blanket 11 may then be deformed to drape over the contours of the patient to at least some extent. As such, the forced-air blanket 11 may be placed over a patient (not shown in FIG. 1) and proximate to portions of the body of the patient and subsequently inflated. For example, forced-air blanket 11 may be place over the upper torso and arms of a patient, for example during times when direct or immediate access to these portions of the patient are not required by other personnel, such as a physician or a surgeon. In other examples, the forced-air blanket may be detachably made as part of a gown (not shown in FIG. 1) that may be worn by the patient while waiting for the process that is to be performed on the patient to begin. In such instances, the detachable forced-air blanket may be detached from the gown when the gown is fully or partially removed from the patient in preparation for the actual procedure, and the forced-air blanket repositioned proximate to the patient to provide patient warming. Once in place, the air flow from the forced-air blanket 11 (generally indicated by arrows 20) may be directed to the portions of the patient proximate to the forced-air blanket, and thus provide a gentle and warming air flow and or a warm surface provided by the external surface of bottom layer 13 that warms the patient. The ability of the forced-air blanket to drape over and conform to the shape of the patient, while still providing a flow of air from the bottom surface 13 across generally the entirety of the bottom layer 13 may provide better ability to warm to the patient when using forced-air blanket 11.

As illustrated in FIG. 1, forced-air blanket 11, when inflated by the flow of air provided by source 19, provides a particular shape dictated to a large degree by the periphery 14, and by seals 25, which holds the upper layer 12 and the bottom layer 13 in relative close proximity to one another across the length and width dimensions of the forced-air blanket. For example, the forced-air blanket 11 as illustrated in FIG. 1 provides a substantially rectangular shape relative to the length dimension (e.g. between ends 21 and 22), and the width dimension, (dimension perpendicular to and coplanar with the length dimension), but also including cutouts 23 and 24 that narrow the width dimension of the forced-air blanket over a central portion of the forced-air blanket. This initial configuration and shape for force-air blanket 11 may be used to warm the upper torso and outstretched arms of a patient for example when the patient is lying on their front or back side with arms positioned in an outstretched direction perpendicular to the torso. In such instances, the narrow portion of the forced-air blanket created by cutouts 23, 24 may be placed over the torso, and the portions of the forced-air blanket extending outward from this central portion may be used to cover and warm each arm, respectively, of the patient.

As further described below, examples of forced-air blanket 11, and the equivalents and variations thereof, have at least a portion of the forced-air blanket that comprise a material or materials that, in conduction with opening provided in the bottom layer 13 and/or in upper layer 12 and the seals 25, allow the forced-air blanket to be deformed, for example in a manner that allows the forced-air blanket to drape over the contours of a patient when the forced-air blanket is placed over a patient. In various examples, deformation of the forced-air blanket can occur either before or after the forced-air blanket is inflated with a flow of air, such as a flow of air provided at inlet 16 by source 19. In various examples, deformation of the forced-air blanket includes the ability of the forced-air blanket 11 to drape over the patient when the forced-air blanket is placed over the patient in some manner.

Figure 2A:
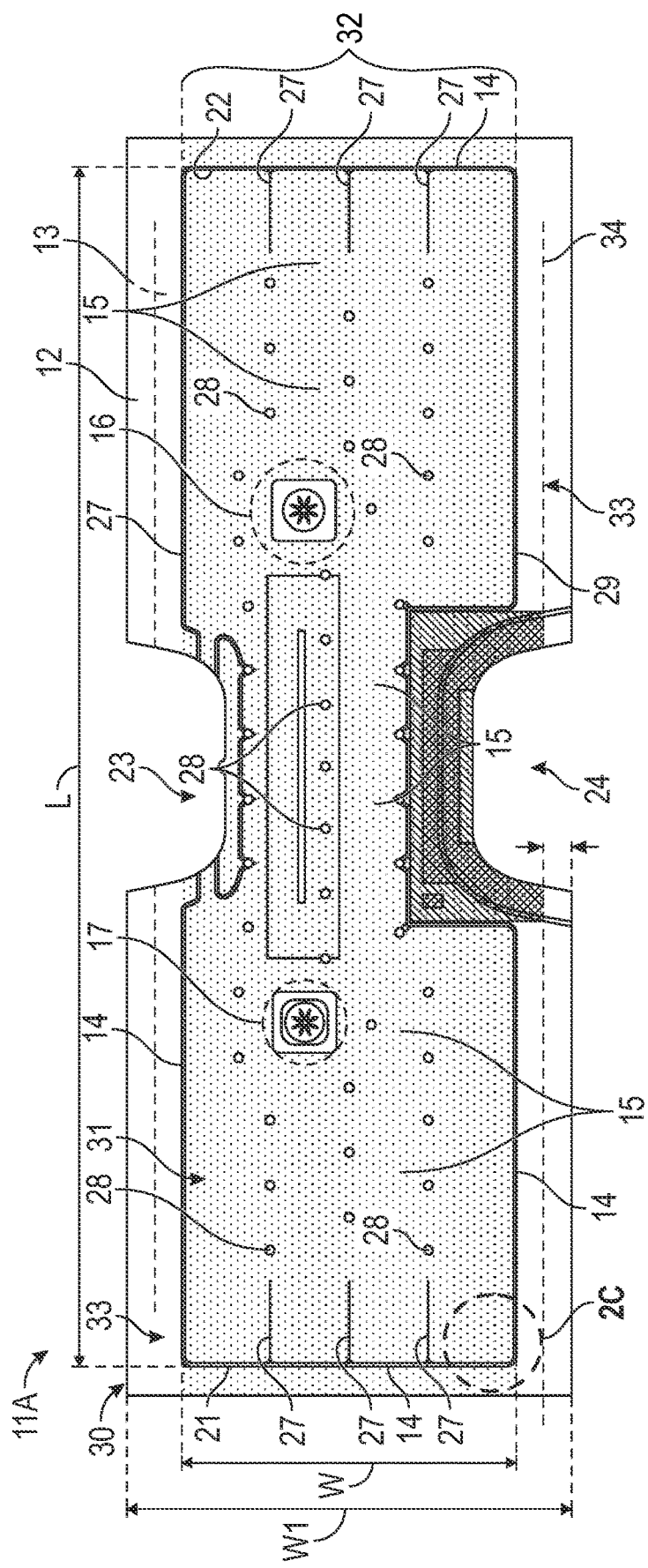
FIG. 2A illustrates a top view of various dimensional aspects and other characteristics of an example forced-air blanket 11A in accordance with example implementations and techniques described in this disclosure.

FIG. 2A illustrates a top view of various dimensional aspects and other characteristics of an example forced-air blanket 11A in accordance with example implementations and techniques described in this disclosure. As illustrated, forced-air blanket 11A is formed as part of a web, generally indicated as web 30, including an upper layer 12 and a bottom layer 13. In some examples, upper layer 12 has a thickness dimension in a range of 0.0005 to 0.02 inches for the material forming the upper layer. In some examples, and the bottom layer 13 has a thickness dimension of between 0.005 and 0.02 inches for the material forming the bottom layer.

Forced-air blanket 11A may be forced-air blanket 11 as illustrated and described above with respect to FIG. 1, and may include one or more of the features and provide one or more of the functions of forced-air blanket 11, as illustrated and described with respect to FIG. 1. As illustrated in FIG. 2A, forced-air blanket 11A includes the periphery 14 sealingly coupling upper layer 12 and bottom layer 13, and providing an initial shape, including a width dimension W, and a longitudinal dimension L between ends 21 and 22, and a narrowed central portion midway along this longitudinal dimension, generally indicated by cutouts 23, 24. Longitudinal dimension L is some examples is in a range of 60 to 90 inches, and width dimension W may be in a range of 15 to 40 inches. Upper layer 12 and bottom layer 13 form interconnected passageways 15 that are coupled to receive a flow of air provided to inlet 16, and to distribute the air throughout passageways 15 to be expelled out through the opening provided in bottom layer 13.

As shown in FIG. 2A, the layer of web 30 providing bottom layer 13 of forced-air blanket 11A includes a band of opening that perforate the bottom layer 13, generally indicated by bracket 32. The openings have a dimension, such as a diameter in examples having round shaped openings, and a spacing between the centers of the openings. In various examples, the openings are round in shape at the external surface of bottom layer 13, and in some examples have an area of the opening of about 0.48 $mm^2$ and in some examples in a range of 0.20 to 0.8 $mm^2$. The spacing and the quantity of the openings provided across the bottom layer 13 as provided within the area 31 enclosed by periphery 14 in some examples has a total perforation area about 23.13 $cm^2$ and in some examples in a range of 10 to 40 $cm^2$ over an inflated area for bottom layer 13 enclosed within the periphery 14 of about 7056 $cm^2$. In various examples, web 30 provides a band of openings that perforate bottom layer 13 and a band of openings that also separately perforate upper layer 12. In some examples, the opening in the upper layer 12 are a same size and are arranged in a layout across upper layer 12 that includes a same size and a same arrangement as provided by the opening provided in the bottom layer 13.

In addition to the bonding between upper layer 12 and bottom layer 13 provided by periphery 14, upper layer 12 and bottom layer 13 are also bonded together at various locations within the area enclosed by periphery 14. For example, forced-air blanket 11A may include a plurality of linear seals, generally represented by linear seals 27 in FIG. 2A. Linear seals 27 each bond a linear section of the upper layer 12 to the bottom layer 13 within the area of forced-air blanket 11A that is enclosed by perimeter 14. In some examples, the length of the contact along a linear seal 27 is between 5 to 25 cm, and the boding width along the linear seal 27 where upper layer 12 is bonded to bottom layer 13 is in a range of 2 to 20 mm. In various examples, an end of each of the linear seal 27 sealingly joins to the bonding provided by a portion of perimeter 14. For example, as shown in FIG. 2A, each of the linear seals 27 located at end 21 of forced-air blanket 11A have a longitudinal orientation that corresponds to the longitudinal dimension L of the forced-air blanket, and have a first end that joins with the periphery 14 at end 21 to form a seal with periphery 14. A second end of each of these linear seals 27 at end 21 that is opposite the first end joining periphery 14 is open to the passageways 15 within the interior space between upper layer 12 and bottom layer 13. Additional linear seals 27 located at end 22 of forced-air blanket 11A have a longitudinal orientation that corresponds to the longitudinal dimension L of the forced-air blanket, and have a first end that joins with the periphery 14 at end 22 to form a seal with periphery 14. A second end of each of these linear seals 27 that is opposite the first end joining periphery 14 is open to the passageways 15 within the interior space between upper layer 12 and bottom layer 13. Further, the spaces between each of the linear seals 27 and another linear seal 27, and the spaces between each of the linear seals 27 and periphery 14 along the longitudinal sides 27, 29 of forced-air blanket 11A are also open to passageways 15.

In addition to the bonding between upper layer 12 and bottom layer 13 provided by periphery 14, and linear seals 27, upper layer 12 and bottom layer 13 are also bonded together at various location within the area 31 enclosed by periphery 14 by a plurality of staked seals, generally indicated as staked seals 28 in FIG. 2A. Stakes seals 28 may include a particular area of upper layer 12 that is bonded to bottom layer 13, and is located within the area 31 enclosed within periphery 14. As illustrated in FIG. 2A, the area confined as the staked seal is circular but the staked seal could be of any shape which has an area. In some examples, the area in a range of 0.5 to 5.0 $cm^2$ of each of the upper layer 12 and the bottom layer 13 where the stake seal bonds these layers to be in contact with each other. The stake seal is not limited to having a particular shape or a particular amount of area included in the areas of upper layer 12 and upper layer 13 that are in contact and bonded together at a particular stake seal. In various example, the stake seal 28 may provide a square, a rectangular, a triangular, or an elliptical shape with respect to the area of contact between upper layer 12 and bottom layer 13.

The arrangement of staked seals 28 within area 31 is not limited to any particular arrangement of the staked seals relative to each other, and/or relative to any linear seals 27 provided with forced-air blanket 11A. Some of the staked seals 28 may be provided in rows and/or columns arranged across to the surfaces of upper layer 12 and bottom layer 13. In some examples the air channels are formed by the row or row of staked seal and linear seals, wherein the linear seals are located at the ends of the warming blanket, and the rows of staked seals are located in the portions of the warming blanket away from the ends. In some examples, a row or a portion of a row of staked seals may align with the linear orientation of at least one linear seal. In various examples, one or more of staked seals 28 may not align with the rows and/or columns formed by other ones of the staked seals 28, and/or may not align with the linear orientation of any one of the linear seals. Further, the number of staked seals provided within the area 31 enclosed by periphery 14 is not limited to any particular total number of staked seals. In some examples, the staked seals 28 are only provided in portions of the forced-air blanket 11A that are not already staked by a linear seal, such as liner seals 27.

When formed as part of a web 30, the area 31 of forced-air blanket 11A that is enclosed within periphery 14 may have dimension that are smaller than the dimensions of web 30. For example, forced-air blanket 11A may have a length dimension L, wherein web 30 may have an indeterminate length greater than length dimension L. In some examples, additional forced-air blankets (not shown in FIG. 2A) may already have been form along the length of web 30, and/or web 30 may include additional length that is to be formed into additional forced-air blankets (also not shown in FIG. 2A). Web 30 may have a width dimension W1 that is greater than the width dimension W of forced-air blanket 11A. In such examples, when a forced-air blanket is formed on web 30, excess areas may be left along the longitudinal sides of forced-air blanket 11A, the excess areas generally indicated as areas 33. In various examples, the excess areas 33 may include cutlines 34, wherein cutlines 34 provides a weaken area of the web 30 that allows at least some portion of the excess areas 33 to be torn or otherwise removed from the sides of forced-air blanket 11A. In addition, the web 30 may also be cut or torn across the width dimension of the web 30 in order to separate forced-air blanket 11A from the remaining lengths of web 30 not included within the periphery 14 and outside of ends 21 and 22.

Forced-air blanket 11A includes at least one inlet 16 that is arranged to receive a flow of air, and when receiving that flow of air, to inflate forced-air blanket 11A by providing the flow of air to the passageway 15. The linear seals 27 and the staked seals 28 tend to limit the distances between the upper layer 12 and the bottom layer 13 create within the passageways 15 between the liner seals and the between the staked seals. In various examples, the arrangement and number of linear seals and the arrangement and number of staked seals included within area 31 provides a forced-air blanket 11A having a low overall profiled, e.g., a relatively small maximum space, e.g., maximum thickness dimension, between the upper layer 12 and the bottom layer 13 within any of the passageways 15 when forced-air blanket 11A is inflated using a flow of air provided within a predetermine flow rate. In some examples, the predetermine flow rate is in a range of 15 to 60 cubic feet per minute (CFM) and in some examples is 45 CFM. In some embodiments, source 19 provides pressurized air at a flow rate of 40 to 50 cubic feet per minute (CFM). In some cases, source 19 provides pressurized air at a flow rate of 35 to 60 CFM. In some cases, source 19 provides pressurized air at a flow rate of 40 to 60 CFM. When provided with a flow of air that is within the predetermined flow rate, forced-air blanket 11A is configured to have a maximum thickness dimension in a range of 3 to 15 inches between the upper layer 12 and the bottom layer 13 within any portion of the passageways 15.

Various processes may be used to form the bond provided a periphery 14, to provide cutouts 23, 24, and to provide linear seals 27, and stake seals 28 within the area 31 enclosed by periphery 14. Examples of processes that may be use to bond upper layer 12 to bottom layer 13 along periphery 14 includes ultrasonic welding, radio frequency welding, heat sealing, or the like. These same processes may be use to form linear seals 27 and/or staked seals 28. In some examples, periphery 14, linear seals 27, and stakes seals 28 may be formed as part of a single process, e.g., all at the same time using a same process or technique. In other examples, one or more different process, performed at a same or at different times on web 30, may be used to form periphery 14, linear seals 27, and/or staked seals 28. In addition, the band 32 of openings provided in at least bottom layer 13 may by be generated in the material used to form bottom layer 13 in a process performed before or as the layer used to form upper layer 12 and bottom layer 13 are brought together to form web 30. In examples where both upper layer 12 and bottom layer 13 are to be provided with openings, the preformation process may be performed after the material providing upper layer 12 and bottom layer 13 have been brought together to form web 30.

As shown in FIG. 2A, forced-air blanket 11A may optionally include a sealed additional opening 17. Opening 17 may be opening 17 as illustrated and desired above with respect to FIG. 1, and may include any of the features and provide any of the functions described with respect to opening 17 and FIG. 1. The process of affixing an inlet 16 and/or an additional opening 17 to the layers 12, 13 provided as web 30 may be performed either before or after the portion of web 30 is processed to form periphery 14, linear seals 25, and/or staked seals 28.

Figure 2B:
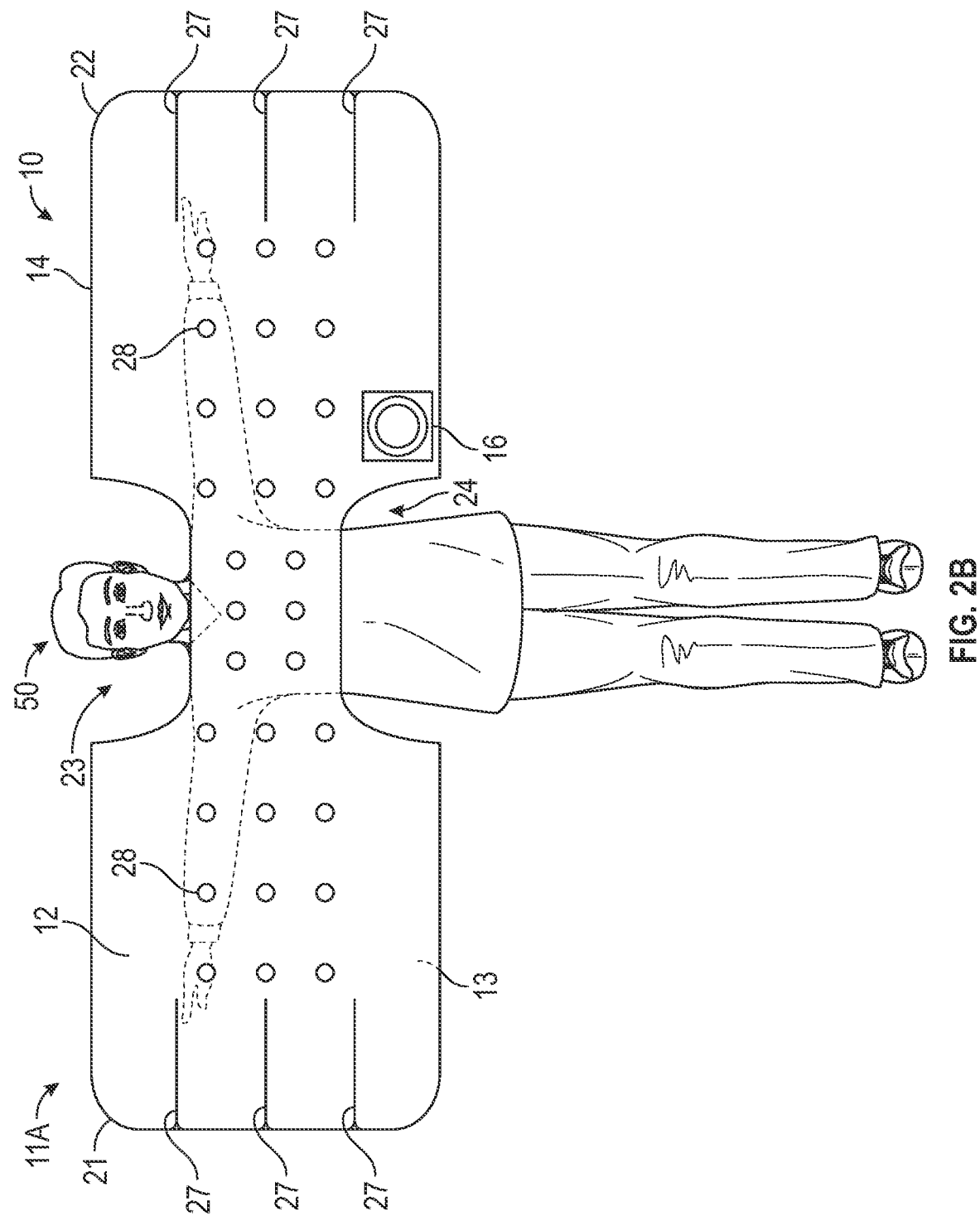
FIG. 2B illustrates the forced-air blanket of FIG. 2A overlaying a patient as part of a system in accordance with various implementations and techniques described in this disclosure.

FIG. 2B illustrates the forced-air blanket 11A of FIG. 2A overlaying a patient 50 as part of system 10 described in FIG. 1 in accordance with various implementations and techniques described in this disclosure. As illustrated in FIG. 2B, the central portion of forced-air blanket 11A between cutouts 23, 24 is laid over the upper torso of patient 50, and ends 21, 22, extend away from the central portion in opposite directions to cover the arms, respectively, of patient 50. Forced-air blanket 11A includes both linear seals 27 and staked seals 28 holding upper layer 12 in relatively close proximity to bottom layer 13 over the area of upper layer 12 and bottom layer 13 enclosed within perimeter 14. In addition, at least bottom layer 13 is perforated with a band of openings, as illustrated and described above with respect to band 32, the openings arranged to allow a profusion of air to pass through bottom layer 13 and be provided to patient 50. The arrangement of linear seals 27 and staked seals 28 provides forced-air blanket 11A with a low profile, and described above, when inflated by a flow of air received at inlet 16, for example by a flow of air provided by source 19 as shown in FIG. 1. The forced-air blanket 11A also provides a level of drapability, for example with respect to ends 21, 23 relative to the central portion of the forced-air blanket between cutouts 23 and 24 that allow the forced-air blanket to drape from each side of the torso of the patient 50 so as to provide better contact and/or warming functions for both the torso and the arms of patient 50.

Figure 2C:
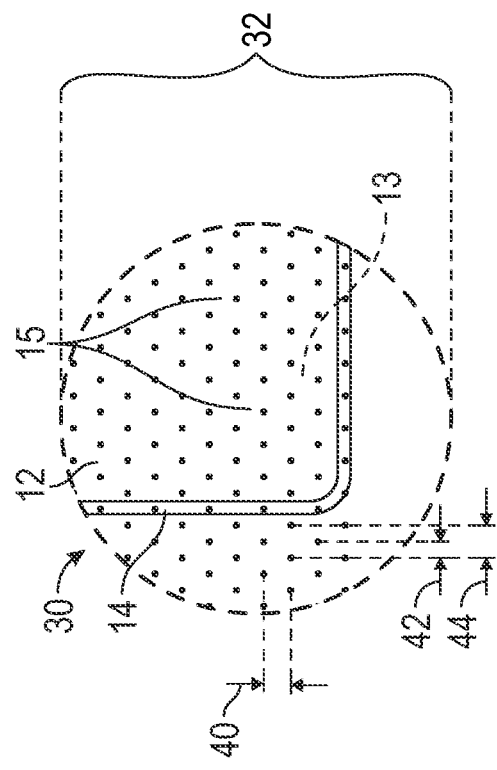
FIG. 2C illustrates a detail view of a web including a corner section of a forced-air blanket in accordance with various implementations and techniques described in this disclosure.

FIG. 2C illustrates a detail view C of web 30 including a corner section of forced-air blanket 11A of FIG. 2A in accordance with various implementations and techniques described in this disclosure. As illustrated in FIG. 2C, detail C provides a top view of a corner of forced-air blanket 11A having upper layer 12 and bottom layer 13 sealingly bonded along a portion of periphery 14. At least the bottom layer 13 is perforated with a plurality of openings illustratively represented by band 32. In various example, the band 32 of openings includes rows of openings spaced apart by a vertical distance 40 in a range 3 to 20 mm, typically about 12 mm apart. The columns of openings within any given row may be staggered so that the horizontal distance 42 between openings in any given row above and below another row is in a range of 1 to 11 mm, typically about 6 mm, and the spacing between openings within a given row has a horizontal distance 44 is in a range of 3 to 20, typically about 12 mm.

Figure 2D:
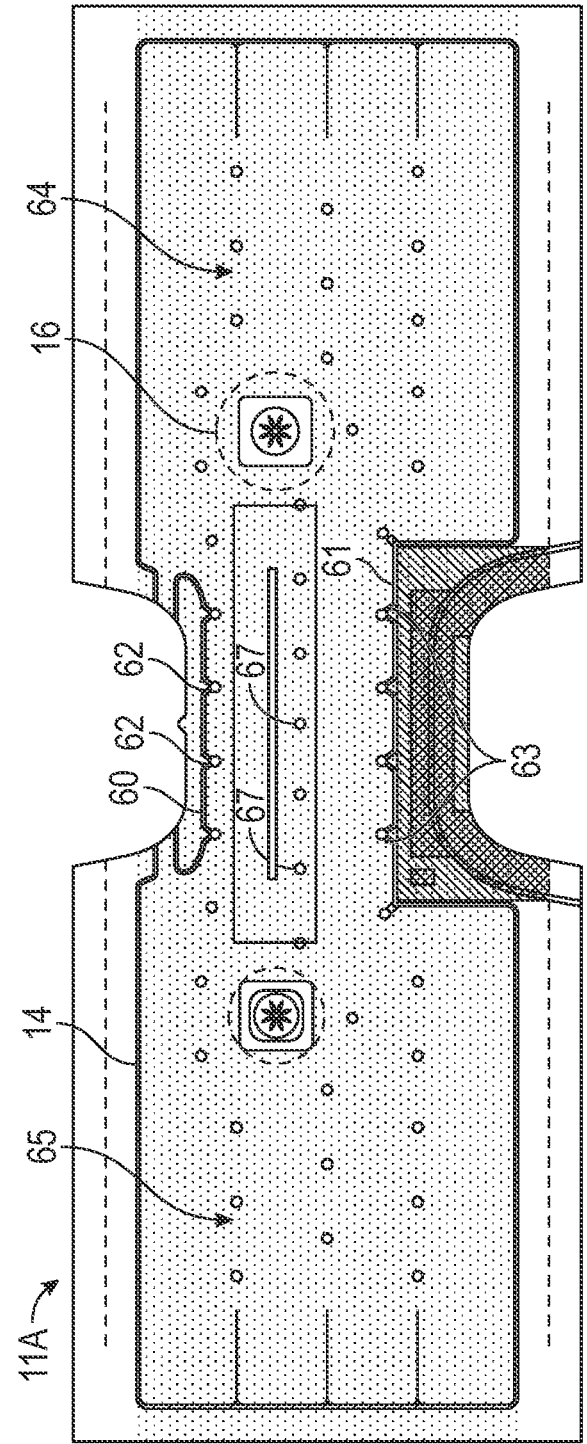
FIG. 2D illustrates further details of examples of warming blanket 11A of FIG. 2A.

FIG. 2D illustrates further details of examples of warming blanket 11A of FIG. 2A. As shown in FIG. 2D, warming blanket 11A includes two sets of air-guide elements 60 and 61, where each set of air-guide elements forming an air-guide device are disposed proximate to cutout 23 and cutout 24, respectively. In some examples, the air-guide element 60 includes one or more sets of air-guide elements 62 disposed in a pattern. In some cases, a set of air-guide elements 62 can be disposed with equal spacing. In some cases, a set of air-guide elements 62 are disposed no more than one centimeter from the periphery seal forming air-guide device 60. In some cases, a set of air-guide elements 62 are disposed no more than one inch (2.54 cm) from the periphery seal forming air guide device 60. In some cases, a set of air-guide elements 62 are disposed no more than two inches (5.08 cm) from the periphery seal forming air guide device 60. In some examples, the air-guide elements 62 contact and/or are formed as part of the periphery seal forming air-guide 60. In some examples, air-guide elements 62 are staked seals 28 as described above.

Similarly, the air-guide device 61 includes one or more sets of air-guide elements 63 disposed in a pattern. In some cases, a set of air-guide elements 63 can be disposed with equal spacing. In some cases, a set of air-guide elements 63 are disposed no more than one centimeter from the periphery seal forming air-guide device 61. In some cases, a set of air-guide elements 63 are disposed no more than one inch (2.54 cm) from the periphery seal forming air guide device 61. In some cases, a set of air-guide elements 63 are disposed no more than two inches (5.08 cm) from the periphery seal forming air guide device 61. In some examples, the air-guide elements 63 contact and/or are formed as part of the periphery seal forming air-guide device 61. In some examples, air-guide elements 62 are staked seals 28 as described above.

In some cases, warming blanket 11A includes three sets of air-guide elements 62, 63, and 67 disposed in a staggered pattern of rows relative to each other. In some examples, air-guide elements 67 comprised staked seals 28 as described above.

In some cases, the sets of air-guide elements 60 and 61 and 67 are disposed between the first portion 64 and the second portion 65 of the blanket 11A, and is to direct flow of inflation medium received at inlet 16 between the two portions, especially when the first portion 64 and/or the second portion 65 are bent. In some cases, the air-guide elements 60 and 61 and 67 are disposed in the inflatable channel 15 connecting the first portion 64 and the second portion 65. As used herein, "in an inflatable channel" or "within an inflatable channel" includes partially within the inflatable channel. In some cases, the air-guide elements 60 and 61 and 67 are configured to facilitate forming creases at the edge of the air-guide device when warming blanket 11A is inflated and at least one of the first portion 64 and the second portion 65 are rearranged such that part of the warming blanket 11A is bent (e.g., as illustrated for example in FIGS. 4C-4F). Various additional examples of air-guide devices and air-guide elements are illustrated and described in International Application Publication Number WO 2016/105462 A1 published 30 Jun. 2016, and is incorporated by reference in this disclosure in its entirety.

Figure 3:
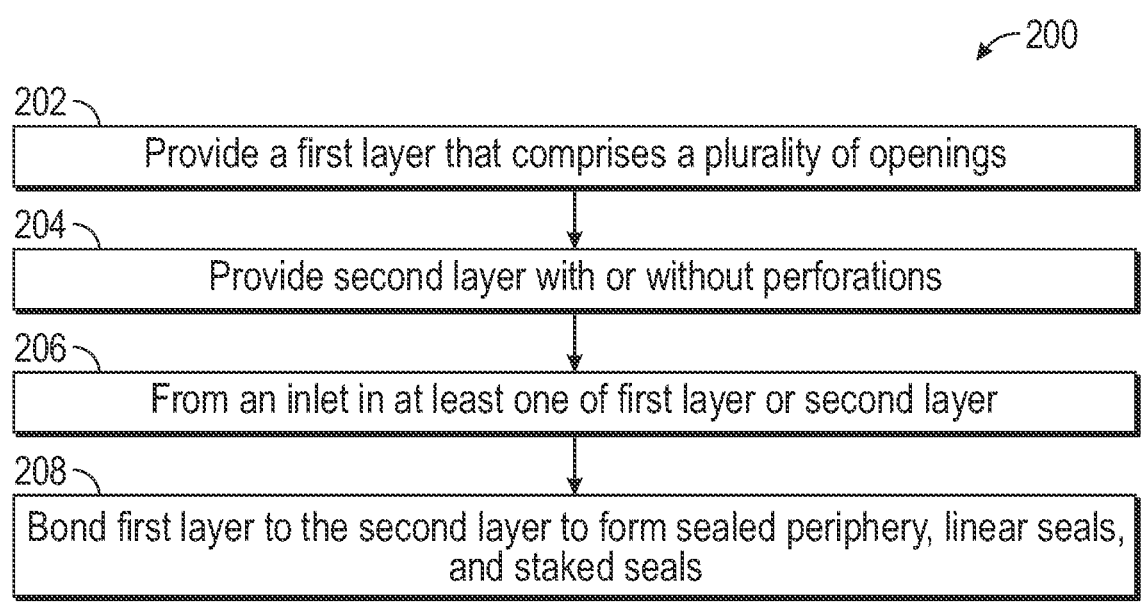
FIG. 3 is a flowchart illustrating a method in accordance with example implementations and techniques described in this disclosure.

FIG. 3 illustrates a method 200 in accordance with example implementations and techniques described in this disclosure. Method 200 is described with respect to forced-air blanket 11A as described for example in FIG. 2A-2C of the disclosure, but is not limited to any particular system or any particular forced-air blanket, and may be performed with respect to any examples of forced-air blankets described in this disclosure, and the equivalents thereof. Method 200 includes forming a forced-air blanket 11A, wherein the method 200 includes to provide a web of a first layer of a forced-air blanket that comprises a plurality of openings perforating the at least one layer, the openings configured to allow profusion of a flow of air to pass through the at least one layer (block 202). In some examples, the at least one layer is the bottom layer 13 of forced-air blanket 11A. Method 200 further includes to provide a web of a second layer of a forced-air blanket that may or may not comprise a plurality of openings perforating the at second layer, the openings configured to allow profusion of a flow of air to pass through the second layer (block 204). In some examples the second layer is the upper layer 12, and the upper layer 12 also includes a plurality of openings that are arranged to allow a profusion of the flow of air to pass through the upper layer 12.

Method 200 further includes to form an inlet 16 in at least one of the first layer web or the second layer web (block 206). Method 200 further includes to bond the at least one layer to the second layer along a periphery 14 to form an air seal along a periphery 14 and enclosing an area 31 and to form at least one linear seal 27 (block 208). In various examples, method 200 includes forming both linear seals 27 and staked seals 27 within the area 31 enclosed by perimeter 14. In some examples, only linear seals 27 are formed within the area 31 enclosed by perimeter 14. In various examples, the process used to bond the first layer to the second layer to form the linear seal includes use of ultrasonic welding, radio frequency welding, heat sealing, or the like. In various examples, the process used to bond the at least one layer to the second layer to form the staked seal includes use of an ultrasonic welding, radio frequency welding, heat sealing, or the like.

As further described below, examples of warming blanket 11 and 11A, and the equivalents and variations thereof, have at least a portion of the warming blanket that comprise a material or materials that allow the warming blanket to be deformed, for examples stretched along various dimensions corresponding to generally planar dimensions, in order to reshape the warming blanket into a shape that is different from the initial shape and configuration of the warming blanket prior to inflation of the blanket. However, in various examples, deformation of the warming blanket can occur either before or after the warming blanket is inflated with a flow of air, such as a flow of air provided at inlet 16 by source 19. In various examples, deformation of the warming blanket to reshape the warming blanket includes plastic deformation of at least apportion of the warming blanket such that once deformed, the warming blanket tends to maintain the shape that the blanket was reformed to take on. In other examples, deformation of the warming blanket to reshape the warming blanket includes elastic deformation of a least a portion of the warming blanket, such that once elastically deformed, the portion of the warming blanket deformed may be returned to substantially the initial configuration of the warming blanket before the warming blanket was elastically deformed. In various examples, the warming blanket includes one or more securing ties (not shown in FIG. 1, but for example securing tie 56 as shown and described with respect to FIG. 4E, and securing tie 74 as shown and described with respect to FIG. 5), which help maintain the deformed warming blanket in the reconfigured shape once the blanket has been deformed.

In various examples, the material or materials that comprise the portions or portions of the warming blanket that are deformable include materials that can be formed as films used to form upper layer 12, bottom layer 13, both layers 13, 14, and/or any portions thereof. Examples of materials that deform include very low density polyolefins, low density polyethylene, linear low density polyethylene, polypropylene, and olefin copolymers such as ethylene-vinyl acetate (EVA). A preferred plastically deforming material would be very low density polyethylene optionally containing fillers. Examples are metallocene polyolefin and parafilm. Examples of materials that are elastic are materials that include polyolefins, such as metallocene polyethylenes such as Engage® polyethylenes (commercially available from Dow Chemical Company, Midland Mich.), polyurethanes such as polyester or polyether polyurethanes (e.g., "Estane® thermoplastic polyurethane," commercially available from B. F. Goodrich, Cleveland Ohio), polyesters such as polyether polyester (e.g., "Hytrel® polyester elastomer," commercially available from Du Pont Co., Wilmington, Del.), and polyamides such as polyether polyamides (e.g., "Pebax® Resins" commercially available from ELF Atochem, North America, Inc., Philadelphia, Pa.) and acrylic block copolymers such as Kurarity block polyacrylates available from Kuraray America, Houston Tex. In various examples, the material forming the portion of blanket or the blanket itself that is deformable allows the material to be deformed by an elongation of at least 20% the blanket or of the deformable portion of the blanket. In some examples, the material forming the portion of blanket or the blanket itself that is deformable allows the material to be deformed by an elongation of at least 30% the blanket or of the deformable portion of the blanket. In other examples, the material forming the portion of blanket or the blanket itself that is deformable allows the material to be deformed by an elongation of at least 40% the blanket or of the deformable portion of the blanket. In other examples, the material forming the portion of blanket or the blanket itself that is deformable allows the material to be deformed by an elongation of at least 50% the blanket or of the deformable portion of the blanket. In various examples, the warming blanket is configured so that when a force of deformation applied is less than 25 Newtons at 25% strain for a test sample of the deformable portion of the blanket that is 2.54 cm wide, according to a tensile strength testing with a gauge length of 50 mm and cross-head speed (pull speed) of 254 mm per minute.

FIG. 4A illustrates a top view of various dimensional aspects and other characteristics of an example warming blanket 11A according to the techniques described in this disclosure. As illustrated, warming blanket 11A includes the features of warming blanket 11A illustrated and described with respect to FIG. 2A, including a periphery 14 coupling upper layer 12 and bottom layer 13, and providing an initial shape, including a width dimension W, and a longitudinal dimension L between ends 21 and 22, and a narrowed central portion midway along this longitudinal dimension, generally indicated by cutouts 23, 24. Longitudinal dimension L is some examples is in a range of 60 to 90 inches, and width dimension W may be in a range of 10 to 40 inches. Upper layer 12 and bottom layer 13 form passageways 15 that are coupled to receive a flow of air provided to inlet 16, and to distribute the air throughout passageways 15 to be expelled out through bottom layer 13.

As shown in FIG. 4A, upper layer 12 is sealed or otherwise in contact and bonded with bottom layer 13 at the periphery 14, and also at linear seals 27 and staked seals 28, to form passageways 15 between upper layer 12 and bottom layer 13. Bottom layer 13 includes a porous material, or may be a perforated non-porous material, having passages openings that allow a flow of air, generally indicated by arrows 20) to exit passageways 15 through bottom layer 13 when warming blanket 11A is provided a flow of air to passageways 15. Bottom layer 13 is generally a sheet of material having a planar configuration when lying on a horizontal rigid surface within periphery 14, and upper layer 12 is generally a sheet of material, having ridges formed by passageways 15, As further illustrated and described below, deformation of the warming blanket 11A to reshape the warming blanket may include deforming the blanket in at least one dimension to reshape the blanket, wherein a thickness dimension of the blanket after being deformed and inflated does not increase or decrease by more than 50% and preferably by not more than 25% in the same dimension of inflated thickness dimension, after deforming or reshaping the warming blanket with respect of the shape of periphery 14 to some extent, and while maintaining the integrity of the passageways 15 through the warming blanket. By "maintain the integrity of passageways" 15 it is meant that the entire blanket still inflates and preferably does so in less than 30 seconds, more preferably in less than 20 seconds and most preferably in less than 10 seconds when using a forced air blower at a pressure of 100 mmHg and a flow rate of 15 to 60 cubic feet per minute (CFM). In other words, deforming the warming blanket to reshape the periphery of the warming blanket while maintaining thickness dimension of +/−50% across the upper and bottom layers of the warming blanket may also not restrict the flow of air to the passageways 15, for example by kinking, crushing, or otherwise obstruction the passageways 15 and/or the airways coupling in the passageways to inlet 16 across substantially the entirety of the bottom surface 13 of the warming blanket. When deformed, the warming blanket 11A is configured to maintain the integrity of the passageways 15, and thus continue to be able to deliver substantially the same air flow in the deformed shape as would have been available when the warming blanket was in the un-deformed initial shape and configuration.

Warming blanket 11A includes a dimension 30A along the periphery 14 within cutout 23, and a dimension 32A along the periphery 14 within cutout 24. As shown in FIG. 2A, a typical dimension for dimension inset 30A and dimension inset 32A when warming blanket is in the initial configuration, as illustrated in FIG. 4A, is in a range of 12 to 24 inches. In various examples, at least the central portion warming blanket 11A, generally indicated by the portion of warming blanket included between dimension inset 30A and dimension inset 32A, includes a material or materials that are deformable to allow periphery 14 to be stretched or otherwise reshaped, while maintaining thickness dimension of the warming blanket to +/−50% of the original dimension, and while maintain the integrity of the passageways 15 throughout the warming blanket, including the portions of the passageways included in the central portion of the warming blanket. In various examples, pleats 54 may be provided along a portion of cutout 23 to allow expansion of upper layer 12, to aid in expanding dimension 30A along the outside curve of periphery 14 within cutout 23. Similar pleats may also be included on bottom layer 13. In addition, pleats 52 may be provided along a portion of cutout 24 to allow folding of upper layer 12, to aid in lessening dimension 32A along the inside curve of periphery 14 within cutout 24. Similar pleats may also be included on bottom layer 13.

As further described below, warming blanket 11A in the initial configuration including various axes, such as axes 33, 34, 35, and 37, that have an initial orientation when warming blanket is in the initial shape and configuration shown in FIG. 4A. For example, axis 33 includes an axis that aligns with the longitudinal dimension of the warming blanket 11A along periphery 14 and inside cutout 23, and axis 34 includes an axis that aligns with the longitudinal dimension of the warming blanket 11A along periphery 14 and inside cutout 24. Axis 35 includes an axis that aligns with the width dimension of the warming blanket 11A along periphery 14 at end 22, and axis 37 includes an axis that aligns with the longitudinal dimension of the warming blanket 11A along periphery 14 and along a side 36 of periphery 14 outside cutout 23.

Figure 4C:
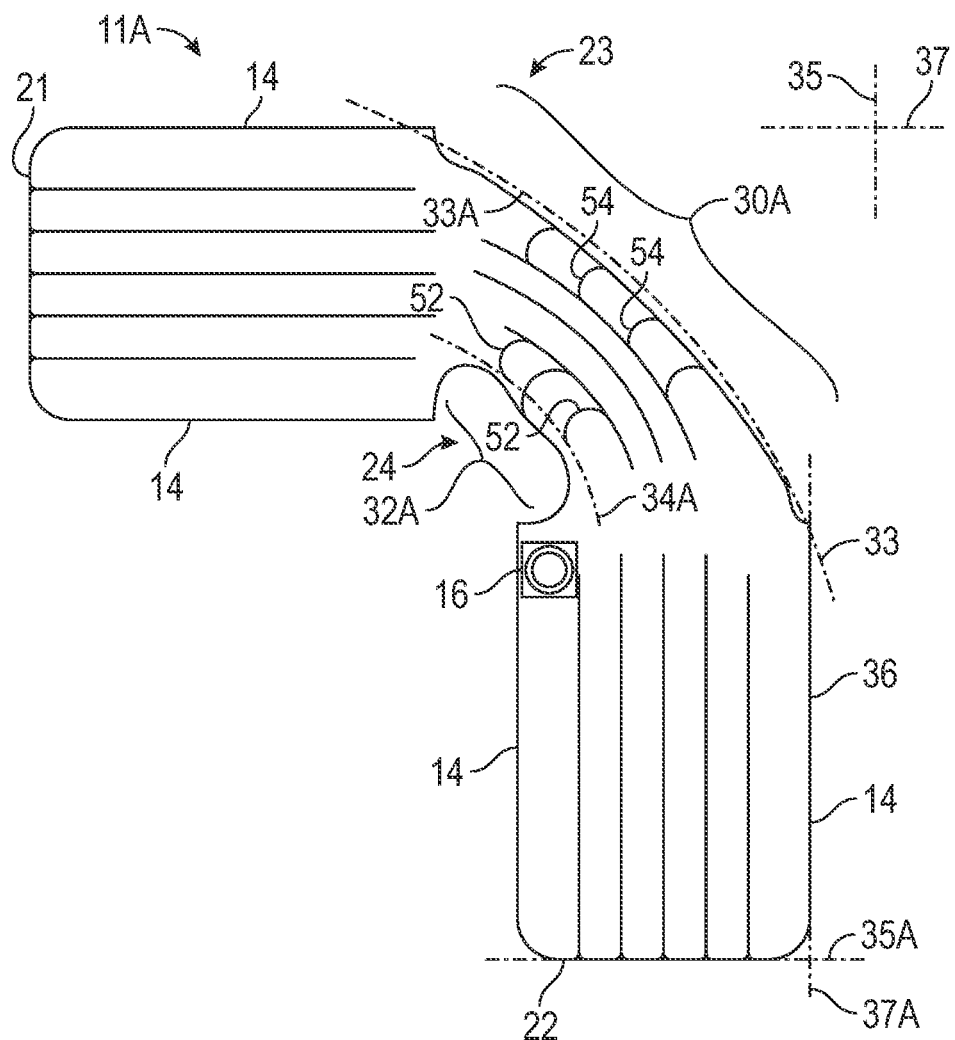
FIG. 4C illustrates a top view of the warming blanket that is deformed to reshape the warming blanket into a shape and configuration that is different from the initial shape and configuration.

Each of these axes lie in a plane that is coplanar with or in a plane that is parallel to the central plane of warming blanket 11A, for example when warming blanket 11A is lying on a rigid horizontal surface, and has an initial orientation (e.g., axis direction) as shown in FIG. 4A. As illustrated and described with respect to FIGS. 4A-4E, the orientation of one or more of these axes may be changed in a direction and/or in a dimension in order to reshape the periphery 14 of the warming blanket 11A, while the axes remain approximately coplanar or in a plane parallel to central plane 42 of the warming blanket, and while maintaining the integrity of the passageways 15. As would be understood by one of ordinary skill in the art, many other illustrative axes could be associated with the configuration of warming blanket 11A as shown in FIG. 4A, and are contemplated by the examples described herein.

FIG. 4B illustrates an example of a variation of the warming blanket 11A of FIG. 4A in accordance with one or more example implementations and techniques described in this disclosure. Warming blanket 11A as shown in FIG. 4B may include any combination of the features shown and described above with respect to warming blanket 11A or the equivalents thereof, with the variations as described below. As shown in FIG. 4B, the periphery warming blanket 11A within the cutout area 23 is formed to have a wavy or sinusoidal shape, as indicated by periphery 14A. In addition, the periphery of warming blanket 11A as shown in FIG. 4A may have a way or sinusoidal shape as indicated by periphery 14B. The shape of periphery 14A and 14B are limited to a particular shape, such as a sinusoidal shape, and may be any shape having a linear distance that when traced along periphery 14A, and/or 14B, have a linear distance that is greater than the linear distance for a straight line. In various examples, only periphery 14A or 14B is provided as a wavy or sinusoidal (e.g., non-linear) shape.

By providing the one or both of periphery 14A, 14B as a wavy, sinusoidal, or some other non-linear shape, the section including the periphery 14A, 14B provides a slack to the dimension 30A and or 32A to allow for stretching of that section of periphery. When periphery 14A or 14B is provided on as a periphery on a side of the warming blanket 11A that is opposite a side being stretched, the periphery 14A or 14B promotes controlled bending of that portion of the periphery. Either or both of periphery 14A, 14B may be provided in conjunction with pleats 54, 52, respectively, to further aid in and control the bending of warming blanket 11A in the portion of warming blanket 11A where at least one of periphery 14A, 14B are provided.

FIG. 4C illustrates a top view of the warming blanket 11A of FIG. 4A or 4B, deformed to reshape the warming blanket into a shape and configuration that is different from the initial shape and configuration. As illustrated, warming blanket 11A has been deformed so that the dimension indicated by dimension bracket 30A has been stretched to increase this dimension associated the periphery 14 within cutout 23, and the axis 33 along this same portion of periphery 14 has been re-oriented from a straight line to form an arc shape, illustrated as axis 33A. In addition, the axis 34 that was originally a straight line along periphery 14 within cutout 24 is also re-oriented, may include for example in some embodiments an arc shape as illustrated by axis 34A, and the dimension associated with dimension bracket 32A is compressed to have a smaller dimensional value. As illustrated in FIG. 4C, axis 35, that originally aligned with end 22 of the warming blanket has been re-oriented approximately 90-degrees, as represented by axis 35A. Similarly, axis 37, which originally aligned with side 36 of warming blanket 11A, is re-oriented approximately 90 degrees, as represented by axis 37A. In all instance of re-orientation of axes 33, 34, 35, and 37, the direction and dimension associated with the re-orientation of these axes is coplanar or is contained within a plane that is parallel to central plane 42 of warming blanket 11A. As such, the overall thickness of warming blanket 11A may remain substantially the same dimensionally (e.g. +/−25%) and substantially over the entirety of upper layer 12 and the bottom layer 13 of the warming blanket.

This feature allows the warming blanket 11A to be deformed and reshaped as shown in FIG. 4C, while the integrity of the passage ways 15 is maintained throughout the warming blanket. This feature may be important as it allows the reshaped warming blanket to be placed over a patient while keeping the bottom layer of the warming blanket proximate to and/or in contact with the patient across the portion of the warming blanket positioned proximate to the patient, thus may provide more efficient warming of the patient. In addition, as shown in FIG. 4C the integrity of the passage ways 15 is maintained throughout the warming blanket, including in the areas between cutouts 23 and 24 where the warming blanket has been deformed to reshape the warming blanket.

In various examples, pleats 54 may be provided along a portion of cutout 23 to allow expansion of upper layer 12, to aid in expanding dimension 30A along the outside curve of periphery 14 within cutout 23. Similar pleats may also be included on bottom layer 13. In addition, pleats 52 may be provided along a portion of cutout 24 to allow folding of upper layer 12, to aid in lessening dimension 32A along the inside curve of periphery 14 within cutout 24. Similar pleats may also be included on bottom layer 13.

Figure 4D:
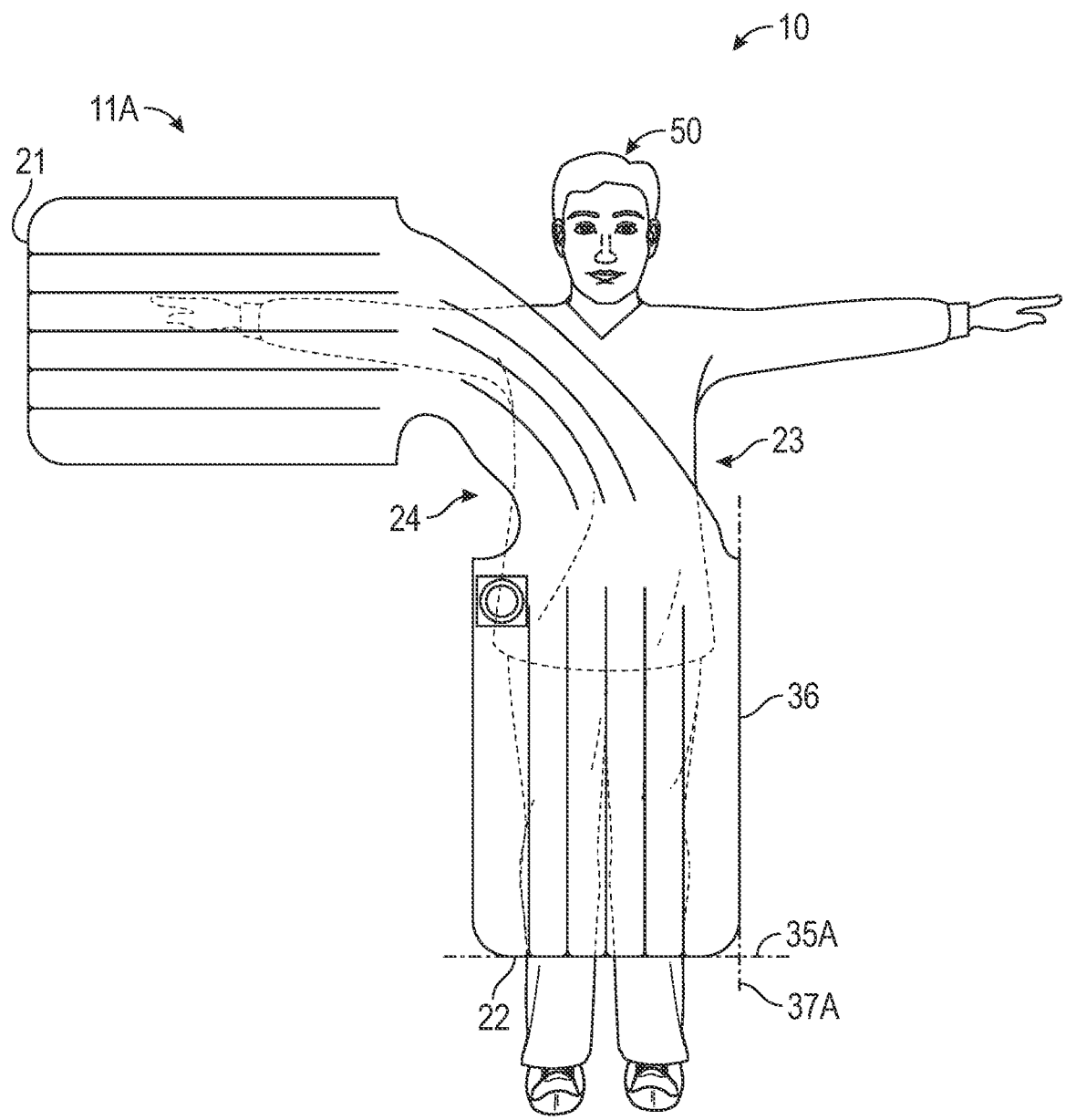
FIG. 4D illustrates an example warming system including a warming blanket of FIG. 4C in accordance with one or more example implementations and techniques described in this disclosure.

FIG. 4D illustrates an example warming system 10 including a forced air warming blanket 11A of FIG. 4C in accordance with one or more example implementations and techniques described in this disclosure. As illustrated, warming blanket 11A is shown in a reshaped configuration as illustrated and described for example with respect to FIG. 4C, now having end 22 rotated approximately 90-degrees relative to the position of end 22 when warming blanket was in the initial configuration. As shown, the portion of warming blanket 11A including the central portion is located over the lower torso of patient 50, with the portion of the warming blanket including end 21 extending over one arm of the patient, and the portion of the warming blanket including end 22 extending over the legs of patient 50. As illustrated in FIG. 4D, axes 33, 34, 35, and 36 are re-oriented from an initial configuration to be oriented in the same orientations as illustrated and described above with respect to FIG. 4C. By reshaping warming blanket 11A as shown in FIG. 4D, the warming blanket 11A can now be applied as shown in FIG. 4D by simply deforming at least the central portion of the warming blanket.

Figure 4E:
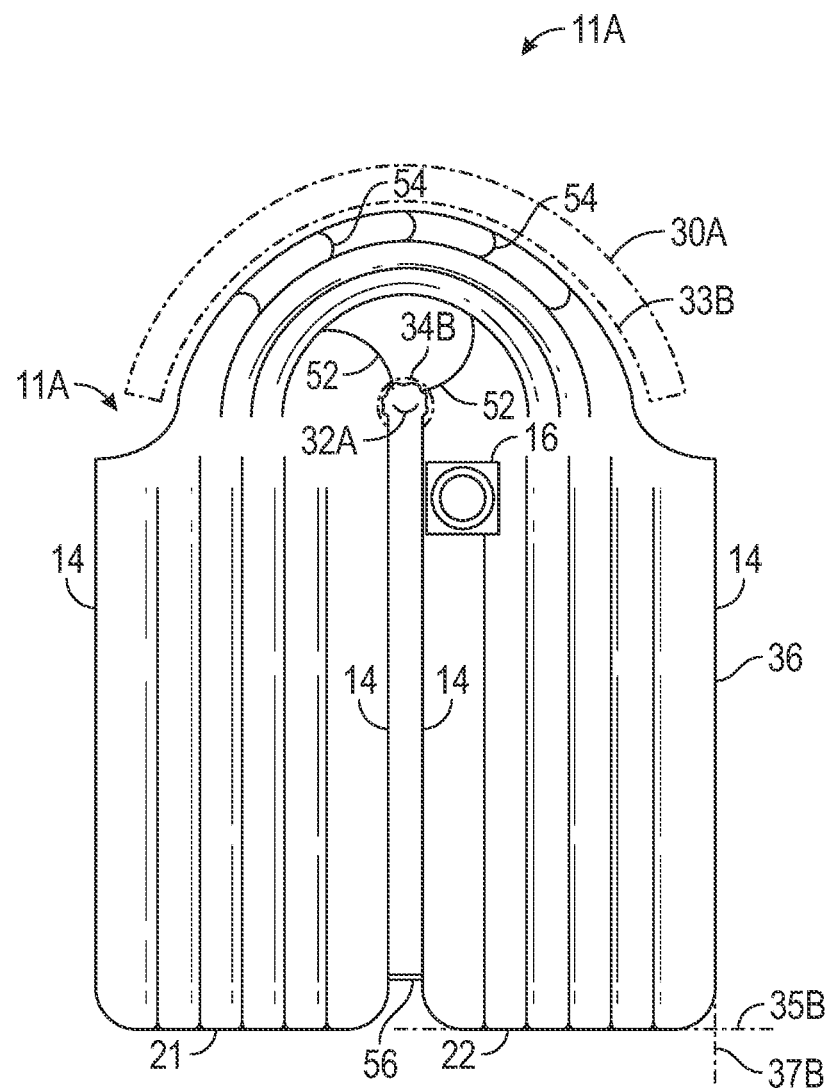
FIG. 4E illustrates a top view of the warming blanket of FIG. 4C, further deformed to reshape the warming blanket into a shape and configuration that is different from the initial shape and configuration, and that is different from the deformed shape and configuration illustrated in FIG. 4C.

FIG. 4E illustrates a top view of the warming blanket 11A of FIG. 4C, further deformed to reshape the warming blanket into a shape and configuration that is different from the initial shape and configuration, and that is different from the deformed shape and configuration of the warming blanket illustrated in FIG. 4C. As illustrated in FIG. 4E, warming blanket 11A has been deformed so that the dimension indicated by dimension bracket 30A has been stretched to increase this dimension associated the periphery 14 within cutout 23, and the axis 33 along this same portion of periphery 14 has been re-oriented from a straight line to form an arc shape, illustrated as axis 33B. The axis 34 that was originally a straight line along periphery 14 within cutout 24 is also re-oriented, including an arc shape as illustrated by axis 34B, and the dimension associated with dimension bracket 32A is compressed to have a smaller dimension relative to the dimension of dimension bracket 32A relative to this dimension in the initial configuration.

As illustrated in FIG. 4E, axis 35, that originally aligned with end 22 of the warming blanket has been re-oriented approximately 180-degrees, as represented by axis 35B. As illustrated, end 22 aligns with end 21 of warming blanket 11A. Similarly, axis 37, which originally aligned with side 36 of warming blanket 11A, is re-oriented approximately 180-degrees from the orientation of this axis in the initial configuration, as represented by axis 37B in FIG. 4A. In all instance of re-orientation of axes 33, 34, 35, and 37, the direction and dimension associated with the re-orientation is approximately coplanar or is contained within a plane that is parallel to central plane 42 of warming blanket 11A. As such, the overall thickness of warming blanket 11A remains substantially the same dimensionally (+/−10%) over substantially the entirety of upper layer 12 and the bottom layer 13 of the warming blanket. Thus, the initial upper body warming blanket was transformed to a lower body blanket.

Again, this feature allows the warming blanket 11A to be deformed and reshaped as shown in FIG. 4E, while remaining substantially flat across the upper and bottom surfaces of the warming blanket. This feature may be important as it allows the reshaped warming blanket to be placed over a patient while keeping the bottom surface of the warming blanket proximate to and/or in contact with the patient across the portion of the warming blanket positioned proximate to the patient, and thus may provide more efficient warming of the patient. This is most easily confirmed by inflating the blanket in the original configuration on a rigid horizontal surface and reshaping the blanket to the second configuration while maintaining the same air flow and pressure. Preferred blankets lay flat on the surface in both configurations. In addition, as shown in FIG. 4E the integrity of the passageways 15 is maintained throughout the warming blanket, including in the areas between cutouts 23 and 24 where the warming blanket has been deformed to reshape the warming blanket.

In various examples, pleats 54 may be provided along a portion of cutout 23 to allow expansion of upper layer 12, to aid in expanding dimension 30A along the outside curve of periphery 14 within cutout 23. Similar pleats may also be included on bottom layer 13. In addition, pleats 52 may be provided along a portion of cutout 24 to allow folding of upper layer 12, to aid in lessening dimension 32A along the inside curve of periphery 14 within cutout 24. Similar pleats may also be included on bottom layer 13. In addition, warming blanket 11A may include one or more secure ties, such as a plastic strip illustrative shown as secure tie 56. Secure tie may be formed, for example, as part of upper layer 12 or as part of bottom layer 13, and extend from one or both of ends 21, 22. When warming blanket 11A has been reshaped as illustrated in FIG. 4E, secure tie 56 may be fastened between ends 21 and 22, for example by being tied to leads form both ends, to helps secure ends 21 and 22 in the position illustrated in FIG. 4E.

Figure 4F:
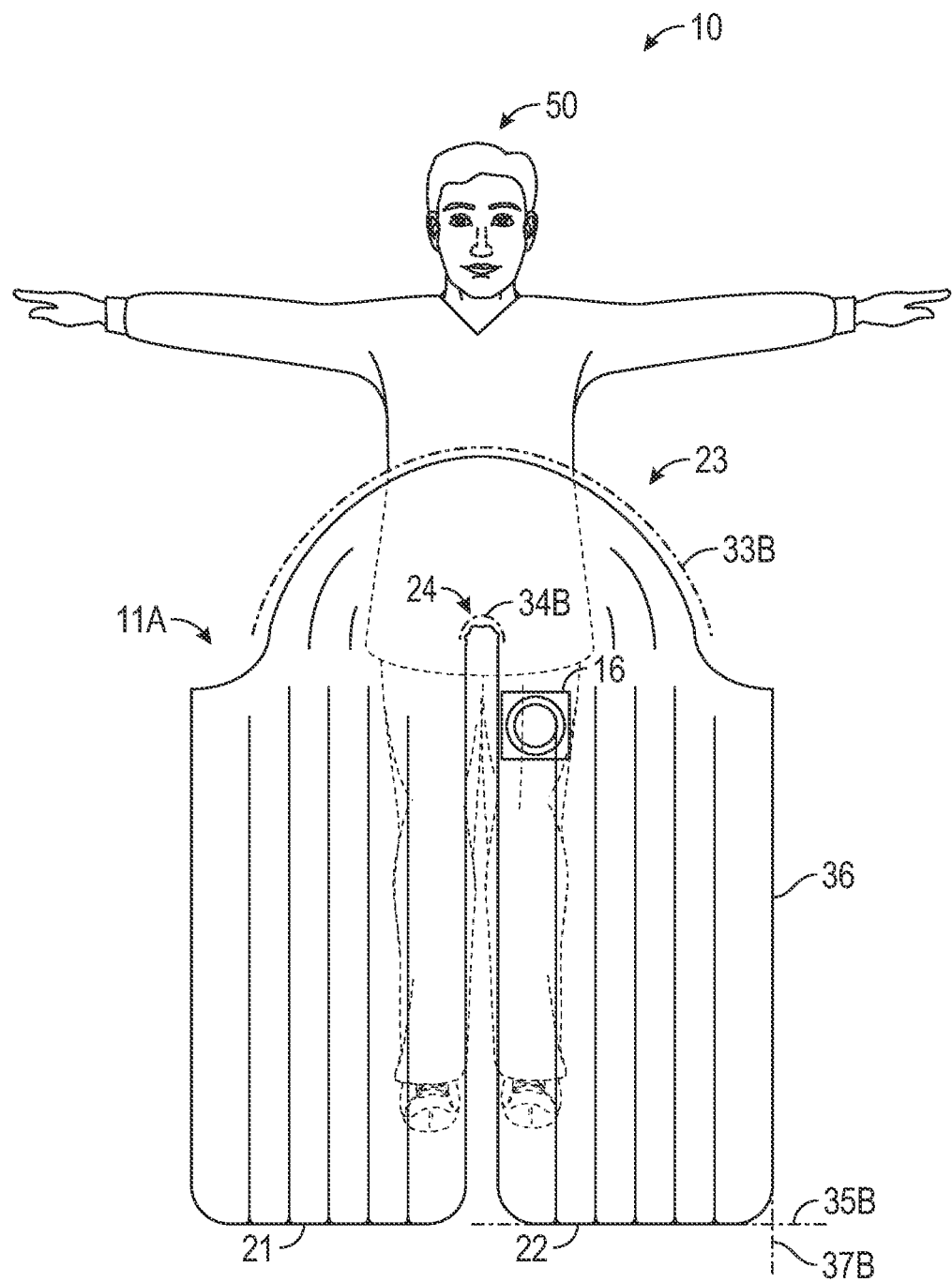
FIG. 4F illustrates an example warming system including a warming blanket of FIG. 4E in accordance with one or more example implementations and techniques described in this disclosure.

FIG. 4F illustrates an example warming system 10 including a forced air warming blanket 11A of FIG. 4E in accordance with one or more example implementations and techniques described in this disclosure. As illustrated, warming blanket 11A is shown in a reshaped configuration as illustrated and described for example with respect to FIG. 4E, now having end 22 rotated approximately 180-degrees relative to the position of end 22 when warming blanket is in the initial configuration. As shown, the portion of warming blanket 11A including the central portion is located over the lower torso, and the portions extending toward ends 21, 22 are positioned to cover both legs of patient 50. As illustrated in FIG. 4F, axes 33B, 34B, 35B, and 36B are re-oriented from an initial configuration to be oriented in the same orientations as illustrated and described above with respect to FIG. 4A. By reshaping warming blanket 11A as shown in FIG. 4F, the warming blanket 11A can now be applied as shown in FIG. 4F by simply deforming at least the central portion of the warming blanket.

FIG. 5 illustrates a top view of an example warming blanket 11A according to the techniques described in this disclosure. As illustrated in FIG. 5, one or more folded pleats, generally indicated by reference number 70, are provided along the periphery 14 of cutout 23. Folded pleats 70 include a fold 72 of the material having upper layer 12 folded over itself, and tacked or otherwise detachably secured along line 71 to the upper layer 12. When secured as shown, folded pleats 70 secure the periphery 14 along and within cutout 23. In order to allow for further expansion of the dimension along periphery 14 within cutout 23, one or more of lines 71 may be detached from the upper layer 12, allowing fold 72 to unfold, and expand the length dimension of periphery 14 within cutout 23. This feature may also be provided on the periphery 14 within cutout 24. Folded pleats 70 allow for deforming and reshaping of a portion of warming blanket 11A without, or in conjunction with, stretching the material or materials used to form the portion of warming blanket that can be deformed to reshape the warming blanket. Additionally, in some embodiments an aluminum wire or other strip or wire of malleable material may be included near the periphery 14 within cutout 24 proximate the lessening dimension 32A, to help retain the reshaped warming blanket in re-oriented configuration. Warming blanket 11A as shown in FIG. 5 includes at least one input 16 as described above. The warming blanket 11A as illustrated in FIG. 5 may optionally include an opening 17 according to any of the examples of opening 17 described in this disclosure, and the equivalents thereof.

As also illustrated in FIG. 5, various example of warming blanket 11A may include secure tie 74. Secure tie may be a strip of material that is secured to or within the upper layer 12 near periphery 14 of cutout 24. Secure tie 74 may have a first end 75 at one end of secure tie 74, and a second end 76 at the opposite end of the secure tie, wherein ends 75, 76 may be detachably secured to the external surface of upper layer 12. In various examples, when the warming blanket 11A is being reshaped so that the dimension of periphery 14 within cutout 24 is being reduced, for example as shown in FIG. 3A and FIG. 4A, the ends 75, 76 of secure tie 74 may be drawn together and fastened in a manner that helps compress the periphery 14 and the dimension of the periphery 14 within cutout 24, thus helping maintain warming blanket 11A in the a deformed and reshaped configuration. In various examples, secure tie 74 includes an elastic material configured to contract and help compress the periphery 14 and the dimension of the periphery 14 within cutout 24 when warming blanket 11A is being reshaped in a manner that compresses or tends to reduce the dimension of periphery 14 within cutout 24. One or more of the features and/or functions illustrated and described for the warming blanket 11A as illustrated in FIG. 5 may be incorporated, where appropriate, into any of the examples of warming blankets described in this disclosure.

Examples of warming blankets described herein are not limited to having a particular shape defined by the periphery of the warming blanket as an initial shape and configuration for the warming blanket. Examples of warming blanket 11A provided in FIGS. 1, 2A-2B, 4A-4F, and 5 are illustrative of a rectangular shaped warming blanket with cutouts that reduce the width dimension over a central portion of the warming blanket. However, other shapes, such as but not limited to rectangular shapes without cutouts, square shapes, and elliptical shapes are examples of other possible shaped for the periphery of a warming blanket and are contemplated by the examples provided in this disclosure.

FIG. 6 is an example of a rectangular warming blanket 11A having a porous or non-porous upper layer 12, a porous or perforated bottom layer 13, and a periphery 14 forming an initial shape of a rectangle without cutouts, and including one or more inlets such as an inlet 16 configured to receive an air flow that may be provided to the passageways 15 of the warming blanket. Warming blanket 11A includes a longitudinal axis L1 and a width axis W1. Warming blanket includes at least some portion of the warming blanket that is comprised of material or material that are deformable, either via plastic or elastic deformation, to allow warming blanket 11A to be reshaped so the periphery 14 has a different shape than periphery 14 formed while warming blanket 11A was in the initial configuration. Deformation may include re-orientation of one or both of axes L1 and W1, and wherein after being deformed to reshape warming blanket 11A, the warming blanket remains within an area defined by a thickness dimension of the warming blanket in the initial configuration when reshaped to form the new and different shape and configuration. One or more of the features and/or functions illustrated and described for the warming blanket 11A as illustrated in FIG. 6 may be incorporated, where appropriate, into any of the examples of warming blankets described in this disclosure.

Figure 7:
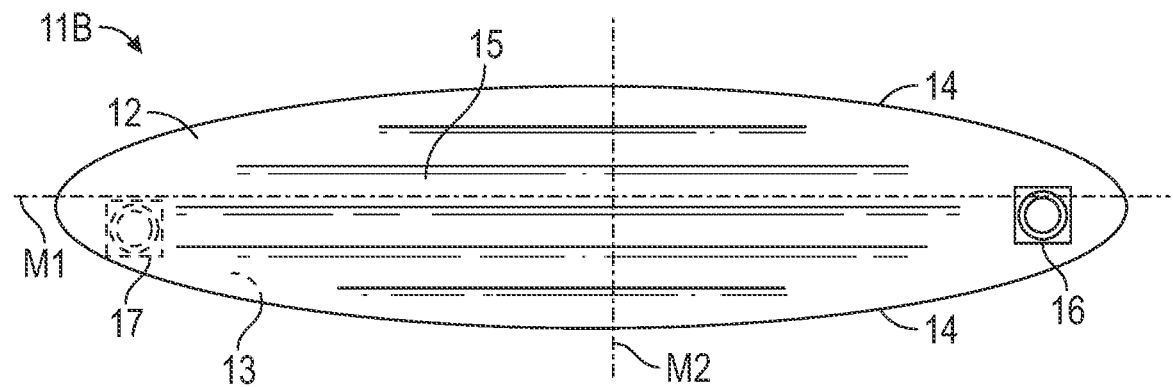
FIG. 7 is an example of an elliptically shaped warming blanket according to the techniques described in this disclosure.

FIG. 7 is an example of an elliptically shaped warming blanket 11B having a non-porous upper layer 12, a porous or perforated bottom layer 13, and a periphery 14 forming an initial configuration having a shape of an ellipse. Warming blanket 11B includes a major axis M1 and a minor axis M2. Warming blanket 11B includes at least some portion of the warming blanket that is comprised of material or material that are deformable, either via plastic or elastic deformation, to allow warming blanket 11B to be reshaped so the periphery 14 has a different shape than formed by periphery 14 while warming blanket 11B was in the initial configuration. Deformation may include re-orientation of one or both of axes M1 and M2, and wherein after being deformed to reshape warming blanket 11B, the warming blanket remains within an area defined by a thickness dimension of the warming blanket in the initial configuration when reshaped to form the new and different shape and configuration. One or more of the features and/or functions illustrated and described for the warming blanket 11B as illustrated in FIG. 7 may be incorporated, where appropriate, into any of the examples of warming blankets described in this disclosure.

Figure 8:
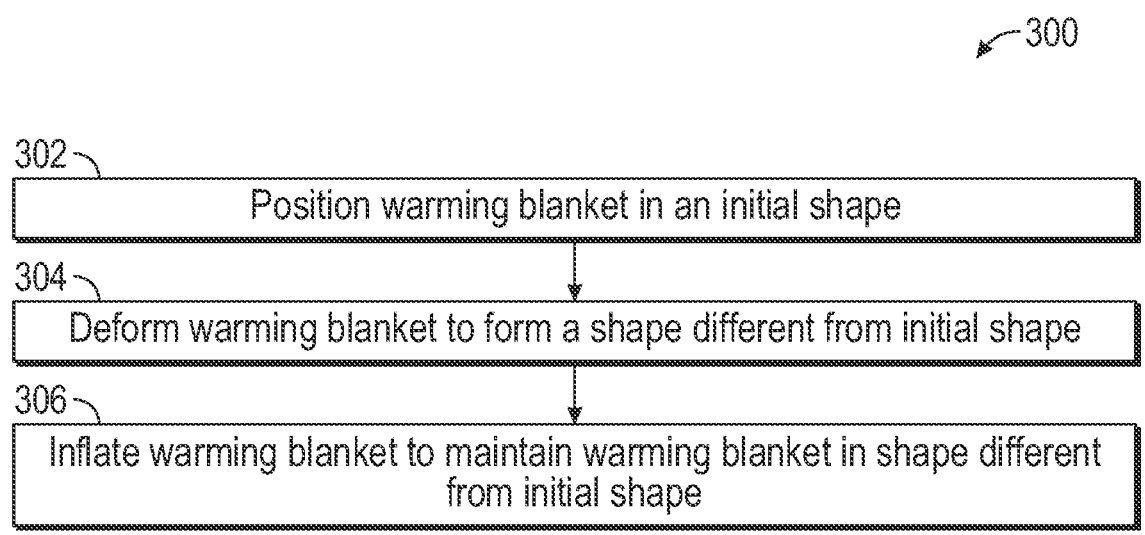
FIG. 8 is a flowchart illustrating a method according to various examples is accordance with the devices, systems, and techniques described in this disclosure.

FIG. 8 illustrates a method 300 according to various examples is accordance with the devices, systems, and techniques described in this disclosure. Method 300 is described with respect to system 10 and warming blanket 11 as described for example in FIG. 1 of the disclosure, but is not limited to any particular system or any particular warming blanket, and may be performed with respect to any examples of warming blankets described in this disclosure, and the equivalents thereof. According to method 300, warming blanket 11 is positioned in an initial shape (block 302). The initial shape may be formed with respect to a shape provided by a periphery, such as periphery 14, of the warming blanket. In the initial position, warming blanket may be placed on a substantially flat planar surface, so that the periphery 14 of warming blanket 11 is provided an initial shape having periphery coplanar to the flat planar surface.

According to method 300, the warming blanket includes at least a portion of the warming blanket that comprises a material or materials that are deformable, either through plastic and/or elastic deformation. Examples of materials that deform include very low density, low density, and linear low density polyolefins, metallocene polyolefins and olefin copolymers such as ethylene-vinyl acetate (EVA). In some examples, the material would be very low density polyethylene optionally containing fillers. An example is Parafilm™ M available from the Bemis Company, Oshkosh Wis. Examples of materials that are elastic are materials that include polyolefins, such as metallocene polyolefins and particularly metallocene polyethylenes such as Engage® polyethylenes (commercially available from Dow Chemical Company, Midland Mich.), polyurethanes such as polyester or polyether polyurethanes (e.g., "Estane® thermoplastic polyurethane," commercially available from B. F. Goodrich, Cleveland Ohio), polyesters such as polyether polyester (e.g., "Hytrel® polyester elastomer," commercially available from Du Pont Co., Wilmington, Del.) and plasticized polylactic acid such as Natureworks Ingeo 6202 polylactic acid plasticized with a compatible plasticizer such as a citrate alkyl ester, and polyamides such as polyether polyamides (e.g., "Pebax® Resins" commercially available from ELF Atochem, North America, Inc., Philadelphia, Pa.), acrylic block copolymers such as Kurarity polymers available from Kuraray America Houston, Tex., and styrene block copolymers such as styrene/isoprene/styrene (SIS) and styrene/butadiene/styrene (SBS) available from Kraton Polymers. In order to alter the deformability of these thermoplastics, plasticizers and/or fillers may be added. Preferred plasticizers are soluble and do not migrate out over time. Method 200 includes deforming the warming blanket 11 to form a shape with respect to the periphery 14 that is a different shape from the initial shape formed by the periphery while warming blanket was in the initial shape. Deforming the warming blanket 11 including deforming the warming blanket while maintaining the integrity of the passageways capable of providing distribution of air flows through the interior space and passageways 15 of the warming blanket (block 304). In various examples, deforming the warming blanket includes deforming the shape of the warming blanket so that a thickness dimension of the warming blanket, when inflated, is maintained to about +/−50% of a thickness dimension the warming blanket would assume if inflated while remaining in the initial shape, e.g., the change in thickness dimensions less than 50% across the entire length of the portion of the warming blanket providing passageways 15.

Examples of method 300 include inflating the warming blanket to maintain the warming blanket in the shape that is different from the initial shape (block 306). Maintaining the warming blanket in the shape that is different form the initial shape may include inflating the warming blanket with a flow of air, and placing the warming blanket proximate to a patient to provide warming to the patient while the warming blanket is in the different shape.

Figure 9A:
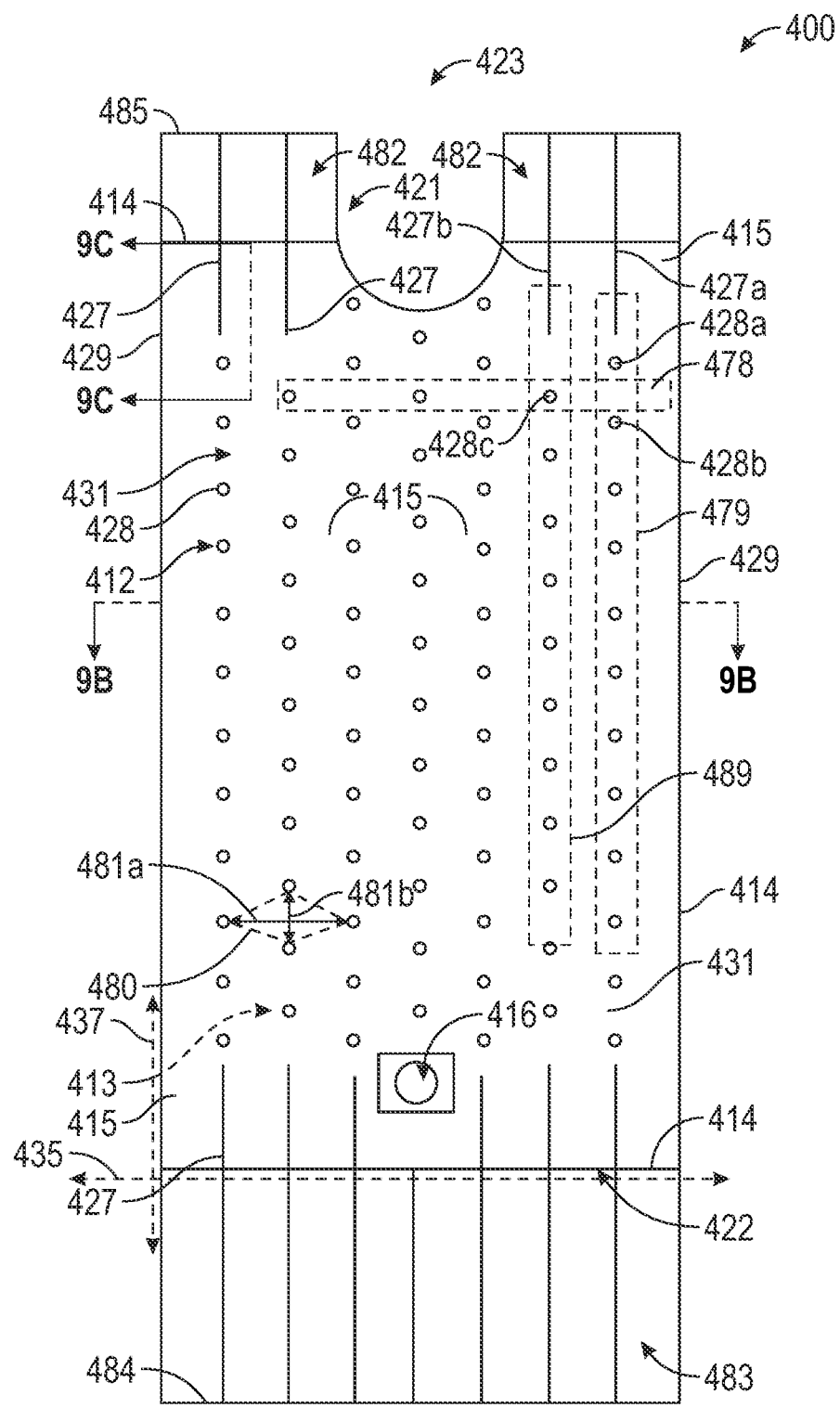
FIG. 9A shows a top elevation view of an uninflated forced-air blanket having a rectilinear array of staked seals in a staggered arrangement.
Figure 10A:
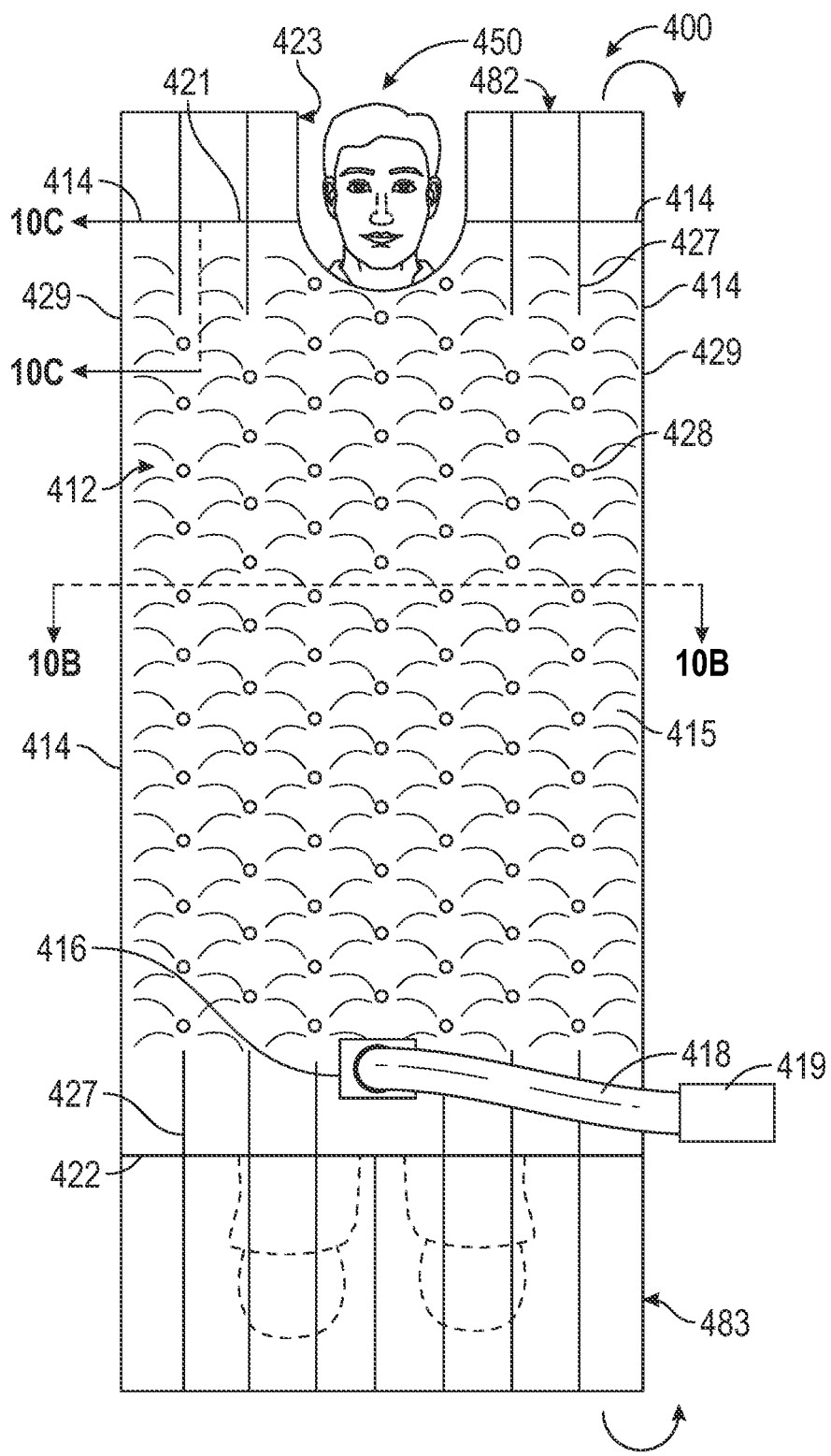
FIG. 10A shows a tops elevations view of an inflated forced-air blanket having a rectilinear array of staked seals in a staggered arrangement.

FIGS. 9A-9C illustrate an embodiment of a forced-air blanket 400 shown in an uninflated state. The forced-air blanket 400 can have a first staggered pattern. FIGS. 10A-10C illustrate the forced-air blanket 400 in an inflated state. The forced-air blanket 400 is shown as a full-body blanket but can be in any other configuration. The numbering of components of the forced-air blanket 400 can correspond to that of components in FIGS. 1, 2, and 4. For example, upper layer 412 can correspond to upper layer 12 of FIG. 1.

In FIG. 9A, the forced-air blanket 400 can have an upper layer 412 and a bottom layer 413. The upper layer 412 can be bonded to the bottom layer 413 using a variety of seals, including a plurality of linear seals and a plurality of staked seals as discussed herein. An inlet 416 can be bonded to the upper layer 412 and form an opening within the upper layer 412. The bottom layer 413 can have a plurality of openings as described herein. One aspect of the embodiment in the forced-air blanket 400 is that the plurality of staked seals form a rectilinear array having a staggered arrangement or staggered pattern.

The bonding of the two layers can form a plurality of interconnected air passageways 415 (here formed between the staked seals 428 and/or linear seals 427). The upper layer 412 and the bottom layer 413 can be bonded along the periphery 414 using linear seals which do not allow air to pass. The linear seals along the periphery 414 create longitudinal sides 429 and latitudinal sides 421 and 422 (also referred to as an end). In at least one embodiment, the periphery 414 can mean a perimeter of an area of the forced-air blanket capable of being inflated.

The forced-air blanket 400 can have a cutout 423 formed from a portion of the forced-air blanket 400. The cutout 423 can create two portions of the forced-air blanket 400 that are adjacent to the cutout 423. In at least one embodiment, the cutout 423 can be of an appropriate size to fit a head of a patient while the forced-air blanket 400 is draped over the patient's body.

In at least one embodiment, the forced-air blanket 400 has at least one area that is not capable of being inflated. The uninflatable areas can be used for various purposes. For example, the uninflatable areas can be draped over a part of a patient to allow for a secure fit. Area 482 and area 483 are shown as not capable of being inflated. Area 482 is bordered by a linear seal 485 along a latitudinal axis 435 of the forced-air blanket 400, linear seals along the longitudinal sides 429 (generally following longitudinal axis 437) of the forced-air blanket 400, a linear seal along the cutout 423, and a linear seal along the periphery 414 of an inflatable area 431. Area 483 is bordered by a linear seal 484 along a latitudinal axis 435 of the forced-air blanket 400, linear seals along the longitudinal sides 429 of the forced-air blanket 400, and a linear seal along the periphery 414 of an inflatable area 431.

The forced-air blanket 400 can have at least one area that is capable of being inflated, e.g., area 431. The inflatable area 431 can diffuse blown air across the bottom layer 413 of the forced-air blanket 400 through a plurality of openings (not shown). The plurality of staked seals 428 can keep the middle of the area from increasing the loft and decreasing the width of the forced-air blanket 400.

At least some of the linear seals 427 can be bonded to a portion of the periphery 414. In some embodiments, at least two of the linear seals 427 can be oriented longitudinally, i.e., running lengthwise rather than across the forced-air blanket 400.

In some embodiments, longitudinally can mean in a parallel direction with the longitudinal sides 429. For example, the linear seals 427a and 427b can be parallel to at least one portion of a longitudinal side 429. In at least one embodiment, the linear seals 427a and 427b can be parallel to a complete longitudinal side 429. The linear seals 427a and 427b are shown adjacent to one another.

The forced-air blanket 400 can have a plurality of staked seals 428. The plurality of staked seals 428 can be arranged in a rectilinear array. A rectilinear array can have straight lines of staked seals in a rectangular pattern.

The plurality of staked seals can be arranged in a plurality or parallel rows including a first row 479 and a second row 489. Each row can have a first staked seal and a second staked seal. For example, the first row 479 can have a first staked seal 428a and a second staked seal 428b. The first row 479 is collinear with the first linear seal 427a and the second row 489 is collinear with the second linear seal 427b. In some embodiments, collinear means following the path of a line, including a curved lined.

As opposed to a grid pattern shown in FIG. 4, where a framework of rows of staked seals are parallel or cross other rows to form a series of squares or rectangles, a staggered pattern can be used. The staggered pattern is generally arranged so that staked seals in adjacent rows of staked seals do not form a column that is perpendicular to the row. For example, wherein the first staked seal 428a from the first row 479 is not collinear with the first staked seal 428c from the second row 489 in a perpendicular axis 478 to the first row 479. In at least one embodiment, the first staked seal 428c from the second row 489 is arranged intermediate between the first staked seal 428a and the second staked seal 428b from the first row 479.

Further, the staggered pattern of 400 can further include four adjacent staked seals from the plurality of staked seals forming a rhombus 480 having a first diagonal 481a and a second diagonal 481b. The first diagonal 481a has a length greater than the second diagonal 481b. In the staggered pattern of 400, the first diagonal 481a is oriented perpendicular to the first row 479.

FIG. 9B illustrates side cross sectional view taken latitudinally across the forced-air blanket 400. The longitudinal sides 429 have a seal that bonds the upper layer 412 to the bottom layer 413. Four staked seals 428 also bond the upper layer 412 to the bottom layer 413. The forced-air blanket 400 has an uninflated height of H2 and a width of W2.

FIG. 9C illustrates a side view over a portion of the forced-air blanket 400. For example a linear seal 427 can bond the two layers 412 and 413. In addition, an end 421 can be formed from a seal between the two layers 412.

FIGS. 10A-10C illustrate the forced-air blanket 400 inflated. In FIG. 10A, the forced-air blanket 400 is shown with a patient 450. The forced-air blanket 400 can be coupled to a hose 418 (through inlet 416) and a source 419 for the purposes of inflation. The patient's 450 head can fit through the cutout 423. The uninflated areas 482 and 483 can be folded over the patient 450 including extremities. When inflated, can form within the periphery 414.

In FIG. 10B, the inflated 400 forms a plurality of interconnected air passageways 415 between longitudinal sides 429. The upper layer 412 can extend as much as the bottom layer 413. When combined with the source 419, a plurality of openings in bottom layer 413 can produce an airflow 420 that contacts the patient 450. The inflated 400 has a height of H3 and a width of W3. The width W3 can be less than W2 due to the increased height H3.

In FIG. 10C, the airflow 420 does not extend along the linear seal 427 but rather through the inflated portions between the linear seals 427.

Figure 11A:
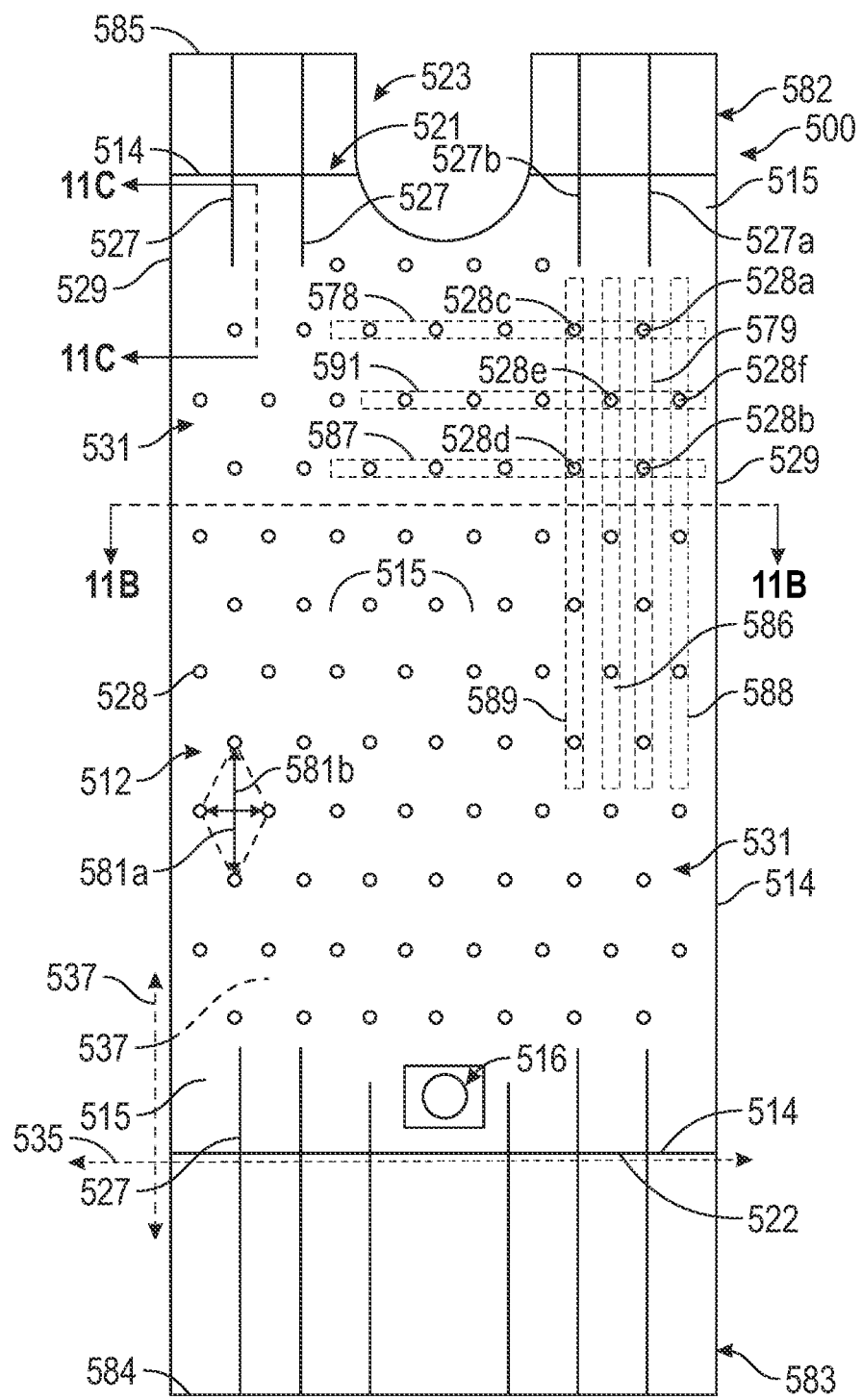
FIG. 11A shows a top elevation view of another embodiment of an uninflated forced-air blanket having a rectilinear array of staked seals in a staggered arrangement.
Figure 11B:
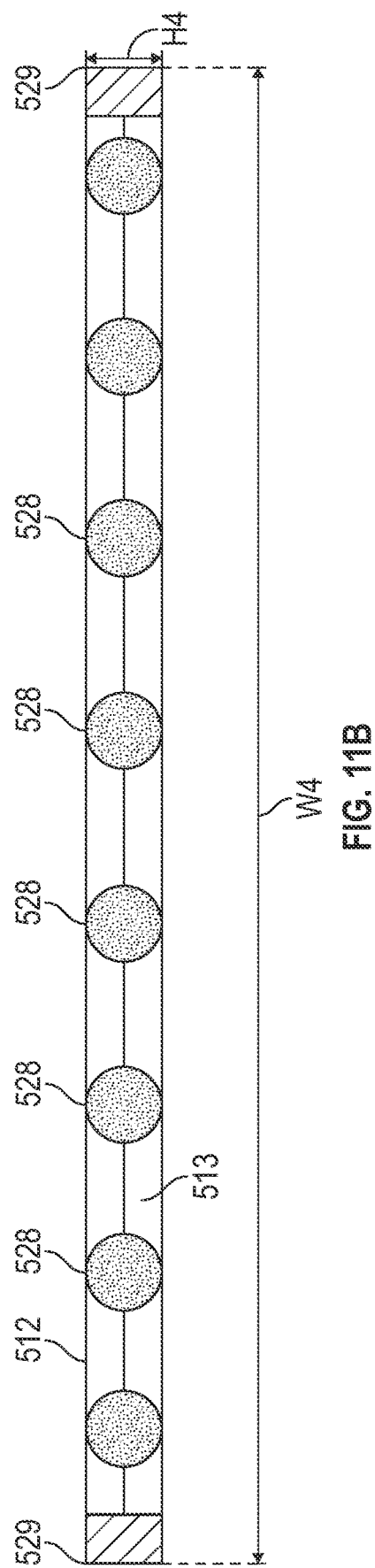
FIG. 11B shows a side cross-sectional view of the uninflated forced-air blanket of FIG. 11A viewed along the lines of 3-3.
Figure 11C:
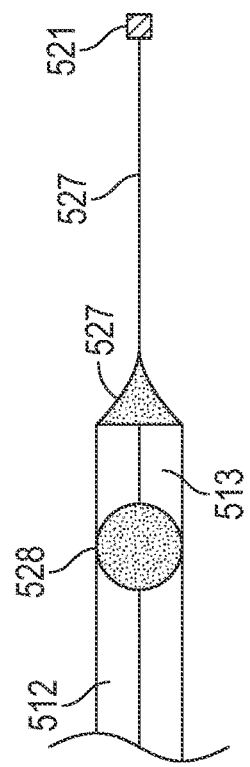
FIG. 11C shows a side cross-sectional view of the inflated forced-air blanket of FIG. 11A viewed along the lines of 4-4.
Figure 12A:
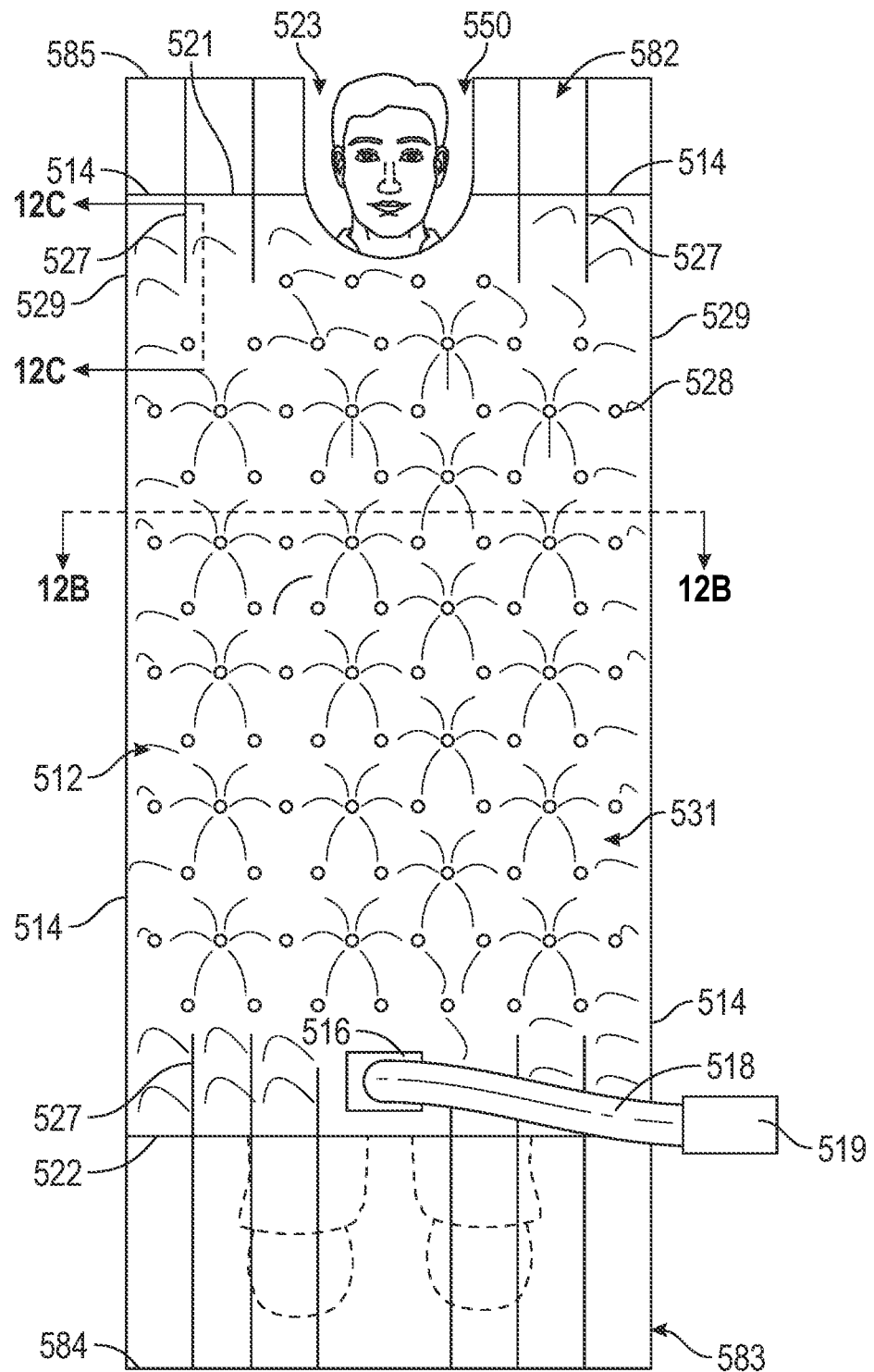
FIG. 12A shows a top elevation view of another embodiment of an uninflated forced-air blanket having a rectilinear array of staked seals in a staggered arrangement.
Figure 12B:
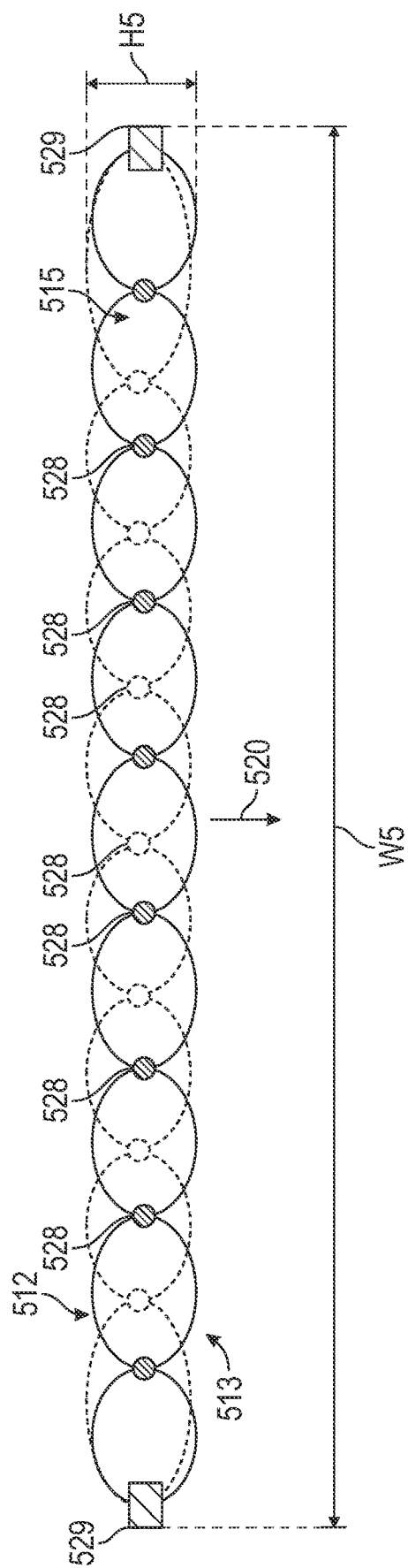
FIG. 12B shows a side cross-sectional view of the uninflated forced-air blanket of FIG. 12A viewed along the lines of 3-3.
Figure 12C:
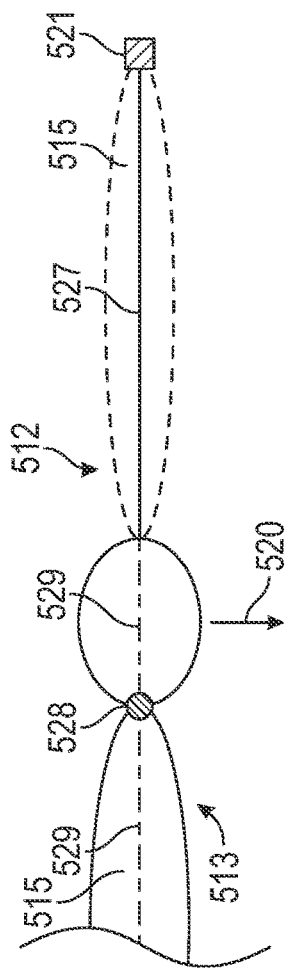
FIG. 12C shows a side cross-sectional view of the inflated forced-air blanket of FIG. 12A viewed along the lines of 4-4.

FIGS. 11A-11C illustrate an embodiment of a forced-air blanket 500 shown in an uninflated state. FIGS. 12A-12C illustrate the forced-air blanket 500 in an inflated state. The forced-air blanket 500 is shown as a full-body blanket but can be in any other configuration. The numbering of components of the forced-air blanket 500 can correspond to that of components in FIGS. 1, 2, 4, and particularly 9 and 10. For example, upper layer 512 can correspond to upper layer 412 of FIGS. 9-10 and upper layer 12 of FIG. 1. The difference between the forced-air blanket 400 of FIGS. 9-10 and the forced-air blanket 500 of FIGS. 11-12 is at least in the staggered pattern. The forced-air blanket 400 can have a first staggered pattern and the forced-air blanket 500 can have a second staggered pattern. Differences in the height and the width can be observed between the forced-air blanket 400 and the forced-air blanket 500.

In FIG. 11A, the forced-air blanket 500 can have an upper layer 512 and a bottom layer 513. The upper layer 512 can be bonded to the bottom layer 513 using a variety of seals, including a plurality of linear seals and a plurality of staked seals as discussed herein. An inlet 516 can be bonded to the upper layer 512 and form a hole from the inlet. Although not pictured, the bottom layer 513 can have a plurality of openings as described herein.

The bonding of the two layers can form a plurality of interconnected air passageways 515 (here formed between the staked seals 528 and/or linear seals 527). The upper layer 512 and the bottom layer 513 can be bonded along the periphery 514 using linear seals which do not allow air to pass. The linear seals along the periphery 514 create a longitudinal sides 529 and latitudinal sides 521 and 522 (also referred to as an end).

The forced-air blanket 500 can have a cutout 523 formed from a portion of the forced-air blanket 500. The cutout 523 can create two portions of the forced-air blanket 500 that are adjacent to the cutout 523. In at least one embodiment, the cutout 523 can be of an appropriate size to fit a head of a patient while the forced-air blanket 500 is draped over the patient's body.

In at least one embodiment, the forced-air blanket 500 has at least one area that is not capable of being inflated. The uninflatable areas can be used for various purposes. For example, the uninflatable areas can be draped over a part of a patient to allow for a secure fit. Area 582 and area 583 are shown as not capable of being inflated. Area 582 is bordered by a linear seal 585 along a latitudinal axis 535 of the forced-air blanket 500, a linear seals along the longitudinal sides 529 (generally following longitudinal axis 537) of the forced-air blanket 500, a linear seal along the cutout 523, and a linear seal along the periphery 514 of an inflatable area 531. Area 583 is bordered by a linear seal 584 along a latitudinal axis 535 of the forced-air blanket 500, linear seals along the longitudinal sides 529 of the forced-air blanket 500, and a linear seal along the periphery 514 of an inflatable area 531.

The forced-air blanket 500 can have at least one area that is capable of being inflated, e.g., area 531. The inflatable area 531 can diffuse pressurized air across the bottom layer 513 of the forced-air blanket 500 through a plurality of openings (not shown). The plurality of staked seals 528 can keep the middle of the area from increasing the loft and decreasing the width of the forced-air blanket 500.

At least some of the linear seals 527 can be bonded to a portion of the periphery 514. In some embodiments, at least two of the linear seals 527 can be oriented longitudinally, i.e., running lengthwise rather than across the forced-air blanket 500. For example, the first linear seal 527a is joined to a portion of the periphery 514 at an end 521 of the forced-air blanket to form a seal with the periphery 514.

In some embodiments, longitudinally can mean in a parallel direction with the longitudinal sides 529. For example, the linear seals 527a and 527b can be parallel to at least one portion of a longitudinal side 529 and/or to each other. In at least one embodiment, the linear seals 527a and 527b can be parallel to a complete longitudinal side 529. The linear seals 527a and 527b are shown adjacent to one another.

The forced-air blanket 500 can have a plurality of staked seals 528. The plurality of staked seals 528 can be arranged in a rectilinear array. A rectilinear array can have straight lines of staked seals in a rectangular pattern.

The plurality of staked seals can be arranged in a plurality or parallel rows including a first row 579 and a second row 589. Each row can have a first staked seal and a second staked seal. For example, the first row 579 can have a first staked seal 528a and a second staked seal 528b that are adjacent to one another. The first row 579 is collinear with the first linear seal 527a and the second row 589 is collinear with the second linear seal 527b. As shown, the first row 579 is adjacent to the longitudinal side 529 of the forced-air blanket.

In at least one embodiment, at least two staked seals (e.g., 528a, and 528c) are equally spaced from at least two adjacent linear seals (e.g., 527a, and 527b). For example, the first staked seal 528a of the first row 579 and an end (opposite the periphery 514) of the first linear seal 527a and the first staked seal 528c of the second row 589 and an end (opposite the periphery 514) of the second linear seal 527b are equally spaced.

In at least one embodiment, at least some of the plurality of staked seals 528 are arranged in a plurality of columns. A column can include at least one staked seal (e.g., 528a) of the first row 579 and at least one staked seal (e.g., 528c) of the second row 589. Shown in 500 is a first column 578, and a second column 587. A column can be perpendicular to any row.

In at least one embodiment, at least some of the plurality of staked seals are arranged in a first alternate row 586 which includes a first alternate staked seal 528e and a second alternate staked seal. In some embodiments, the distance between the alternate row and the first row can be half that of the distance from the first row to the second row. At least one staked seal of the first alternate row 586 is arranged intermediate between the first row 579 and the second row 589 and arranged intermediate between two adjacent staked seals in the first row (e.g., 528a and 528b). At least one alternate staked seal from the first alternate row 586 is arranged intermediate between at least two columns (e.g., column 578 and column 587) from the plurality of columns.

In at least one embodiment, the first alternate staked seal 528e of the first alternate row 586 is arranged intermediate between two adjacent staked seals (e.g., 528c and 528d) in the second row 589. Further, at least one staked seal of the first alternate row 586 can be arranged intermediate between a first staked seal 528a of the first row 579 and a second staked seal 528d of the second row 589. Generally, at least one staked seal of the first alternate row 586 is arranged diagonal from the first staked seal 528a of the first row 579.

In at least one embodiment, the plurality of staked seals 528 are arranged in a second alternate row 588 comprising two or more staked seals. In some embodiments, the second alternate row 588 can be arranged intermediate between the first row 579 and the longitudinal side 529 of the forced-air blanket. In some embodiments, at least one staked seal in the second alternate row 588 is arranged intermediate between at least two columns from the plurality of columns.

Alternate column 591 can include the first alternate staked seals (e.g., 528e and 528f) of the first alternate row 586 and the second alternate row 588. Alternate column 591 can be oriented latitudinally along with columns 578 and 587

Further, the staggered pattern of 500 can further include four adjacent staked seals from the plurality of staked seals forming a rhombus 580 having a first diagonal 581a and a second diagonal 581b. The first diagonal 581a has a length greater than the second diagonal 581b. In the staggered pattern of 500, the first diagonal 581a is oriented parallel with the first row 579.

FIG. 11B illustrates side cross sectional view taken latitudinally across the forced-air blanket 500. The longitudinal sides 529 have a seal that bonds the upper layer 512 to the bottom layer 513. Four staked seals 528 also bond the upper layer 512 to the bottom layer 513. The forced-air blanket 500 has an uninflated height of H4 and a width of W4.

FIG. 11C illustrates a side view over a portion of the forced-air blanket 500. For example a linear seal 527 can bond the two layers 512 and 513. In addition, an end 521 can be formed from a seal between the two layers 512.

FIGS. 12A-12C illustrate the forced-air blanket 500 inflated. In FIG. 12A, the forced-air blanket 500 is shown with a patient 550. The forced-air blanket 500 can be coupled to a hose 518 (through inlet 516) and a source 519 for the purposes of inflation. The patient's 550 head can fit through the cutout 523. The uninflated areas 582 and 583 can be folded over the patient 550 including extremities. When inflated, can form within the periphery 514.

In FIG. 12B, the inflated 500 forms a plurality of interconnected air passageways 515 between longitudinal sides 529. The upper layer 512 can extend as much as the bottom layer 513. When combined with the source 519, a plurality of openings in bottom layer 513 can produce an airflow 520 that contacts the patient 550. The inflated 500 has a height of H5 and a width of W5.

Unexpectedly, due to the pattern difference between 400 and 500, the width W5 of the inflated 500 was greater than the width W3 of the inflated 400. For example, the width W5 using the staggered pattern of 500 was at least 110% of the width W3 using the staggered pattern of 400.

In FIG. 12C, the airflow 520 does not extend along the linear seal 527 but rather through the inflated portions between the linear seals 527.

Figure 13:
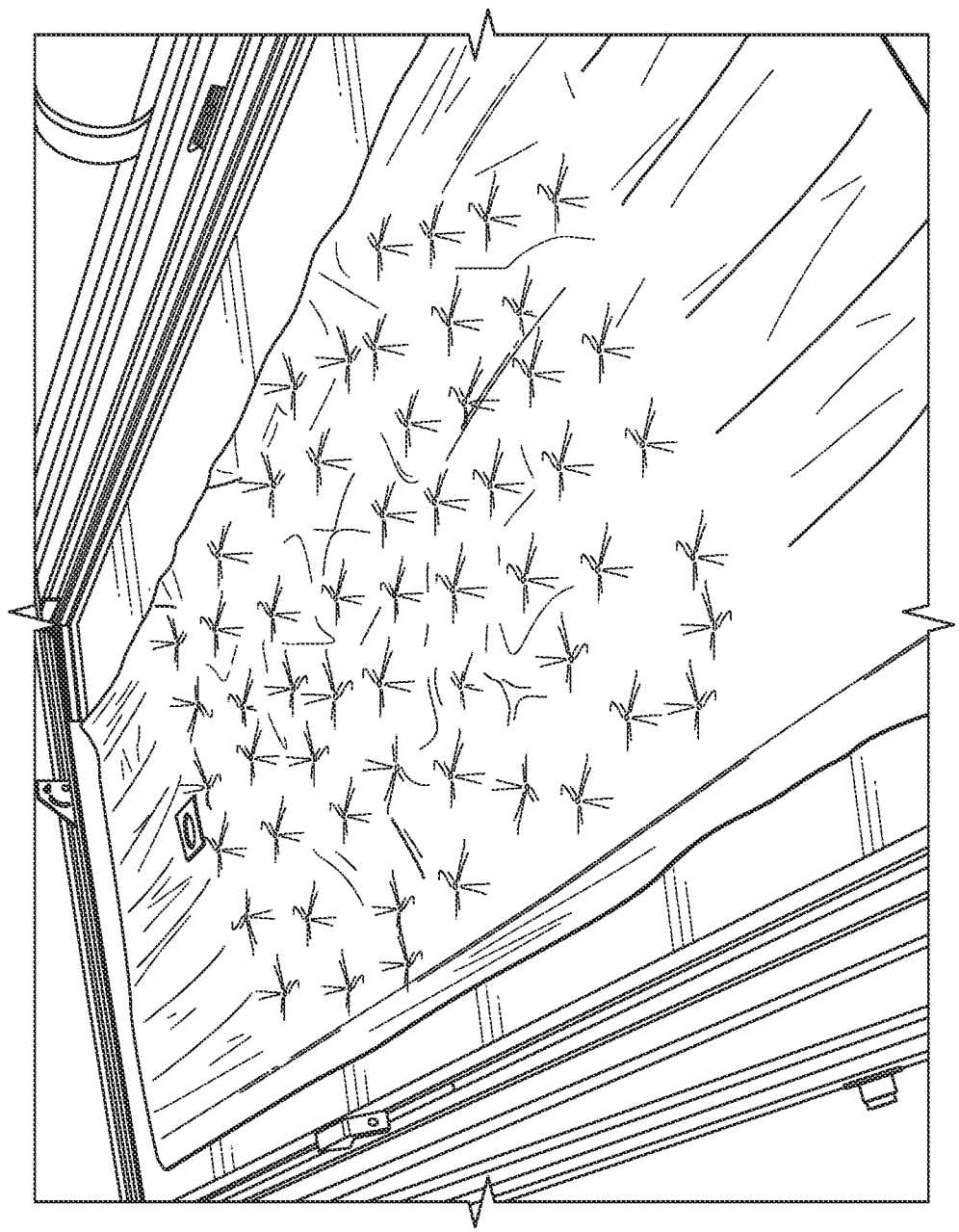
FIG. 13 shows a perspective view of an uninflated forced-air blanket.
Figure 14A:
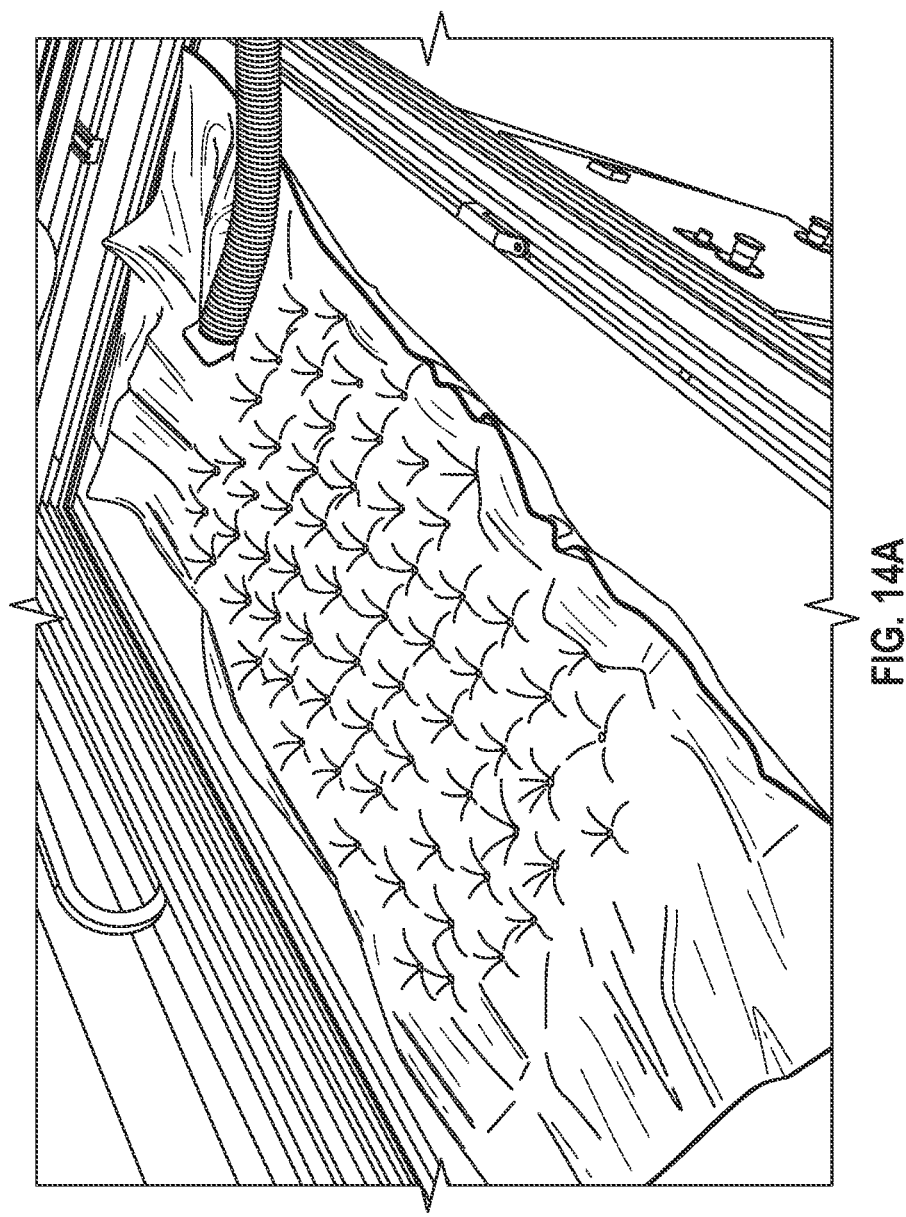
FIG. 14A shows a perspective view of an inflated forced-air blanket.
Figure 14B:
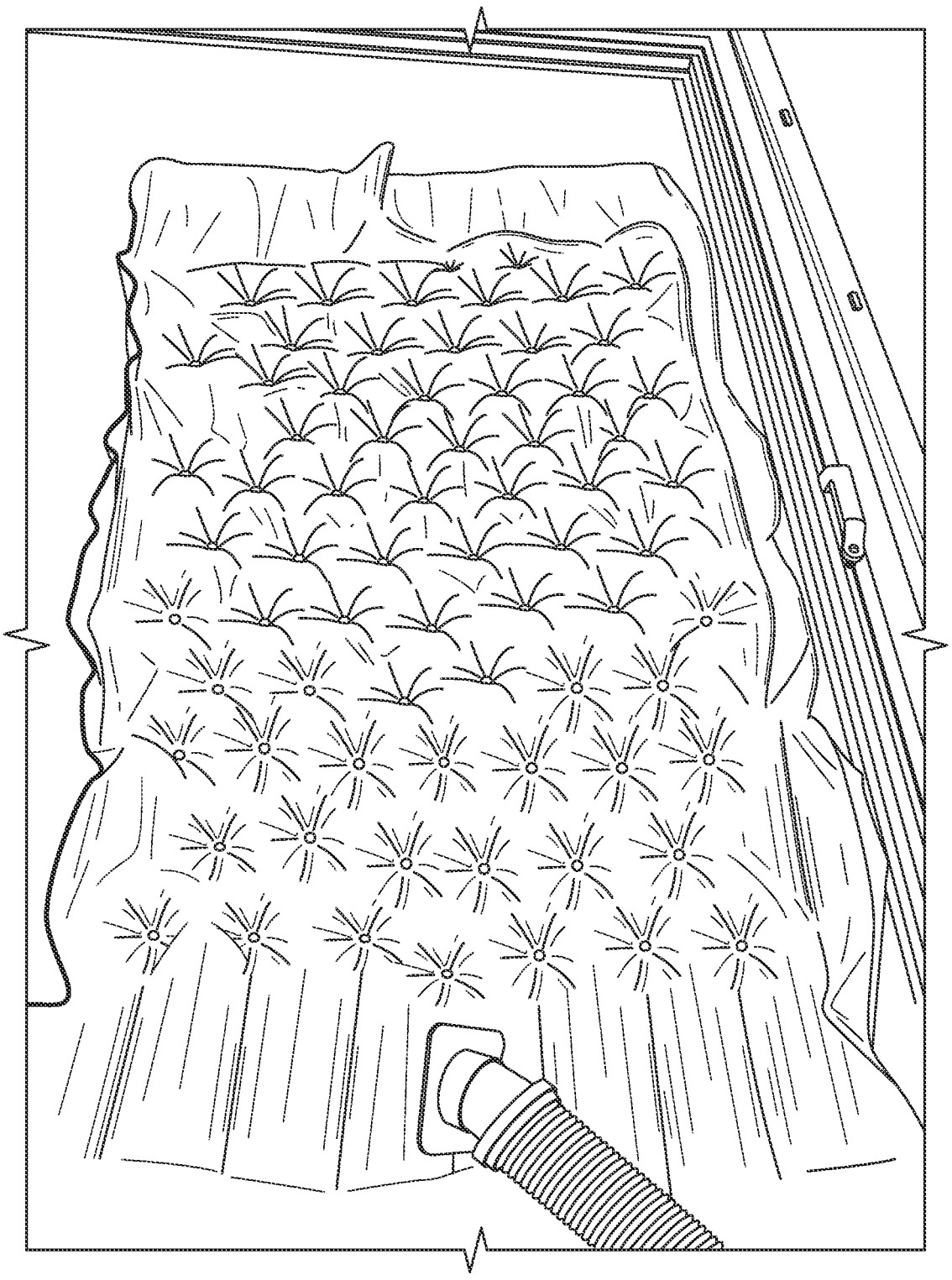
FIG. 14B shows a different perspective view of an inflated forced-air blanket.

FIGS. 13, and 14A-14B illustrate photographic images of a forced-air blanket using the pattern of 500.

Figure 15A:
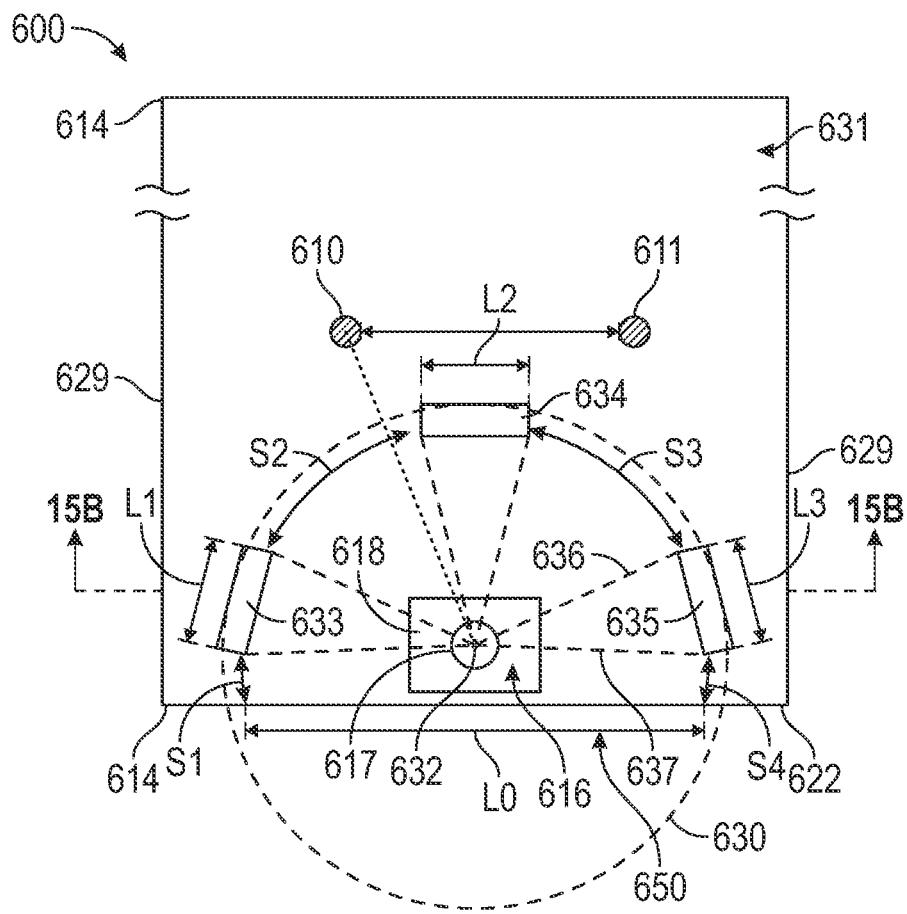
FIG. 15A shows a top elevational view of a forced-air blanket with at least one elongated seal proximate to an inlet.
Figure 15B:
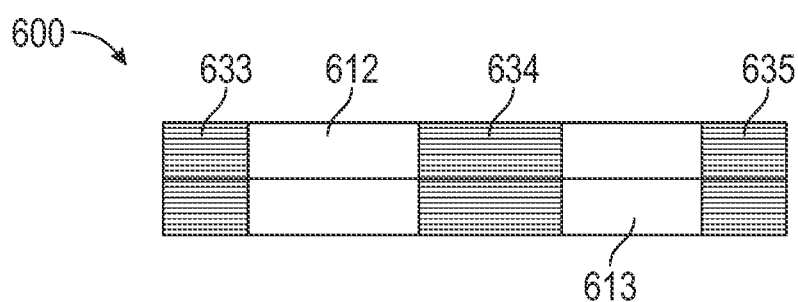
FIG. 15B shows a side cross-sectional view of a forced-air blanket along lines 5-5.

FIGS. 15A-15B show a forced-air blanket 600. An inlet 616 of the forced-air blanket 600 can be subjected to various rotational and tipping forces which can cause one or more staked seals to fail, thus separating layers of the forced-air blanket 600 that are surrounding the inlet 616. Aspects of the present disclosure relate to having at least one elongated seal proximate to the air inlet 616 and facing the air inlet 616.

The forced-air blanket 600 can have a plurality of layers as shown in FIG. 15B. FIG. 15B shows an upper layer 612 and a bottom layer 613. The upper layer 612 and bottom layer 613 are discussed herein. The forced-air blanket 600 can also have a plurality of interior seals (e.g., elongated seals 633, 634 and 635) with a plurality of interior seals bonding at least two of the plurality of layers (e.g., 612, and 613). In some embodiments, more than two layers can be used to create various passageways for air.

Returning to FIG. 15A, the forced-air blanket 600 can have at least one air inlet 616 as described in embodiments herein. The air inlet 616 is coupled to at least one of the plurality of layers (e.g., the upper layer 612). In at least one embodiment, the air inlet 616 is formed from an opening 617 within at least one of the plurality of layers. The opening 617 (as described herein) can have at least one edge which forms the border of the air inlet 616. In addition, the air inlet 616 can have a collar 618 which is described herein. The opening 617 of the air inlet 616 can have a center 632. The center 632 can be equidistant with at least two points along the edge of an opening 617.

The forced-air blanket 600 can have longitudinal sides and at least one end 622 which can form a portion of the periphery 614. The forced-air blanket 600 can have a plurality of seals including a plurality of interior seals and a seal along the periphery 614 as described in embodiments herein. An interior seal can be located within the area 631 established by the periphery 614. Various interior seals can exist including an elongated seal. The elongated seal can be any seal between the layers that has a greater length than width. In at least one embodiment, the elongated seal can include a variety of linear seals or staked seal. Each elongated seal can be positioned proximate to the inlet 616.

The forced-air blanket 600 is shown with a plurality of elongated seals, elongated seal 633, elongated seal 634, and elongated seal 635. Each of the elongated seals can be proximate to the inlet 616 (preferably the center 632 of the inlet). The proximity of the elongated seals can be a balance of securement and airflow. If the elongated seals are too close to the inlet, then airflow restrictions can result. Conversely, if the elongated seals are too far from the inlet, then the adhesion between the plurality of layers may be compromised.

The proximity of the elongated seals to the inlet 616 can be established by a perimeter region 630 around at least a portion of the air inlet 616. The perimeter region 630 can be a notional boundary surrounding the inlet 616. Seals within the edge of the perimeter region may provide structural securement from the forces of the inlet 616 that cause a separation of the layers. The perimeter region 630 is defined by a distance to the center 632 of the air inlet. In at least one embodiment, the distance is no greater than 50 cm, no greater than 40 cm, or even no greater than 30 cm. The perimeter region 630 can be any shape but is preferably a circle. The perimeter region 630 extends into regions having two or more layers, but if the inlet 616 is along an end 622 of the forced-air blanket 600, then the perimeter region 630 encompasses an area that has no layers.

In at least one embodiment, the elongated side of the at least one elongated seal is positioned along the radius of curvature of the perimeter region 630. For example, elongated seal 633 is shown aligned with the radius of curvature of the perimeter region 630.

In at least one embodiment, the forced-air blanket 600 has at least two adjacent staked seals 610, and 611 having a particular distance between them. This proximal distance 628 from the center 632 to a staked seal 610 is greater than the radial distance 637 of the perimeter region 630. In some embodiments, the radial distance 637 is no greater than the distance between two adjacent staked seals (e.g., 610 and 611). In at least one embodiment, the elongated side of an elongated seal has a length that is no greater than 50% of the length (e.g., circumference) of the perimeter region 630.

The elongated seal can have at least two sides with one side (i.e., the elongated side) facing the inlet. Facing can generally mean that the elongated side of an elongated seal faces the inlet 616. In some embodiments, an elongated seal can be facing if a longitudinal axis of the elongated seal is not aligned with a radial dimension of the inlet 616. The radial dimension generally originates from the center 632. In at least one embodiment, the elongated seal is facing when a radial dimension of the inlet 616 aligns with at least two ends of an elongated seal. For example, radial dimension 636 can align with an end of 635, and a radial dimension 637 can align with another end of 635. Thus, the elongated seal 635 can be facing the inlet 616.

The plurality of elongated seals can have a length measured along the radius of curvature of the perimeter region 630. For example, seal 633 has a length L1, seal 634 has a length L2, and seal 635 has a length L3. The elongated seals can have various distances or spacings between each other. For example, the spacing between seal 633 and seal 634 can be S2, the spacing between seal 634 and seal 635 can be S3. In at least one embodiment, the space between two elongated seals can be at least 1 cm. The forced-air blanket 600 has a seal along the periphery 614 at end 622 that is within the perimeter region 630. The seal 650 within the perimeter region 630 has a length of L0. The spacing between seal 633 and seal 650 is S1 and the spacing between seal 635 and seal 650 is S4.

The combined length of the plurality of seals in the perimeter region (i.e., seal 633, 634, 635, and 650) is L0+L1+L2+L3+L4. The combined space within the perimeter region between the plurality is seals is S1+S2+S3+S4 (i.e., a sum total of the spaces in the perimeter region 630).

In at least one embodiment, the combined length is less than the combined space. Thus, a majority of the circumference of the perimeter region can be space for air to flow from the inlet 616.

In at least one embodiment, the concentration of interior seals can be determined using area. For example, the area of the elongated seals can have a combined area that is less than the area of non-sealed portions within the perimeter region 630. For example, the space between the inlet and each of the seals can have an area that is greater than the sealed area (including the seal 650).

Figure 16:
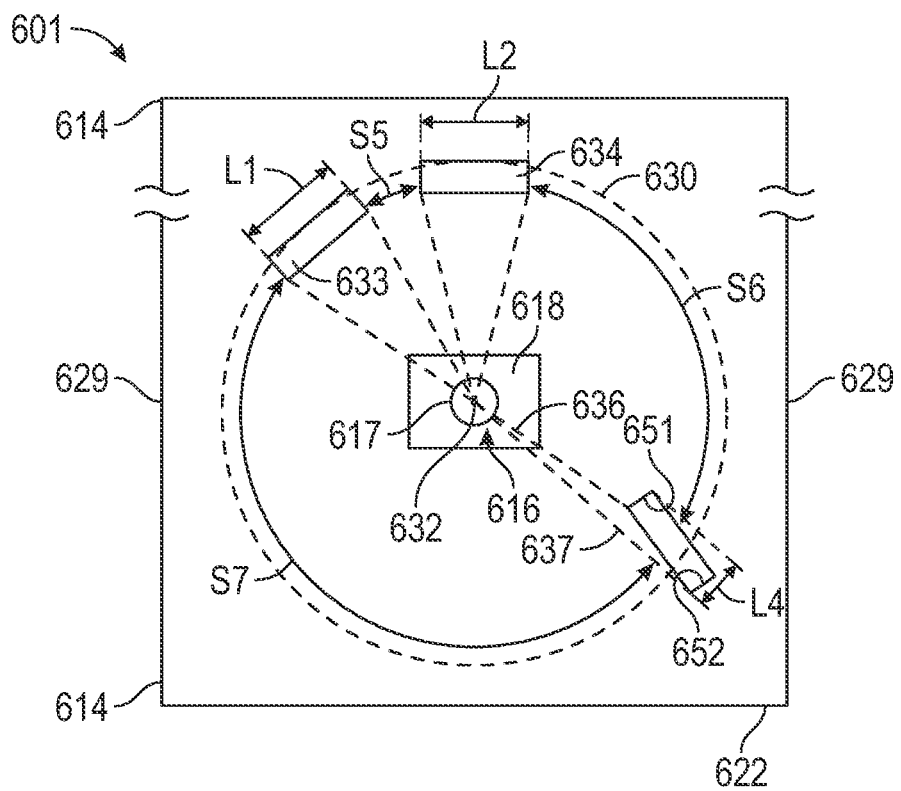
FIG. 16 shows a top elevational view of a forced-air blanket with another configuration of an inlet.

FIG. 16 shows another embodiment of a forced-air blanket 601 having a plurality of elongated seals. Components of the forced-air blanket 601 can be configured the same as the forced-air blanket 600 in FIGS. 15A-B except that the perimeter region 630 does not encompass an end of the forced-air blanket 601.

The elongated seal 635 is shown facing the inlet 616. For example, radial dimension 636 aligns with end 651 and radial dimension 637 aligns with end 652 of the elongated seal 635. In at least one embodiment, the length L4 of elongated seal 635 is based on the and the distance from end 651 to the end 652 along radius of curvature of the perimeter region 630. In some embodiments, the length L4 starts from end 651 and following an inner radius of curvature.

Seal 633 can have a length of L1, and seal 634 can have a length of L2. The combined length can be L1+L2+L4. The seals can have a combined space of S5+S6+ and S7. As in the forced-air blanket 600, the combined length can be no greater than the combined space.

Figure 17:
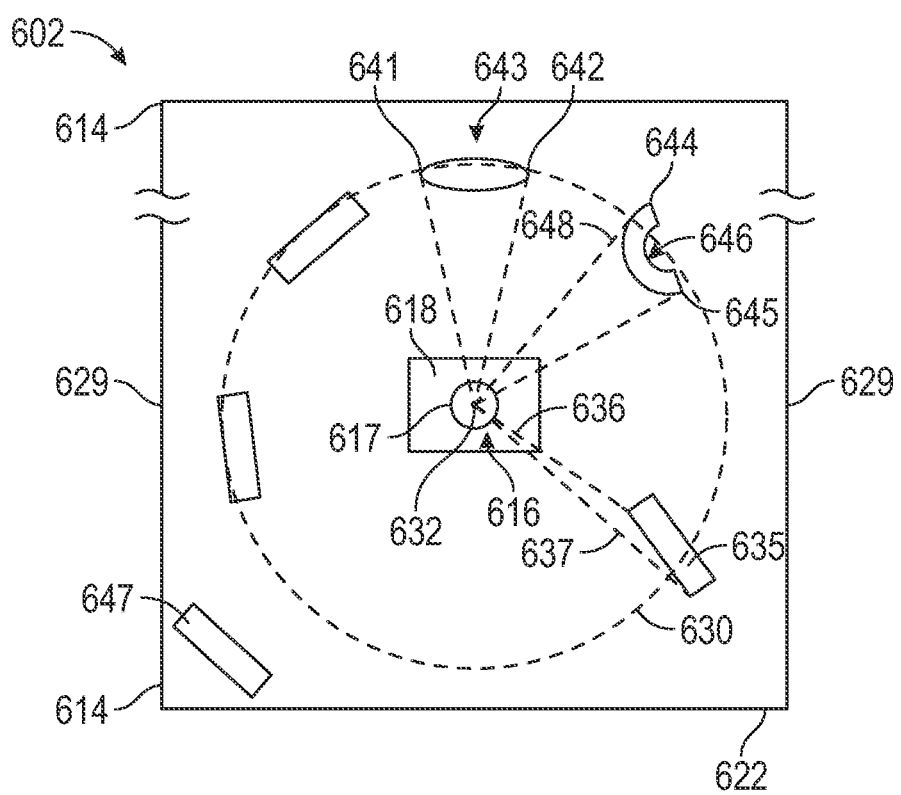
FIG. 17 shows a top elevational view of a forced-air blanket with various elongated seals.

FIG. 17 shows another embodiment of a forced-air blanket 602 having a plurality of elongated seals. Components of the forced-air blanket 602 can be configured the same as the forced-air blanket 600 in FIGS. 15A-B and 601 in FIG. 16 except that some elongated seals are shown not facing the inlet 616.

The forced-air blanket 602 can have a plurality of elongated seals around the perimeter region 630. The elongated seal 646 and elongated seal 643 has at least one curved side.

In elongated seal 646, the elongated side is the curved side and is C-shaped. However, the elongated seal 646 is not facing the inlet 616 because end 644 does not align with the radial dimension 648 (even though end 645 aligns with a radial dimension which originates from the center 632).

In elongated seal 643, the radial dimensions of the perimeter region 630 align with end 641 and end 642. Thus, at least one elongated side is facing the inlet 616. Elongated seal 643 is ellipsoidal shaped.

Elongated seal 647 is facing the inlet 616 but is not within the perimeter region 630.

The following examples describe one or more aspects of the disclosure.

Example 1

A forced-air blanket for providing a profusion of air to a patient, the forced-air blanket comprising: a structure comprising a first layer of material and a second layer of material, the first layer of material forming a bottom layer of the forced-air blanket, the bottom layer comprising a plurality of openings formed from the bottom layer therein configured to allow a profusion of air to pass through the bottom layer, the second layer of material forming an upper layer of the forced-air blanket, the upper layer bonded to the bottom layer around a periphery to form an area of the upper layer and the bottom layer enclosed within the periphery, the upper layer further bonded to bottom layer by a plurality of linear seals and a plurality of staked seals forming a plurality of interconnected air passageways; and at least one air inlet coupled to the interconnecting air passageways, the inlet configured to receive a flow of air, and to provide the flow of air to the bottom layer through the interconnected air passageways; wherein the area enclosed within the periphery of the forced-air blanket provides an interior space comprising the plurality of interconnected air passageways between the upper layer and the bottom layer, the passageways further defined by a plurality of connections formed between the upper layer and the bottom layer within the area defined by the periphery, and by the plurality of linear seals, and the plurality of staked seals, and wherein at least one of the plurality of linear seals is sealingly joined to a portion of the periphery.

Example 2

The forced-air blanket of example 1, wherein the linear seals are located at end of the forced-air blanket and have a longitudinal orientation that corresponds to the longitudinal dimension of the forced-air blanket, and have a first end that joins with the periphery at an end to form a seal with periphery.

Example 3

The forced-air blanket of example 2, wherein the number of linear seals at each end of the forced-air blanket is greater than 2 and less than 5.

Example 4

The forced-air blanket of example 2, wherein the number of linear seals at each end of the forced-air blanket is 3.

Example 5

The forced-air blanket of any of examples 1-4, wherein two or more of the plurality staked seals form a row in a line that aligns with a longitudinal orientation of at least one of the linear seals.

Example 6

The forced-air blanket of any of examples 1-5, wherein one or more of the plurality of linear seals are formed as a continuous air impervious seal.

Example 7

The forced-air blanket of any of examples 1-6, wherein one or more of the plurality of linear seals are formed as a discontinuous air permeable seal.

Example 8

The forced-air blanket of any of examples 1-7, where one or more of the linear seals comprise a seal having a length dimension of in a range of 5 to 25 cm and a width dimension in a range of 2 to 20 mm comprising the area of contact between the upper layer and the bottom layer.

Example 8a

The forced-air blanket of any of examples 1-8, wherein the linear seal length is at least 10% of the longitudinal dimension of the forced air blanket.

Example 8b

The forced-air blanket of any of examples 1-8, wherein the linear seal length is at least 20% of the longitudinal dimension of the forced air blanket.

Example 9

The forced-air blanket of any of examples 1-8, wherein one or more of the staked seals comprise an area in a range of 0.5 to 5.0 square centimeters of contact between the upper layer and the bottom layer.

Example 10

The forced-air blanket of any of examples 1-9, wherein the maximum distance of separation between the upper layer and the bottom layer within the interconnected air passageways is no greater than 9 centimeters.

Example 11

The forced-air blanket of any of examples 1-10, wherein the upper layer has a thickness dimension of in a range of 0.0005 to 0.02 inches for the material forming the upper layer, and the bottom layer has a thickness dimension of in a range of 0.0005 to 0.02 inches for the material forming the bottom layer.

Example 12

The forced-air blanket of any of examples 1-11, wherein one or more of the plurality of opening comprises an opening having a cross-sectional area of between 0.20 to 0.8 $mm^2$.

Example 13

The forced-air blanket of any of examples 1-12, wherein a first overall area of the plurality of openings included in bottom layer and within the periphery comprises a first area of about 23 $cm^2$, and a second overall area including any non-perforated portions of the bottom layer that are also included within the periphery comprise a second area of about 7056 $cm^2$.

Example 14

The forced-air blanket of any of examples 1-13, wherein the openings are arranged in a plurality of parallel rows, and wherein the spacing between each of the parallel rows is in a range of 6 to 18 mm.

Example 15

The forced-air blanket of example 14, wherein the spacing between the openings within a row of the parallel rows is in a range of 6 to 18 mm.

Example 16

The forced-air blanket of example 14, wherein the position of each opening in a particular row of the plurality of parallel rows is staggered with respect to the position of any of the openings in a row above and in a row below the particular row, and wherein the horizontal dimension for the amount of stagger is in a range of 3 to 9 mm.

Example 17

The forced-air blanket of any of examples 1-16, further comprising:
a second plurality of openings provided in the upper layer, the second plurality of openings configured to allow a profusion of air to pass through the upper layer.

Example 18

The forced-air blanket of any of examples 1-17, wherein the periphery comprises a rectangular shape having at least one cutout along a side corresponding to a longitudinal axis of the forced-air blanket.

Example 19

The forced-air blanket of any of examples 1-18, wherein the interconnected air passageways are configured to receive a flow of warmed air from the inlet, and to distribute the flow of warmed air across the bottom layer in order to provide the profusion of air from the plurality of openings in the bottom layer.

Example 20

A system for warming or cooling a patient, the system comprising: a source for generating a flow of air; and a forced-air blanket coupled to the source and configured to receive the flow of air from the source, and to distribute a profusion of the flow of air from one or more surfaces of the forced-air blanket, the forced-air blanket comprising: a structure comprising a first layer of material and a second layer of material, the first layer of material forming a bottom layer of the forced-air blanket, the bottom layer comprising a plurality of openings configured to allow a profusion of air to pass through the bottom layer, the second layer of material forming an upper layer of the forced-air blanket, the upper layer bonded to the bottom layer around a periphery to form an area of the upper layer and the bottom layer enclosed within the periphery, the upper layer further bonded to bottom layer by a plurality of linear seals and a plurality of staked seals forming a plurality of interconnected air passageways; and at least one air inlet coupled to the interconnecting air passageways, the inlet configured to receive a flow of air, and to provide the flow of air to the bottom layer through the interconnected air passageways; wherein the area enclosed within the periphery of the forced-air blanket provides an interior space comprising the plurality of interconnected air passageways between the upper layer and the bottom layer, the passageways further defined by a plurality of connections formed between the upper layer and the bottom layer within the area defined by the periphery, the plurality of linear seals, and the plurality of staked seals, and wherein at least one of the plurality of linear seals is sealingly joined to a portion of the periphery.

Example 21

The system of example 20, wherein the linear seals are located at end of the forced-air blanket and have a longitudinal orientation that corresponds to the longitudinal dimension of the forced-air blanket, and have a first end that joins with the periphery at an end to form a seal with periphery.

Example 22

The system of example 20, wherein the number of linear seals at each end of the forced-air blanket is greater than 2 and less than 5.

Example 23

The system of example 20, wherein the number of linear seals at each end of the forced-air blanket is 3.

Example 24

The system of any of examples 20-23, wherein two or more of the plurality staked seals for a row in a line that aligns with a longitudinal orientation of at least one of the linear seals.

Example 25

The system of any of examples 20-24, wherein the flow of air is provided to the forced-air blanket at a pressure of 10 mm Hg or less.

Example 26

The system of any of examples 20-25, wherein the plurality of linear seal and the plurality of staked seal are configured to limit the maximum distance between the at least one layer and the second layer within the passageway within the area enclosed by the periphery to no more than 9 centimeters.

Example 27

The system of any of examples 20-26, wherein a first overall area of the plurality of openings included in bottom layer and within the periphery comprises a first area of about 23 cm$^2$, and a second overall area included any non-perforated portions of the bottom layer and included within the periphery comprise a second area of about 7056 cm$^2$.

Example 28

The system of any of examples 20-27, wherein the second layer further comprises a second plurality of openings, the second plurality of openings configured to allow profusion of the flow of air through the second layer.

Example 29

The system of any of examples 20-28, wherein bonding the at least one layer to the second layer in the area enclosed by the periphery to form the plurality of linear seals and the plurality of staked seals comprises forming at least one of the plurality of linear seals and the plural of staked seals using a heat sealing technique.

Example 30

A method for forming a forced-air blanket, the method comprising: providing a first web layer that comprises a plurality of openings; providing a second web layer with or without perforations; forming an inlet in either the first web layer or the second web layer; and bonding the first web layer to the second web layer to form a sealed periphery and a plurality of linear seals and a plurality of staked steals.

Example 31

The method of example 30, wherein the linear seals are formed at an end of the forced-air blanket and have a longitudinal orientation that corresponds to the longitudinal dimension of the forced-air blanket, and have a first end that joins with the periphery at an end to form a seal with periphery.

Example 32

The method of example 30, wherein the number of linear seals at each end of the forced-air blanket is greater than 2 and less than 5.

Example 33

The method of example 30, wherein the number of linear seals at each end of the forced-air blanket is 3.

Example 34

The method of any of examples 30-33, wherein two or more of the plurality staked seals form a row in a line that aligns with a longitudinal orientation of at least one of the linear seals.

Example 35

The method of any of examples 30-34, wherein the plurality of linear seals and the plurality of staked seal are configured to limit a maximum distance between the at least one layer and the second layer within the passageway within the area enclosed by the periphery to no more than 9 centimeters.

Example 36

The method of any of examples 30-35, wherein a first overall area of the plurality of openings included in first web layer and within the periphery comprises a first area of about 23 cm$^2$, and a second overall area included any non-perforated portions of the bottom layer and included within the periphery comprise a second area of about 7056 cm$^2$.

Example 37

The method of any of examples 30-36, wherein the second web layer further comprises a second plurality of openings, the second plurality of openings configured to allow profusion of the flow of air through the second layer.

Example 38

The method of any of examples 30-37, wherein bonding the first web layer to the second web layer in the area enclosed by the periphery to form the plurality of linear seals and the plurality of staked seals comprises forming at least one of the plurality of linear seals and the plural of staked seals using a heat sealing technique.

Example 39

The method of any of examples 30-38, wherein bonding the first web layer to the second web layer in the area enclosed by the periphery to form the plurality of linear seals and the plurality of staked seals comprises forming at least one of the plurality of linear seals and the plural of staked seals using an ultrasonic welding technique.

Example 40

A warming blanket for warming a patient, the warming blanket comprising: a structure comprising a first layer of material and a second layer of material, the first layer of material forming a bottom layer of the warming blanket, the bottom layer configured to allow a profusion of air through the bottom layer, and the second layer of material forming an upper layer of the warming blanket, the upper layer coupled to the bottom layer around a periphery of the bottom layer to form an initial shape of the warming blanket and to form an interior space between the first layer of material and the second layer of material comprising a plurality of interconnected air passageways; at least one air inlet coupled to the interconnecting air passageways, the inlet configured to receive a flow of air, and to provide the flow of air to the bottom layer through the interconnected air passageways; wherein at least a portion of the structure is configured to be deformable in at least one dimension in order to reshape the periphery of the warming blanket while maintaining the integrity of the interconnecting air passageways throughout the structure, and wherein the portion of the blanket that is deformable is deformable by at least a 20% elongation.

Example 41

The warming blanket of example 40, wherein the portion of the blanket that is deformable is deformable by at least a 30% elongation.

Example 42

The warming blanket of example 40, wherein the portion of the blanket that is deformable is deformable by at least a 40% elongation.

Example 43

The warming blanket of example 40, wherein the portion of the blanket that is deformable is deformable by at least a 50% elongation.

Example 44

The warming blanket of example 40, wherein the warming blanket is configured so that when a force of deformation applied is less than 25 Newtons at 25% strain for a test sample of the deformable portion of the blanket that is 2.54 cm wide, according to a tensile strength testing with a gauge length of 50 mm and cross-head speed (pull speed) of 254 mm per minute.

Example 45

The warming blanket of any of examples 40-44, wherein the material or materials comprise a low density polyethylene.

Example 46

The warming blanket of any of examples 40-45, wherein the material or materials comprise a metallocene polyethylene or polypropylene or a styrene block copolymer.

Example 47

The warming blanket of any of examples 40-45, wherein the material or materials comprise a polyester such as polyether polyester.

Example 48

The warming blanket of any of examples 40-47, wherein the periphery comprises a rectangular shape having at least one cutout along a side corresponding to a longitudinal axis of the warming blanket.

Example 49

The warming blanket of example 48, wherein the at last one cutout comprises the portion of the warming blanket that is deformable.

Example 50

The warming blanket of any of examples 40-49, where the flow of air is maintained at a temperature between 36 to 43 C.

Example 51

The warming blanket of any of examples 40-50, wherein the structure comprises an end having a width axis aligned with a portion of the periphery forming the end of the structure, the warming blanket configured to be deformable so that the width axis is re-oriented by an amount up to 90-degrees from an initial angle of orientation of the width axis.

Example 52

The warming blanket of any of examples 40-51, wherein the structure comprises an end having a width axis aligned with a portion of the periphery forming the end of the structure, the warming blanket configured to be deformable so that the width axis is re-oriented by an amount up to 200-degrees from an initial angle of orientation of the width axis.

Example 53

The warming blanket of any of examples 40-52, wherein the interconnected air passageways are configured to receive a flow of air from the inlet provided in the top layer of the structure, and to distribute the flow of air across the area of the bottom layer in order to provide the profusion of air through the bottom layer.

Example 54

A system for warming a patient, the system comprising: a source for generating a flow of air; a warming blanket coupled to the source and configured to receive the flow warmed air from the source, and to distribute the flow of air for dispersion to patient, the warming blanket comprising: a structure comprising a first layer of material and a second layer of material, the first layer of material forming a bottom layer of the warming blanket, the bottom layer comprising openings configured to allow a profusion of air through the bottom layer, and the second layer of material forming an upper layer of the warming blanket, the upper layer coupled to the bottom layer around a periphery of the bottom layer to form an initial shape of the warming blanket and to form an interior space between the first layer of material and the second layer of material comprising a plurality of interconnected air passageways; wherein at least a portion of the structure is configured to be deformable in at least one dimension that is co-planer with a central plane of the warming blanket in order to reshape the periphery of the warming blanket having the initial shape so that the structure remains substantially within an area having a thickness dimension of the initial shape of the warming blanket and while maintaining the integrity of the interconnecting air passageways throughout the structure, and wherein the portion of the blanket that is deformable is deformable by at least a 20% elongation.

Example 55

The system of example 54, wherein the portion of the blanket that is deformable is deformable by at least a 30% elongation.

Example 56

The system of example 54, wherein the portion of the blanket that is deformable is deformable by at least a 40% elongation.

Example 57

The system of any of example 54, wherein the portion of the blanket that is deformable is deformable by at least a 50% elongation.

Example 58

The system of example 54, wherein the warming blanket is configured so that when a force of deformation applied is less than 25 Newtons at 25% strain for a test sample of the deformable portion of the blanket that is 2.54 cm wide, according to a tensile strength testing with a gauge length of 50 mm and cross-head speed (pull speed) of 254 mm per minute.

Example 59

The system of any of examples 54-58, wherein the flow of air is provided to the warming blanket at a pressure of 100 mm Hg or less.

Example 60

The system of any of examples 54-59, wherein at least some portion of the structure includes the periphery configured to be deformable by stretching a material or materials comprising that portion of the periphery.

Example 61

The system of any of examples 54-60, wherein the at least one portion of the structure that is configured to be deformable comprises material or materials comprising a low density polyethylene.

Example 62

The system of any of examples 54-60, wherein the at least one portion of the structure that is configured to be deformable comprises material or materials comprising a metallocene polyethylene.

Example 63

The system of any of examples 54-60, wherein the at least one portion of the structure that is configured to be deformable comprises material or materials comprising a polyester such as polyether polyester.

Example 64

A method of reshaping a warming blanket, the method comprising: positioning the warming blanket to form the warming blanket into an initial shape; deforming the warming blanket to form a shape with respect to the periphery that is a different shape from the initial shape formed by the periphery while maintaining the integrity of the passageways providing distribution of air flows through the interior space of the warming blanket, wherein a portion of the blanket that is deformed is deformed by at least a 20% elongation; and inflating, by the source generating the flow of air, the warming blanket to maintain the warming blanket in the shape that is different from the initial shape.

Example 65

The method of example 64, wherein the portion of the blanket that is deformed is deformed by at least a 30% elongation.

Example 66

The method of example 64, wherein the portion of the blanket that is deformed is deformed by at least a 40% elongation.

Example 67

The method of example 64, wherein the portion of the blanket that is deformed is deformed by at least a 50% elongation.

Example 68

A forced-air blanket for providing a profusion of air to a patient, the forced-air blanket comprising:
a structure comprising a first layer of material and a second layer of material,
the first layer of material forming a bottom layer of the forced-air blanket, the bottom layer comprising a plurality of openings configured to allow a profusion of air to pass through the bottom layer,
the second layer of material forming an upper layer of the forced-air blanket, the upper layer bonded to the bottom layer around a periphery to form an area of the upper layer and the bottom layer enclosed within the periphery, the upper layer further bonded to bottom layer by a plurality of linear seals and a plurality of staked seals forming a plurality of interconnected air passageways; and
at least one air inlet coupled to the interconnected air passageways, the air inlet configured to receive a flow of air, and to provide the flow of air to the bottom layer through the interconnected air passageways;

wherein the area enclosed within the periphery of the forced-air blanket provides an interior space comprising the plurality of interconnected air passageways between the upper layer and the bottom layer, the passageways further defined by a plurality of connections formed between the upper layer and the bottom layer within the area defined by the periphery, and by the plurality of linear seals, and the plurality of staked seals, wherein a first linear seal and a second linear seal of the plurality of linear seals are oriented longitudinally along the forced-air blanket, wherein the plurality of staked seals are arranged in a plurality of parallel rows including a first row, a second row, with each row having at least a first staked seal and a second staked seal;

wherein the first linear seal and the second linear seal are adjacent to each other;

wherein the first row is collinear with the first linear seal and the second row is collinear with the second linear seal;

wherein the plurality of staked seals are arranged in a rectilinear array having a staggered pattern.

Example 69

The forced-air blanket of example 68, wherein some of the plurality of staked seals are arranged in a first alternate row comprising a first alternate staked seal and a second alternate staked seal, wherein at least one staked seal of the first alternate row is arranged intermediate between the first row and the second row and arranged intermediate between two adjacent staked seals in the first row.

Example 70

The forced-air blanket of any of the preceding examples, wherein the first linear seal and the second linear seal are parallel to each other.

Example 71

The forced-air blanket of any of the preceding examples, wherein the first linear seal and the second linear seal are parallel to a longitudinal side of the forced-air blanket.

Example 72

The forced-air blanket of any of the preceding examples, wherein the first row is adjacent to the longitudinal side of the forced-air blanket.

Example 73

The forced-air blanket of any of the preceding examples wherein some of the plurality of staked seals are arranged in a second alternate row comprising two or more staked seals, wherein the second alternate row is arranged intermediate between the first row and the longitudinal side of the forced-air blanket.

Example 74

The forced-air blanket of any of the preceding examples, wherein some of the plurality of staked seals are arranged in a plurality of columns with a column comprising at least one staked seal of the first row at least one staked seal of the second row.

Example 75

The forced-air blanket of any of the preceding examples, wherein a column is perpendicular to the first row.

Example 76

The forced-air blanket of any of the preceding examples, wherein an alternate staked seal from the first alternate row is arranged intermediate between at least two columns from the plurality of columns.

Example 77

The forced-air blanket of any of the preceding examples, wherein at least one staked seal in a second alternate row is arranged intermediate between at least two columns from the plurality of columns.

Example 78

The forced-air blanket of any of the preceding examples, wherein the first alternate staked seal of the first alternate row is arranged intermediate between two adjacent staked seals in the second row.

Example 79

The forced-air blanket of any of the preceding examples, wherein at least one staked seal of the first alternate row is arranged intermediate between a first staked seal of the first row and a second staked seal of the second row.

Example 80

The forced-air blanket of any of the preceding examples, wherein a space between the first staked seal and the second staked seal of the first row is at least 4 cm.

Example 81

The forced-air blanket of any of the preceding examples, wherein a space between the first alternate row and first row is no greater than 40 cm.

Example 82

The forced-air blanket of any of the preceding examples, wherein at least the first linear seal is joined to a portion of the periphery at an end of the forced-air blanket to form a seal with the periphery.

Example 83

The forced-air blanket of any of the preceding examples, wherein at least one staked seal of the first alternate row is arranged diagonal from the first staked seal of the first row.

Example 84

The forced-air blanket of any of the preceding examples, wherein the periphery comprises at least one longitudinal side and at least one latitudinal side.

Example 85

The forced-air blanket of any of the preceding examples, wherein the first staked seal and the second staked seal in the first row is equally spaced with the first staked seal and the second staked seal in the second row.

Example 86

The forced-air blanket of any of the preceding examples, wherein the first staked seal is adjacent to the second staked seal of the first row.

Example 87

The forced-air blanket of any of the preceding examples, wherein at least two staked seals are equally spaced from at least two adjacent linear seals.

Example 88

The forced-air blanket of any of the preceding examples, wherein the first staked seal of the first row and an end of the first linear seal and the first staked seal of the second row and an end of the second linear seal are equally spaced.

Example 89

The forced-air blanket of any of the preceding examples, wherein the first staked seal of the first row is adjacent to an end of the first linear seal.

Example 90

The forced-air blanket of any of the preceding examples, wherein the end of the first linear seal is oriented away from the periphery.

Example 91

The forced-air blanket of any of the preceding examples, wherein four adjacent staked seals from the plurality of staked seals forms a rhomboid having a first diagonal and a second diagonal, wherein the first diagonal has a length greater than the second diagonal, wherein a rhomboid is a parallelogram having unequal adjacent sides.

Example 92

The forced-air blanket of any of the preceding examples, wherein the first diagonal is oriented askew from a longitudinal side of the forced-air blanket.

Example 93

The forced-air blanket of any of the preceding examples, wherein the first diagonal is oriented askew from a linear seal.

Example 94

The forced-air blanket of any of the preceding examples, wherein four adjacent staked seals from the plurality of staked seals forms a rhombus having a first diagonal and a second diagonal, wherein the first diagonal has a length greater than the second diagonal.

Example 95

The forced-air blanket of any of the preceding examples, wherein the first diagonal is oriented parallel to the first row of the forced-air blanket.

Example 96

The forced-air blanket of example 68, wherein the first staked seal from the second row is arranged intermediate between the first staked seal and the second staked seal from the first row.

Example 97

The forced-air blanket of example 96, wherein the first staked seal from the first row is not collinear with the first staked seal from the second row in a perpendicular axis to the first row.

Example 98

The forced-air blanket of any of examples 96-97, wherein four adjacent staked seals from the plurality of staked seals forms a rhombus having a first diagonal and a second diagonal, wherein the first diagonal has a length greater than the second diagonal.

Example 99

The forced-air blanket of example 98, wherein the first diagonal is oriented perpendicular with the first row.

Example 100

A forced-air blanket for providing a profusion of air to a patient, the forced-air blanket comprising:
a plurality of layers with a plurality of interior seals bonding at least two of the plurality of layers;
at least one air inlet having a center coupled to at least one of the plurality of layers;
wherein at least one elongated seal from the plurality of interior seals is positioned proximate to the inlet, wherein an elongated seal has two sides, with one side facing the inlet.

Example 101

The forced-air blanket of example 100, wherein proximate is at a distance less than a distance from the center to a staked seal.

Example 102

The forced-air blanket of any of the preceding examples, wherein the elongated side of the at least one elongated seal is oriented perpendicular to a radial distance from the center of the air inlet.

Example 103

The forced-air blanket of any of the preceding examples, further comprising a perimeter region around at least a portion of the air inlet.

Example 104

The forced-air blanket of any of the preceding examples, wherein the elongated side of the at least one elongated seal is positioned along a radius of curvature of the perimeter region.

Example 105

The forced-air blanket of any of the preceding examples, wherein the perimeter region is defined by a distance to the center of the air inlet.

Example 106

The forced-air blanket of any of the preceding examples, wherein the distance is less than a distance from a staked seal to the center.

Example 107

The forced-air blanket of any of the preceding examples, wherein the distance no greater than a distances between two adjacent staked seals.

Example 108

The forced-air blanket of any of the preceding examples, wherein the elongated side has a length of no greater than 50% of the perimeter region.

Example 109

The forced-air blanket of any of the preceding examples, wherein a longitudinal axis of at least one elongated seal is not aligned with a radial dimension of the air inlet.

Example 110

The forced-air blanket of any of the preceding examples, wherein a combined area of a plurality of seals is less than a combined area of space between the plurality of seals within a perimeter region.

Example 111

The forced-air blanket of any of the preceding examples, wherein a radial dimension of the air inlet aligns with at least two ends of an elongated seal.

Example 112

The forced-air blanket of any of the preceding examples, wherein the elongated seal has at least one curved side.

Example 113

The forced-air blanket of any of the preceding examples, wherein the curved side is the elongated side.

Example 114

The forced-air blanket of any of the preceding examples, wherein an elongated seal is C-shaped.

Example 115

The forced-air blanket of any of the preceding examples, wherein an elongated seal is ellipsoidal shaped.

Example 116

The forced-air blanket of any of the preceding examples, wherein an elongated seal is half-moon shaped.

Example 117

The forced-air blanket of any of the preceding examples, wherein a space between two elongated seals is at least 1 cm.

Example 118

The forced-air blanket of any of the preceding examples, wherein the plurality of layers comprises a first layer of material and a second layer of material, the first layer of material forming a bottom layer of the forced-air blanket, the bottom layer comprising a plurality of openings configured to allow a profusion of air to pass through the bottom layer, the second layer of material forming an upper layer of the forced-air blanket, the upper layer bonded to the bottom layer around a periphery to form an area of the upper layer and the bottom layer enclosed within the periphery.

Example 119

The forced-air blanket of any of the preceding examples, wherein the upper layer is further bonded to the bottom layer by the plurality of interior seals.

Example 120

The forced-air blanket of any of the preceding examples, wherein an area enclosed within the periphery of the forced-air blanket provides an interior space comprising the plurality of interconnected air passageways between the upper layer and the bottom layer, the interconnected air passageways further defined by a plurality of connections formed between the upper layer and the bottom layer within the area defined by the periphery, and by the plurality of interior seals.

Example 121

The forced-air blanket of any of the preceding examples, wherein the plurality of interior seals comprises a plurality of linear seals and a plurality of staked seals forming a plurality of interconnected air passageways.

Example 122

The forced-air blanket of any of the preceding examples, wherein the at least one air inlet is coupled to interconnected air passageways, the air inlet configured to receive a flow of air, and to provide the flow of air to the bottom layer through the interconnected air passageways.

Example 123

The forced-air blanket of any of the preceding examples, further comprising a first elongated seal and a second elongated seal, each seal having a length measured along a radius of curvature of a perimeter region.

Example 124

The forced-air blanket of any of the preceding examples, wherein the first elongated seal and the second elongated seal have a first space.

Example 125

The forced-air blanket of any of the preceding examples, wherein a combined length of a plurality of seals is less than a combined space between the plurality of seals within the perimeter region.

Example 126

The forced-air blanket of any of the preceding examples, wherein the combined length of a plurality of seals comprises at least the first elongated seal and a seal along a periphery.

Example 127

The forced-air blanket of any of the preceding examples, wherein the combined space is the sum total of spaces between the plurality of elongated seals within the perimeter region.

Example 128

The forced-air blanket of any of the preceding examples, wherein at least one air inlet is coupled to interconnected air passageways, the air inlet configured to receive a flow of air, and to provide the flow of air to a bottom layer through the interconnected air passageways.

Various examples of techniques associated with forced-air warming blankets have been described in this disclosure. These and other examples are within the scope of the following claims.

EXAMPLES

Example 1

A forced-air blanket was prepared according to the staggered pattern of FIG. 9A using two layers. The two layers were bonded together using a combination of linear and staked seals. The uninflated width of the blanket was measured at 36 inches.

Example 2

A forced-air blanket was prepared according to the staggered pattern of FIG. 11A using two layers. The two layers were bonded together using a combination of linear and staked seals. The uninflated width of the blanket was measured at 36 inches and is shown in FIGS. 13-14.

After being allowed to inflate, the width of each blanket was measured on a flat surface and recorded in Table 1.

TABLE 1

| Inflation results | | |
|---|---|---|
| Example | Uninflated Width (in) | Inflated Width (in) |
| 1 | 36 | 26 |
| 2 | 36 | 30 |

Unexpectedly, the staggered pattern in example 2 increased the inflated width of the forced-air blanket.

What is claimed is:

1. A forced-air blanket for providing a profusion of air to a patient, the forced-air blanket comprising:
a plurality of layers with a plurality of interior seals bonding at least a first layer and a second layer of the plurality of layers; wherein the first layer comprises a plurality of openings and the second layer is impervious to air;
at least one air inlet having a center, the air inlet being coupled to at least one of the plurality of layers, the air inlet defining a circular-shaped perimeter region around the air inlet, wherein the perimeter region is defined by a distance from the center of the air inlet, the distance being no greater than 50 cm, and wherein the circular-shaped perimeter region has a radius of curvature;
wherein the plurality of interior seals comprises a plurality of elongated seals positioned on the radius of curvature of circular-shaped perimeter region around the air inlet, and wherein the plurality of elongated seals comprises at least 3 elongated seals wherein each elongated seal has two elongated sides, with one of the elongated sides facing the air inlet, wherein facing the air inlet means that the elongated seal is oriented perpendicular to a radial distance from the center of the air inlet.

2. The forced-air blanket of claim 1, wherein the circumference of the perimeter region is less than a distance from a staked seal to the center.

3. The forced-air blanket of claim 1, wherein the circumference of the perimeter region is no greater than a distance between two adjacent staked seals.

4. The forced-air blanket of claim 1, wherein the sum of the lengths of the elongated seals have a length that is no greater than 50% of the circumference of the perimeter region.

5. The forced-air blanket of claim 1, further comprising at least one additional elongated seal wherein the longitudinal axis of the at least one additional elongated seal is not aligned with a radial dimension of the air inlet.

6. The forced-air blanket of claim 1, wherein the distance is no greater than 40 cm.

7. The forced-air blanket of claim 1, wherein the distance is no greater than 30 cm.

\* \* \* \* \*